US009919006B2

(12) United States Patent
Charmot et al.

(10) Patent No.: US 9,919,006 B2
(45) Date of Patent: *Mar. 20, 2018

(54) COMPOSITIONS AND METHODS FOR TREATING HYPERKALEMIA

(71) Applicant: Ardelyx, Inc., Fremont, CA (US)

(72) Inventors: Dominique Charmot, Napa, CA (US); James P. Davidson, Mountain View, CA (US); Fangling Lin, Belmont, CA (US); Jeffrey W. Jacobs, San Mateo, CA (US); Natalia Blinova, Berkeley, CA (US); Eric Labonte, Belmont, CA (US); Ingrid Langsetmo, Golden Valley, MN (US); Robert C. Blanks, Auburndale, MA (US)

(73) Assignee: Ardelyx, Inc., Freemont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/223,798

(22) Filed: Jul. 29, 2016

(65) Prior Publication Data

US 2017/0173072 A1    Jun. 22, 2017

Related U.S. Application Data

(63) Continuation of application No. 15/052,186, filed on Feb. 24, 2016, now Pat. No. 9,433,640, which is a continuation of application No. 14/912,682, filed as application No. PCT/US2015/067460 on Dec. 22, 2015, now Pat. No. 9,655,921.

(60) Provisional application No. 62/096,447, filed on Dec. 23, 2014.

(51) Int. Cl.
  *A61K 31/795*  (2006.01)
  *A61K 9/00*    (2006.01)
  *A61K 9/14*    (2006.01)

(52) U.S. Cl.
  CPC .......... *A61K 31/795* (2013.01); *A61K 9/0056* (2013.01); *A61K 9/0095* (2013.01); *A61K 9/14* (2013.01)

(58) Field of Classification Search
  CPC ............... A61K 31/795; B01J 39/20
  See application file for complete search history.

(56) References Cited

U.S. PATENT DOCUMENTS

| | | |
|---|---|---|
| 8,785,416 B2 | 7/2014 | Verges Milano et al. |
| 9,433,640 B2 | 9/2016 | Charmot et al. |
| 2008/0081072 A1* | 4/2008 | Cherukuri ............ A61K 31/135 424/486 |
| 2011/0028412 A1 | 2/2011 | Cappello et al. |
| 2012/0172216 A1* | 7/2012 | Bohringer ............ A61K 33/44 502/416 |
| 2012/0309707 A1 | 12/2012 | Verges Milano et al. |
| 2015/0306135 A1 | 10/2015 | Fabregas et al. |
| 2016/0346318 A1 | 12/2016 | Charmot et al. |

FOREIGN PATENT DOCUMENTS

| | | |
|---|---|---|
| EP | 0 976 408 A1 | 2/2000 |
| EP | 1 031 345 A1 | 8/2000 |
| GB | 1 561 395 A | 2/1980 |
| JP | S57 193414 | 11/1983 |
| WO | WO 2010/022381 A1 | 2/2010 |
| WO | WO 2012/102362 A1 | 8/2012 |
| WO | WO 2014/020222 A1 | 2/2014 |
| WO | WO 2014/096485 A1 | 6/2014 |

OTHER PUBLICATIONS

Vijay, S. et al. "Ion Exchange Resins and their Applications" Journal of Drug Delivery & Therapeutics; 2014, 4(4), 115-123.*
Jackson, M.B. et al. "Effect of the Degree of Crosslinking on the Selectivity of Ion-exchange Resins" J. Chern. Tech. Biotechnol. 1986,36,88-94.*
Resonium (http://products.sanofi.ca/en/resonium-calcium.pdf) Jul. 9, 2014, p. 1-12.*
Jackson, M.B. et al. "Effect of the Degree of Crosslinking on the Selectivity of Ion-exchange Resins" J. Chem. Tech. Biotechnol. 1986, 36, 88-94 (Year: 1986).*
Miura, Y. et al. "Ion Chromatographic Determination of L-Ascorbic Acid, Sulfite, Sulfide and Thiosulfate Using a Cation-Exchanger of Low Crosslinking" Analytical Sciences Aug. 1995, vol. 11, 617-621 (Year: 1995).*
Miura, Y. et al. "Ion Chromatographic Determination of L-Ascorbic Acid, Sulfite, Sulfide and Thiosulfate Using a Cation-Exchanger of Low Crosslinking" *Analytical Sciences*, 1995, vol. 11, p. 617-621.
Ahmed J. et al. "Hyperkalemia in Dialysis Patients", *Seminars in Dialysis* 2001, vol. 14, No. 5, p. 348-356.
Bakris G. L. et al. "ACE inhibition or angiotensin receptor blockade: Impact on potassium in renal failure", *Kidney International* 2000, vol. 58, p. 2084-2092.
Berge, S.M. et al. "Pharmaceutical Salts" *Journal of Pharmaceutical Sciences*, 1977, vol. 66, No. 1, p. 1-19.
Chernin G. et al., "Secondary Prevention of Hyperkalemia With Sodium Polystyrene Sulfonate in Cardiac and Kidney Patients on Renin-Angiotensin-Aldosterone System Inhibition Therapy", *Clinical Cardiology* 2012, 35(1), p. 32-36.
Choudhry N. K. et al., "Trends in adherence to secondary prevention medications in elderly post-myocardial infarction patients", *Pharmacoepidemiol Drug Saf.* 2008, vol. 17, No. 12, p. 1189-1196.
Database Caplus [Online] Chemical Abstracts Services, "Cation exchanger for treatment of hyperkalemia", XP002755511, retrieved from STN Database accession No. 1983:78158.

(Continued)

*Primary Examiner* — Yong S Kwon
*Assistant Examiner* — Andrew S Rosenthal
(74) *Attorney, Agent, or Firm* — Cooley LLP; Dean Farmer; Serge R. Banni

(57) ABSTRACT

The present invention is directed to compositions and methods of removing potassium or treating hyperkalemia by administering pharmaceutical compositions of cation exchange polymers with low crosslinking for improved potassium excretion and for beneficial physical properties to increase patient compliance.

28 Claims, 20 Drawing Sheets

(56) References Cited

OTHER PUBLICATIONS

Dave, R. H., "Overview of pharmaceutical excipients used in tablets and capsules," Drug Topics, http://drugtopics.modernmedicine.com/drug-topics/news/modernmedicine/modern-medicine-news/overview-pharmaceutical-excipients-used-tablets, 2008, pp. 1-11.
"Dowex 50WX2 hydrogen form. 200-400 mesh", Sigma Aldrich Products XP002755510. Retrieved from the Internet: URL:http://www.sigmaaldrich.comjcatalogjproductjsial/217476?lang=de&region=DE [retrieved on Mar. 15, 2016].
Edes T. E. et al., "Heparin-Induced Hyperkalemia", *Arch. Intern. Med.* 1985, vol. 145, p. 1070-1072.
Einhorn L. M. et al. "The frequency of hyperkalemia and its significance in chronic kidney disease", *Arch Intern Med.* 2009, vol. 169, No. 12, p. 1156-1162.
Fordjour K. N. et al. "Management of Hyperkalemia in Hospitalized Patients", *The American Journal of the Medical Sciences*, 2014, 347(2), p. 93-100.
Giebisch G. "Renal potassium transport: mechanisms and regulation", *Am. J. Physiol.* 1998, vol. 274, No. 5, p. F817-833.
Giebisch G. "A trail of research on potassium", *Kidney Int.* 2002, vol. 62, No. 5, p. 1498-1512.
Holbrook J. T. et al., "Sodium and potassium intake and balance in adults consuming self-selected diets", *The American Journal of Clinical Nutrition* 1984, vol. 40, p. 786-793.
Jackson, M.B. et al. "Effect of the Degree of Crosslinking on the Selectivity of Ion-exchange Resins" *J. Chem. Tech. Biotechnol.* 1986, 36, p. 88-94.
Kessler C. et al., "The Use of Sodium Polystyrene Sulfonate in the Inpatient Management of Hyperkalemia", *Journal of Hospital Medicine* 2011, vol. 6, No. 3, p. 136-140.
Kovesdy C. P. "Management of hyperkalaemia in chronic kidney disease", *Nat. Rev. Nephrol.* 2014, vol. 10, p. 653-662.
Li, X. et al. "Calcium Polystyrene Sulfonate in Treating Hyperkalemia Patients With Renal Insufficiency", *Nephrology Dialysis Transplantation*, vol. 28, No. Suppl. 1, 2013, p. i405.
MacDonald J. E. et al. "What is the Optimal Serum Potassium Level in Cardiovascular Patients?", *Journal of American College of Cardiology* 2004, vol. 43, No. 2, p. 155-161.
McMahon G. M. et al., "Association between hyperkalemia at critical care initiation and mortality", *Intensive Care Med.* 2012, vol. 38, p. 1834-1842.
Palmer B. F. "Regulation of Potassium Homeostasis", *Clin. J. Am. Soc. Nephrol.* 2015, vol. 10, p. 1050-1060.
Roger V. L. et al., "Executive Summary: Heart Disease and StrokeStatistics—2012 Update", *Circulation* 2012, 125, p. 188-197.
Sandle G. I. "Segmental variability of membrane conductances in rat and human colonic epithelia", *Pflügers Arch.* 1987, vol. 410, p. 173-180.
Sandle G. I. "Apical potassium (BK) channels and enhanced potassium secretion in human colon", *Q. J. Med.* 2010, vol. 103, p. 85-89.
Scherr L. et al., "Management of Hyperkalemia with a Cation-Exchange Resin", *The New England Journal of Medicine* 1961, vol. 264, No. 3, p. 115-119.
Schroder C. H. "Reduction of potassium in drinks by pre-treatment with calcium polystyrene sulphonate", *Eur. J. Pediatr.* 1993, vol. 152, p. 263-264.
Sorensen M. V. "The secretory KCa1.1 channel localises to crypts of distal mouse colon: functional and molecular evidence", *Pflugers Arch.—Eur. J. Physiol.* 2011, vol. 462, p. 745-752.
Tzamaloukas A. H. et al. "Temporal Profile of Serum Potassium Concentration in Nondiabetic and Diabetic Outpatients on Chronic Dialysis", *Am. J. Nephrol.* 1987, vol. 7, p. 101-109.
Vippagunta, S.R. et al., "Crystalline Solids", *Advanced Drugs Delivery Review* 2001, 48(1), p. 3-26.
Wassenberg M. et al., "Costs and benefits of rapid screening of methicillin-resistant *Staphylococcus aureus* carriage in intensive care units: a prospective multicenter study", *Critical Care* 2012, 16:R22, 8 pages.
Weiner I. D. et al. "Hyperkalemia: A Potential Silent Killer", *J. Am. Soc. Nephrol.* 1998, vol. 9, p. 1535-1543.
Weir M. A. et al. "Beta-Blockers, Trimethoprim-Sulfamethoxazole, and the Risk of Hyperkalemia Requiring Hospitalization in the Elderly: A Nested Case-Control Study", *Clin. J. Am. Soc. Nephrol.* 2010, vol. 5, p. 1544-1551.

* cited by examiner

* is significantly different than Vehicle
^ is significantly different than Example 4

* Significant from vehicle; ^ significant from Na PSS, USP:
significant from CaPSS, BP
* p < 0.05,  p<0.01, * p < 0.001

\* Significant from vehicle; ^ significant from NaPSS, USP
\* p < 0.05, \*\* p<0.01, \*\*\* p < 0.001

* Significant from control
* p < 0.05,  p<0.01, * p < 0.001

| DVB weight % | DVB mole % | Styrene:DVB ("m" to "n" ratio) |
|---|---|---|
| 1.00% | 0.80 | 123.8 |
| 1.20% | 0.96 | 102.9 |
| 1.50% | 1.20 | 82.1 |
| 1.60% | 1.28 | 76.9 |
| 1.80% | 1.45 | 68.2 |
| 2.00% | 1.61 | 61.3 |
| 2.08% | 1.67 | 58.8 |
| 2.20% | 1.77 | 55.6 |
| 2.50% | 2.01 | 48.8 |
| 3.00% | 2.41 | 40.4 |
| 4.00% | 3.23 | 30.0 |
| 6.40% | 5.19 | 18.3 |
| 8.00% | 6.50 | 14.4 |
| 10.00% | 8.16 | 11.3 |

FIG. 12

* Is statistically different from Na-PSS, USP
^ Is statistically different from Ca-PSS, BP
Is statistically different from Example 30
* $p < 0.05$,  $p < 0.01$, * $p < 0.001$

COMPOSITIONS AND METHODS FOR TREATING HYPERKALEMIA

RELATED APPLICATIONS

This application is a continuation of U.S. application Ser. No. 15/052,186, filed Feb. 24, 2016, now allowed, which is a continuation of U.S. application Ser. No. 14/912,682, filed Feb. 18, 2016, which is a National Phase application of International Application No. PCT/US2015/067460, filed Dec. 22, 2015, which claims the benefit of and priority to U.S. provisional application No. 62/096,447, filed Dec. 23, 2014, the entire contents of each of which are incorporated herein by reference in their entireties.

FIELD OF INVENTION

The present invention relates to compositions and methods of removing potassium from the gastrointestinal track, including methods of treating hyperkalemia, by administration of crosslinked cation exchange polymers with a low level of crosslinking for improved potassium excretion and for improved patient tolerance and compliance.

BACKGROUND OF THE INVENTION

Potassium is the most abundant cation in the intracellular fluid and plays an important role in normal human physiology, especially with regard to the firing of action potential in nerve and muscle cells (Giebisch G. *Am J Physiol.* 1998, 274(5), F817-33). Total body potassium content is about 50 mmol/kg of body weight, which translates to approximately 3500 mmols of potassium in a 70 kg adult (Ahmed, J. and Weisberg, L. S. *Seminars in Dialysis* 2001, 14(5), 348-356). The bulk of total body potassium is intracellular (~98%), with only approximately 70 mmol (~2%) in the extracellular space (Giebisch, G. H., *Kidney Int.* 2002 62(5), 1498-512). This large differential between intracellular potassium (~120-140 mmol/L) and extracellular potassium (~4 mmol/L) largely determines the resting membrane potential of cells. As a consequence, very small absolute changes in the extracellular potassium concentration will have a major effect on this ratio and consequently on the function of excitable tissues (muscle and nerve) (Weiner, I. D. and Wingo, C. S., *J. Am. Soc. Nephrol.* 1998, 9, 1535-1543). Extracellular potassium levels are therefore tightly regulated.

Two separate and cooperative systems participate in potassium homeostasis, one regulating external potassium balance (the body parity of potassium intake vs. potassium elimination) while the other regulates internal potassium balance (distribution between intracellular and extracellular fluid compartments) (Giebisch, *Kidney Int* 2002). Intracellular/extracellular balance provides short-term management of changes in serum potassium, and is primarily driven physiologically by the action of $Na^+$, $K^+$-ATPase "pumps," which use the energy of ATP hydrolysis to pump Na and K against their concentration gradients (Giebisch, *Kidney Int* 2002). Almost all cells possess an $Na^+$, $K^+$-ATPase (Palmer, B. F., *Clin. J. Am. Soc. Nephrol.* 2015, 10(6), 1050-60). Body parity is managed by elimination mechanisms via the kidney and gastrointestinal tract: in healthy kidneys, 90-95% of the daily potassium load is excreted through the kidneys with the balance eliminated in the feces (Ahmed, *Seminars in Dialysis* 2001).

Due to the fact that intracellular/extracellular potassium ratio ($K_i$:$K_e$ ratio) is the major determinant of the resting membrane potential of cells, small changes in $K_e$ (i.e., serum [K]) have profound effects on the function of electrically active tissues, such as muscle and nerve. Potassium and sodium ions drive action potentials in nerve and muscle cells by actively crossing the cell membrane and shifting the membrane potential, which is the difference in electrical potential between the exterior and interior of the cell. In addition to active transport, $K^+$ can also move passively between the extracellular and intracellular compartments. An overload of passive $K^+$ transport, caused by higher levels of blood potassium, depolarizes the membrane in the absence of a stimulus. Excess serum potassium, known as hyperkalemia, can disrupt the membrane potential in cardiac cells that regulate ventricular conduction and contraction. Clinically, the effects of hyperkalemia on cardiac electrophysiology are of greatest concern because they can cause arrhythmias and death (Kovesdy, C. P., *Nat. Rev. Nephrol.* 2014, 10(11), 653-62). Since the bulk of body parity is maintained by renal excretion, it is therefore to be expected that as kidney function declines, the ability to manage total body potassium becomes impaired.

The balance and regulation of potassium in the blood requires an appropriate level of intake through food and the effective elimination via the kidneys and digestive tract. Under non-disease conditions, the amount of potassium intake equals the amount of elimination, and hormones such as aldosterone act in the kidneys to stimulate the removal of excess potassium (Palmer, B. F. *Clin. J. Am. Soc. Nephrol.* 2015, 10(6), 1050-60). The principal mechanism through which the kidneys maintain potassium homeostasis is the secretion of potassium into the distal convoluted tubule and the proximal collecting duct. In healthy humans, serum potassium levels are tightly controlled within the narrow range of 3.5 to 5.0 mEq/L (Macdonald, J. E. and Struthers, A. D. *J. Am. Coll. of Cardiol.* 2004, 43(2), 155-61). As glomerular filtration rate (GFR) decreases, the ability of the kidneys to maintain serum potassium levels in a physiologically normal range is increasingly jeopardized. Studies suggest that the kidneys can adjust to a decrease in the number of nephrons by increasing potassium secretion by the surviving nephrons, and remain able to maintain normokalemia. However, as kidney function continues to decline these compensatory mechanisms cannot respond to potassium load and serum K increases (Kovesdy, *Nat. Rev. Nephrol.* 2014). Potassium homeostasis is generally maintained in patients with advanced CKD until the glomerular filtration rate (GFR; a measure of kidney function) falls below 10-15 mL/min. At this point, compensatory increases in the secretory rate of K+ in remaining nephrons cannot keep up with potassium load (Palmer, *J. Am. Soc. Nephrol.* 2015). Excessive levels of potassium build up in the extracellular fluid, hence leading to hyperkalemia.

Hyperkalemia is a clinically significant electrolyte abnormality that can cause severe electrophysiological disturbances, including cardiac arrhythmias and death. Hyperkalemia is defined as a serum potassium level above the normal range, typically >5.0 mmol/L (Kovesdy, *Nat. Rev. Nephrol.* 2014). Moderate hyperkalemia (serum potassium above 6.0 mEq/L) has been reported to have a 1-day mortality rate up to 30 times higher than that of patients with serum potassium less than 5.5 mEq/L (Einhorn, L. M., et al. *Arch Intern Med.* 2009, 169(12), 1156-1162). Severe hyperkalemia (serum K+ of at least 6.5 mmol/L) is a potentially life-threatening electrolyte disorder that has been reported to occur in 1% to 10% of all hospitalized patients and constitutes a medical emergency requiring immediate treatment (An, J. N. et al., *Critical Care* 2012, 16, R225). Hyperkalemia is caused by deficiencies in potassium excretion, and since the kidney is the primary mechanism of potassium removal, hyperkalemia commonly affects patients with kidney diseases such as chronic kidney disease (CKD; Einhorn, *Arch Intern Med.* 2009) or end-stage renal disease (ESRD; Ahmed, *Seminars in Dialysis* 2001). However, episodes of hyperkalemia can occur in patients with normal kidney function, where it is still a life-threatening condition. For example, in hospitalized patients, hyperkalemia has been associated with increased mortality in patients both with and without CKD (Fordj our, K. N., et al *Am. J. Med. Sci.* 2014, 347(2), 93-100).

While CKD is the most common predisposing condition for hyperkalemia, the mechanisms driving hyperkalemia typically involve a combination of factors, such as increased dietary potassium intake, disordered distribution of potassium between intracellular and extracellular compartments and abnormalities in potassium excretion. These mechanisms can be modulated by a variety of factors with causality outside of CKD. These include the presence of other comorbidities, such as type 2 diabetes mellitus (T2DM), cardiovascular disease (CVD) or the use of co-medications that can disrupt potassium homeostasis as side effects, such as blockade of the renin-angiotensin-aldosterone system (RAAS). These contributing factors to hyperkalemia are described below.

In clinical practice, CKD is the most common predisposing condition for hyperkalemia (Kovesdy, *Nat. Rev. Nephrol.* 2014). Other common predisposing conditions, often comorbidities with CKD, include both type 2 diabetes mellitus (T2DM) and cardiovascular disease (CVD), both of which are linked to the development of hyperkalemia through different mechanisms. Insulin deficiency and hypertonicity caused by hyperglycemia in patients with diabetes contributes to an inability to disperse high acute potassium loads into the intracellular space. Furthermore, diabetes mellitus is associated with hyporeninemic hypoaldosteronism and the resultant inability to upregulate tubular potassium secretion (Kovesdy, *Nat. Rev. Nephrol.* 2014). Cardiovascular disease (CVD) and other associated conditions, such as acute myocardial ischaemia, left ventricular hypertrophy and congestive heart failure (CHF), require various medical treatments that have been linked to hyperkalaemia. For example, β2-adrenergic-receptor blockers, which have beneficial antihypertensive effects via modulation of heart rate and cardiac contractility, contribute to hyperkalemia through inhibition of cellular adrenergic receptor-dependent potassium translocation, causing a decreased ability to redistribute potassium to the intracellular space (Weir, M. A., et al., *Clin. J. Am. Soc. Nephrol.* 2010, 5, 1544-15515). Heparin treatment, used to manage or prevent blood clots in CVD, has also been linked to hyperkalemia through decreased production of aldosterone (Edes, T. E., et al., *Arch. Intern. Med.* 1985, 145, 1070-72)). Cardiac glycosides such as digoxin—used to help control atrial fibrillation and atrial flutter—inhibit cardiac $Na^+/K^+$-ATPase, but also modulate the related $Na^+/K^+$-APTases in the nephrons. This can inhibit the ability of the kidney to secrete potassium into the collecting duct and can also cause hyperkalemia.

Hyperkalemia occurs especially frequently in patients with CKD who are treated with certain classes of medications, such as angiotensin-converting-enzyme (ACE) inhibitors, angiotensin-receptor blockers (ARBs) or other inhibitors of the renin-angiotensin-aldosterone system (RAAS) (Kovesdy, *Nat. Rev. Nephrol.* 2014). The RAAS is important for the regulation of blood pressure, and the maximum doses of RAAS inhibitors are widely recommended for patients with hypertension, heart failure (HF), chronic kidney disease (CKD), and diabetes. Large outcome studies have shown that RAAS inhibitors can significantly decrease hospitalization, morbidity, and mortality in these patients. In patients with CKD, RAAS inhibition is beneficial for some of the common comorbidities, such as congestive heart failure (CHF). However, inhibition of the RAAS pathway also promotes potassium retention and is a major cause of hyperkalemia. Even in populations without CKD, RAAS inhibitor monotherapy (treatment with a single agent) has an incidence of hyperkalemia of <2%, but this increased to ~5% in patients receiving dual-agent RAAS inhibitor therapy. This is further exacerbated in CKD patients, where the incidence of hyperkalemia rises to 5-10% when dual therapy is administered (Bakris, G. L., et al., *Kid. Int* 2000, 58, 2084-92, Weir, *Clin. J. Am. Soc. Nephrol.* 2010). It is therefore often difficult or impossible to continue RAAS inhibitor therapy over extended periods of time. Hyperkalemia is perhaps the most important cause of the intolerance to RAAS inhibitors observed in patients with CKD. As a consequence, hyperkalemia has led to the suboptimal use of RAAS inhibitors in the treatment of serious diseases such as CKD and heart failure (Kovesdy, *Nat. Rev. Nephrol.* 2014).

Congestive heart failure patients, especially those taking RAAS inhibitors, are another large group that is at risk of developing life-threatening levels of serum potassium. The decreased heart output and corresponding low blood flow through the kidneys, coupled with inhibition of aldosterone, can lead to chronic hyperkalemia. Approximately 5.7 million individuals in the US have congestive heart failure (Roger, V. L., et al., *Circulation.* 2012, 125, 188-197). Most of these are taking at least one RAAS inhibitor, and studies show that many are taking a suboptimal dose, often due to hyperkalemia (Choudhry, N. K. et al, *Pharmacoepidem. Dr. S.* 2008, 17, 1189-1196).

In summary, hyperkalemia is a proven risk factor for adverse cardiac events, including arrhythmias and death. Hyperkalemia has multiple causalities, the most common of which is chronic or end-stage kidney disease (CKD; ESRD); however, patients with T2DM and CVD are also at risk for hyperkalemia, especially if CKD is present as a comorbidity. Treatment of these conditions with commonly prescribed agents, including RAAS inhibitors, can exacerbate hyperkalemia, which often leads to dosing limitations of these otherwise proven beneficial agents. There is therefore a clear need for a potassium control regimen to not only control serum K in the CKD/ESRD population, but also permit the administration of therapeutic doses of cardio-protective RAAS inhibitor therapy.

Dietary intervention is one possible point of control for managing potassium burden, but is difficult to manage. Furthermore, in the patient population susceptible to hyperkalemia, dietary modifications often involve an emphasis on sodium restriction, and some patients switch to salt substitutes, not realizing that these can contain potassium salts (Kovesdy, *Nat. Rev. Nephrol.* 2014). Finally, "heart-healthy" diets are inherently rich in potassium. Ingested potassium is also readily bioavailable, and rapidly partitions into extracellular fluid. For example, the typical daily potassium intake in healthy individuals in the United States is approximately 70 mmol/d, or ~1 mmol/kg of body weight for a 70 kg individual (Holbrook, J. T., et al., *Am. J of Clin. Nutrition.* 1984, 40, 786-793). Since absorption of ingested potassium from the gut into the extracellular fluid is nearly complete, and assuming ~17 l of extracellular fluid in a 70 kg adult, this potassium burden would essentially double serum K (70 mmol/17 L=~4 mmol/L increase). Such an increase would be lethal in the absence of compensatory mechanisms, and the fact that ESRD patients on dialysis do not die during the interdialytic interval is a testament to the integrity of the extrarenal potassium disposal mechanisms that get upregulated in ESRD (Ahmed, *Seminars in Dialysis* 2001). Patients with normal renal function eliminate ~5-10% of their daily potassium load through the gut (feces). In patients with chronic renal failure, fecal excretion can account for as much as 25% of daily potassium elimination. This adaptation is mediated by increased colonic secretion, which is 2- to 3-fold higher in dialysis patients than in normal volunteers (Sandle, G. I. and McGlone, F., *Pflugers Arch* 1987, 410, 173-180). This increase in fecal excretion appears due to the upregulation of the amount and location of so-called "big potassium" channels (BK channels; KCNMA1) present in the colonic epithelia cells, as well as an alteration in the regulatory signals that promote potassium secretion through these channels (Sandle, G. I. and Hunter, M. Q., *J Med* 2010, 103, 85-89; Sorensen, M. V. *Pflugers Arch—Eur J. Physiol* 2011, 462, 745-752). Additional compensation is also provided by cellular uptake of potassium (Tzamaloukas, A. H. and Avasthi, P. S., *Am. J. Nephrol.* 1987, 7, 101-109). Despite these compensatory mechanisms, ~15-20% of the ingested potassium accumulates in the extracellular space and must be removed by dialysis. Interdialytic increases that occur over the weekend can lead to serious cardiovascular events, including sudden death. In summary, dietary intervention is both impractical and insufficient.

Serum potassium can be lowered by two general mechanisms: the first is by shifting potassium intracellularly using agents such as insulin, albuterol or sodium bicarbonate (Fordjour, *Am. J. Med. Sci.* 2014). The second is by excreting it from the body using 1 of 4 routes: the stool with K binding resins such as sodium polystyrene sulfonate (Na-PSS), the urine with diuretics, the blood with hemodialysis or the peritoneal fluid with peritoneal dialysis (Fordjour, *Am. J Med. Sci.* 2014). Other than Na-PSS, the medications that treat hyperkalemia, such as insulin, diuretics, beta agonists and sodium bicarbonate, simply cause hypokalemia as a side effect and are not suitable as chronic treatments. Definitive therapy necessitates the removal of potassium from the body. Studies have confirmed that reducing serum potassium levels in hyperkalemia patients actually reduces the mortality risk, further solidifying the role of excess potassium in the risk of death. One study found that treatment of hyperkalemia with common therapies both improved serum potassium levels and resulted in a statistically significant increase in survival (An, *Critical Care* 2012). Another study, in hospitalized patients receiving critical care, showed that the reduction of serum potassium by ≥1 mEq/L 48 hours after hospitalization also decreased the mortality risk (McMahon, G. M., et al., *Intensive Care Med*, 2012, 38, 1834-1842). These studies suggest that treating hyperkalemia in the acute and chronic settings can have a real impact on patient outcomes by reducing the risk of death The potassium binder sodium polystyrene sulfonate (Na-PSS; Kayexalate) is the most common agent used in the management of hyperkalemia in hospitalized patients (Fordjour, *Am. J. Med. Sci.* 2014). Polystyrene sulfonate (PSS) is typically provided as a sodium salt (Na-PSS), and in the lumen of the intestine it exchanges sodium for secreted potassium. Most of this takes place in the colon, the site of most potassium secretion in the gut (and the region where K secretion appears to be upregulated in CKD). Each gram of Na-PSS can theoretically bind ~4 mEq of cation; however, approximately 0.65 mmol of potassium is sequestered in vivo due to competing cations (e.g., hydrogen ion, sodium, calcium and magnesium). Sodium is concomitantly released. This may lead to sodium retention, which can lead to hypernatremia, edema, and possible worsening of hypertension or acute HF (Chemin, G. et al., *Clin. Cardiol.* 2012, 35(1), 32-36).

Na-PSS was approved in 1958 by the US FDA, as a potassium-binding resin in the colon for the management of hyperkalemia. This approval was based on a clinical trial performed in 32 hyperkalemic patients, who showed a decrease in serum potassium of 0.9 mmol/l in the first 24 h following treatment with Na-PSS (Scherr, L. et al., *NEJM* 1961, 264(3), 115-119). Such acute use of Na-PSS has become common. For example, the use of potassium-binding resins has proven to be of value in the pre-dialysis CKD setting and in the management of emergency hyperkalemia, and is reportedly used in >95% of hyperkalemic episodes in the hospital setting (Fordjour, *Am. J. Med. Sci.* 2014). Na-PSS can be given orally or rectally. When given orally, it is commonly administered with sorbitol to promote diarrhea/prevent constipation. The onset of action is within 1-2 h and lasts approximately 4-6 hours. The recommended average daily dose is 15-60 g given singly or in divided doses (Kessler, C. et al., *J. Hosp. Med.* 2011, 6(3), 136-140). Kayexalate has been shown to be active in broad populations of hyperkalemic patients, including subjects both with and without chronic kidney disease (Fordjour, *Am. J. Med. Sci.* 2014).

There are fewer reports of the use of Na-PSS in chronic hyperkalemia, but chronic treatment is not uncommon. Chernin et al. report a retrospective study of patients on RAAS inhibition therapy that were treated chronically with Na-PSS as a secondary prevention of hyperkalemia (Chernin, *Clin. Cardiol.* 2012). Each patient began chronic treatment after being first treated for an acute episode of hyperkalemia ($K^+$ levels ≥6.0 mmol/L). Fourteen patients were treated with low-dose Na-PSS (15 g once-daily) for a total of 289 months, and this regimen was found to be safe and effective. No episodes of hyperkalemia were recorded while patients were on therapy, but two subjects experienced hypokalemia which resolved when the dose of Na-PSS was reduced. Last, none of the patients developed colonic necrosis or any other life-threatening event that could be attributed to Na-PSS use (Chernin, *Clin. Cardiol.* 2012). Chronic treatment with once-daily Na-PSS was found safe and effective in this study.

While Na-PSS is the current standard of care treatment for potassium reduction in the U.S., the calcium salt of PSS (Ca-PSS) is also commonly used in other parts of the world, including Europe (e.g., Resonium) and Japan. All salt forms of these polymers are poorly tolerated by patients due to a number of compliance-limiting properties, including both GI side effects such as constipation, as well as dosing complexities due to dosing size and frequency, taste and/or texture which contribute to an overall low palatability. The safety and efficacy of PSS has been underexplored (by modern standards) in randomized and controlled clinical trials.

Kayexalate/Na-PSS is also poorly tolerated causing a high incidence of GI side effects including nausea, vomiting, constipation and diarrhea. In addition, Kayexalate is a milled product and consists of irregularly shaped particles ranging in size from about 1-150 μm in size, and has sand-like properties in the human mouth: on ingestion, it gives a strong sensation of foreign matter on the palate and this sensation contributes negatively to patient compliance (Schroder, C. H. *Eur. J. Pediatr.* 1993, 152, 263-264). In total, the physical properties and associated side-effects of Kayexalate lead to poor compliance and render the drug suboptimal for chronic use. Due to these properties, there has been a long felt need to provide an optimal drug for chronic use.

In summary, hyperkalemia is a serious medical condition that can lead to life-threatening arrhythmias and sudden death. Individuals with CKD are at particular risk; however, hyperkalemia can be a comorbidity for individuals with T2DM and CVD, and can also be exacerbated by common medications, especially RAAS inhibitors. The management of hyperkalemia involves the treatment of both acute and chronic increases in serum $K^+$. For example, in an emergency medicine environment, patients can present with significant increases in serum $K^+$ due to comorbidities that cause an acute impairment in the renal excretion of potassium. Examples of chronic hyperkalemia include the recurrent elevations in serum $K^+$ that can occur during the interdialytic interval for patients with ESRD, or the persistent elevations in serum $K^+$ that can occur in CKD patients taking dual RAAS blockade. There is thus a clear need for agents that can be used to treat hyperkalemia. Such agents, suitable for treatment of both acute and chronic hyperkalemia, while being palatable and well-tolerated by the patient, would be advantageous.

SUMMARY OF THE INVENTION

The present invention solves these problems by providing a polymeric binder or a composition containing a polymeric binder than can be given once, twice or three times a day, possesses equivalent or significantly better efficacy, and has physical properties that include a spherical morphology, smaller and more uniform particle size distribution and significantly improved texture—factors that contribute dramatically to improved palatability. These improvements in efficacy (potentially lower doses and/or less frequent dosing) and palatability (better mouth feel, taste, etc.) should increase tolerance, which will improve patient compliance, and hence potassium binding effectiveness.

The cation exchange polymers with low levels of crosslinking described in this invention generally have a higher efficacy for potassium in vivo than resins such as Kayexalate. Surprisingly, approximately 1.4- to 1.5-fold more potassium is excreted fecally than is achieved when, for example, Resonium, with a high level of crosslinking, is similarly dosed (same dosing and fecal collection conditions). The higher potassium capacity of the polymers of this invention may enable the administration of a lower dose of the polymer and meet the long felt need to provide an optimal drug for chronic use in treating hyperkalemia.

In brief, the present invention is directed to compositions and methods for removing potassium from the gastrointestinal track, including methods for treating hyperkalemia, by administration of crosslinked cation exchange polymers with a low level of crosslinking, and a spherical and better controlled particle size distribution, for improved patient tolerance and compliance.

A first aspect of the invention relates to a calcium salt of a crosslinked potassium binding polymer having the structure of Formula (I):

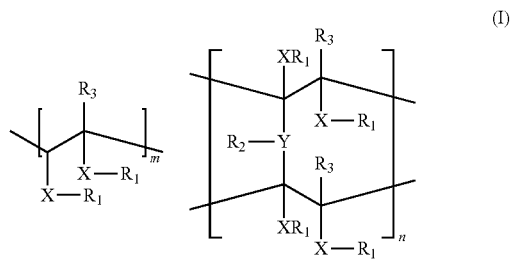

and pharmaceutically acceptable salts thereof,
wherein:
each $R_1$ is independently selected from the group consisting of H, substituted or unsubstituted $(C_1\text{-}C_6)$alkyl, substituted or unsubstituted $(C_6\text{-}C_{18})$aryl, —S(O)$_2$OH, —OS(O)$_2$OH, —C(O)OH, —PO(OH)$_2$, —OP(OH)$_3$, and —NHS(O)$_2$OH;
each $R_2$ is independently selected from the group consisting of H, substituted or unsubstituted $(C_1\text{-}C_6)$alkyl, substituted or unsubstituted $(C_6\text{-}C_{18})$aryl, —S(O)$_2$OH, —OS(O)$_2$OH, —C(O)OH, —PO(OH)$_2$, —OP(OH)$_3$, and —NHS(O)$_2$OH;
each $R_3$ is independently selected from the group consisting of H, halogen, substituted or unsubstituted $(C_1\text{-}C_6)$alkyl, substituted or unsubstituted $(C_6\text{-}C_{18})$aryl, —S(O)$_2$OH, —OS(O)$_2$OH, —C(O)OH, —PO(OH)$_2$, —OP(OH)$_3$, and —NHS(O)$_2$OH;
each X is either absent or independently selected from the group consisting of substituted or unsubstituted $(C_1\text{-}C_6)$alkyl and substituted or unsubstituted $(C_6\text{-}C_{18})$aryl;
each Y is independently selected from the group consisting of substituted or unsubstituted $(C_1\text{-}C_6)$alkyl and substituted or unsubstituted $(C_6\text{-}C_{18})$aryl; and
the mole ratio of m to n is from about 120:1 to about 40:1; and
wherein the crosslinked potassium binding polymer is characterized by a crosslinking of less than 5%.

Another aspect of the invention relates to a calcium salt of a crosslinked potassium binding polymer having the structure of Formula (I):

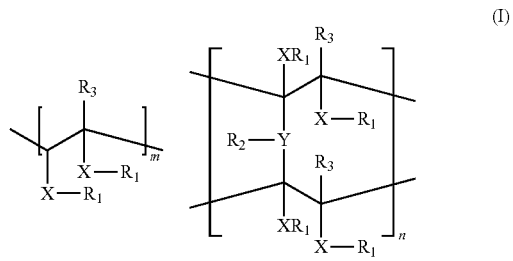

and pharmaceutically acceptable salts thereof,
wherein:
each $R_1$ is independently selected from the group consisting of H, substituted or unsubstituted $(C_1\text{-}C_6)$alkyl, substituted or unsubstituted $(C_6\text{-}C_{18})$aryl, —S(O)$_2$OH, —OS(O)$_2$OH, —C(O)OH, —PO(OH)$_2$, —OP(OH)$_3$, and —NHS(O)$_2$OH;
each $R_2$ is independently selected from the group consisting of H, substituted or unsubstituted $(C_1\text{-}C_6)$alkyl, substituted or unsubstituted $(C_6\text{-}C_{18})$aryl, —S(O)$_2$OH, —OS(O)$_2$OH, —C(O)OH, —PO(OH)$_2$, —OP(OH)$_3$, and —NHS(O)$_2$OH;

each $R_3$ is independently selected from the group consisting of H, halogen, substituted or unsubstituted $(C_1-C_6)$ alkyl, substituted or unsubstituted $(C_6-C_{18})$aryl, —S(O)$_2$OH, —OS(O)$_2$OH, —C(O)OH, —PO(OH)$_2$, —OP(OH)$_3$, and —NHS(O)$_2$OH;

each X is either absent or independently selected from the group consisting of substituted or unsubstituted $(C_1-C_6)$alkyl and substituted or unsubstituted $(C_6-C_{18})$aryl;

each Y is independently selected from the group consisting of substituted or unsubstituted $(C_1-C_6)$alkyl and substituted or unsubstituted $(C_6-C_{18})$aryl; and the mole ratio of m to n is from about 120:1 to about 40:1; and wherein the crosslinked potassium binding polymer comprises substantially spherical particles having a median diameter from about 5 μm to about 130 μm and wherein the crosslinked potassium binding polymer is characterized by a crosslinking of about 1.8%, wherein the term about means ±10%.

Another aspect of the invention relates to a calcium salt of a crosslinked potassium binding polymer having the structure of Formula (I):

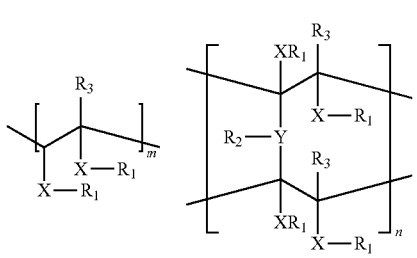

and pharmaceutically acceptable salts thereof, wherein:

each $R_1$ is independently selected from the group consisting of H, substituted or unsubstituted $(C_1-C_6)$alkyl, substituted or unsubstituted $(C_6-C_{18})$aryl, —S(O)$_2$OH, —OS(O)$_2$OH, —C(O)OH, —PO(OH)$_2$, —OP(OH)$_3$, and —NHS(O)$_2$OH;

each $R_2$ is independently selected from the group consisting of H, substituted or unsubstituted $(C_1-C_6)$alkyl, substituted or unsubstituted $(C_6-C_{18})$aryl, —S(O)$_2$OH, —OS(O)$_2$OH, —C(O)OH, —PO(OH)$_2$, —OP(OH)$_3$, and —NHS(O)$_2$OH;

each $R_3$ is independently selected from the group consisting of H, halogen, substituted or unsubstituted $(C_1-C_6)$ alkyl, substituted or unsubstituted $(C_6-C_{18})$aryl, —S(O)$_2$OH, —OS(O)$_2$OH, —C(O)OH, —PO(OH)$_2$, —OP(OH)$_3$, and —NHS(O)$_2$OH;

each X is either absent or independently selected from the group consisting of substituted or unsubstituted $(C_1-C_6)$alkyl and substituted or unsubstituted $(C_6-C_{18})$aryl;

each Y is independently selected from the group consisting of substituted or unsubstituted $(C_1-C_6)$alkyl and substituted or unsubstituted $(C_6-C_{18})$aryl; and the mole ratio of m to n is from about 120:1 to about 40:1; and wherein the crosslinked potassium binding polymer comprises substantially spherical particles having a median diameter from about 25 μm to about 125 μm and wherein the crosslinked potassium binding polymer is characterized by a crosslinking of about 1.8%, wherein the term about means ±10%.

Another aspect of the invention relates to a calcium salt of a crosslinked potassium binding polymer having the structure of Formula (I):

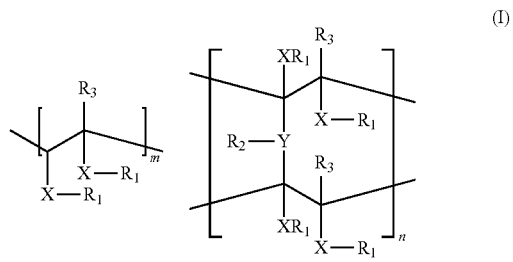

and pharmaceutically acceptable salts thereof, wherein:

each $R_1$ is independently selected from the group consisting of H, substituted or unsubstituted $(C_1-C_6)$alkyl, substituted or unsubstituted $(C_6-C_{18})$aryl, —S(O)$_2$OH, —OS(O)$_2$OH, —C(O)OH, —PO(OH)$_2$, —OP(OH)$_3$, and —NHS(O)$_2$OH;

each $R_2$ is independently selected from the group consisting of H, substituted or unsubstituted $(C_1-C_6)$alkyl, substituted or unsubstituted $(C_6-C_{18})$aryl, —S(O)$_2$OH, —OS(O)$_2$OH, —C(O)OH, —PO(OH)$_2$, —OP(OH)$_3$, and —NHS(O)$_2$OH;

each $R_3$ is independently selected from the group consisting of H, halogen, substituted or unsubstituted $(C_1-C_6)$ alkyl, substituted or unsubstituted $(C_6-C_{18})$aryl, —S(O)$_2$OH, —OS(O)$_2$OH, —C(O)OH, —PO(OH)$_2$, —OP(OH)$_3$, and —NHS(O)$_2$OH;

each X is either absent or independently selected from the group consisting of substituted or unsubstituted $(C_1-C_6)$alkyl and substituted or unsubstituted $(C_6-C_{18})$aryl;

each Y is independently selected from the group consisting of substituted or unsubstituted $(C_1-C_6)$alkyl and substituted or unsubstituted $(C_6-C_{18})$aryl; and the mole ratio of m to n is from about 120:1 to about 40:1; and wherein the crosslinked potassium binding polymer comprises substantially spherical particles having a median diameter from about 5 μm to about 70 μm and wherein the crosslinked potassium binding polymer is characterized by a crosslinking of about 1.8%, wherein the term about means ±10%.

Another aspect of the invention relates to a calcium salt of a crosslinked potassium binding polymer having the structure of Formula (I):

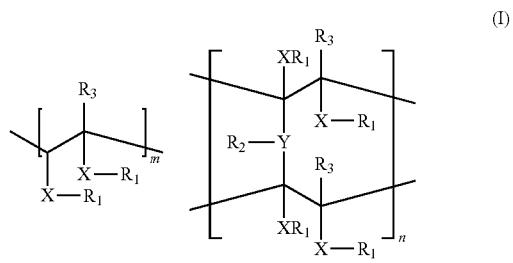

and pharmaceutically acceptable salts thereof, wherein:
each $R_1$ is independently selected from the group consisting of H, substituted or unsubstituted $(C_1$-$C_6)$alkyl, substituted or unsubstituted $(C_6$-$C_{18})$aryl, —S(O)$_2$OH, —OS(O)$_2$OH, —C(O)OH, —PO(OH)$_2$, —OP(OH)$_3$, and —NHS(O)$_2$OH;

each $R_2$ is independently selected from the group consisting of H, substituted or unsubstituted $(C_1$-$C_6)$alkyl, substituted or unsubstituted $(C_6$-$C_{18})$aryl, —S(O)$_2$OH, —OS(O)$_2$OH, —C(O)OH, —PO(OH)$_2$, —OP(OH)$_3$, and —NHS(O)$_2$OH;

each $R_3$ is independently selected from the group consisting of H, halogen, substituted or unsubstituted $(C_1$-$C_6)$ alkyl, substituted or unsubstituted $(C_6$-$C_{18})$aryl, —S(O)$_2$OH, —OS(O)$_2$OH, —C(O)OH, —PO(OH)$_2$, —OP(OH)$_3$, and —NHS(O)$_2$OH;

each X is either absent or independently selected from the group consisting of substituted or unsubstituted $(C_1$-$C_6)$alkyl and substituted or unsubstituted $(C_6$-$C_{18})$aryl;

each Y is independently selected from the group consisting of substituted or unsubstituted $(C_1$-$C_6)$alkyl and substituted or unsubstituted $(C_6$-$C_{18})$aryl; and the mole ratio of m to n is from about 120:1 to about 40:1; and wherein the crosslinked potassium binding polymer comprises substantially spherical particles having a median diameter from about 20 μm to about 130 μm, wherein the potassium binding polymer has a Mouth Feel score greater than 3.5, and wherein the crosslinked potassium binding polymer is characterized by a crosslinking of about 1.8%, wherein the term about means ±10%.

Another aspect of the invention relates to a calcium salt of a crosslinked potassium binding polymer having the structure of Formula (I):

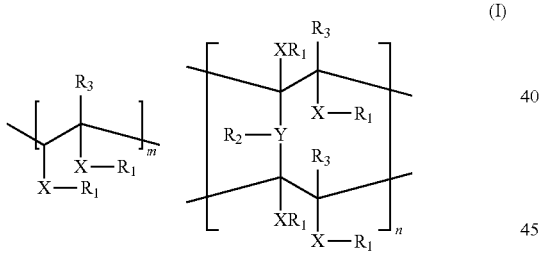

and pharmaceutically acceptable salts thereof,
wherein:
each $R_1$ is independently selected from the group consisting of H, substituted or unsubstituted $(C_1$-$C_6)$alkyl, substituted or unsubstituted $(C_6$-$C_{18})$aryl, —S(O)$_2$OH, —OS(O)$_2$OH, —C(O)OH, —PO(OH)$_2$, —OP(OH)$_3$, and —NHS(O)$_2$OH;

each $R_2$ is independently selected from the group consisting of H, substituted or unsubstituted $(C_1$-$C_6)$alkyl, substituted or unsubstituted $(C_6$-$C_{18})$aryl, —S(O)$_2$OH, —OS(O)$_2$OH, —C(O)OH, —PO(OH)$_2$, —OP(OH)$_3$, and —NHS(O)$_2$OH;

each $R_3$ is independently selected from the group consisting of H, halogen, substituted or unsubstituted $(C_1$-$C_6)$ alkyl, substituted or unsubstituted $(C_6$-$C_{18})$aryl, —S(O)$_2$OH, —OS(O)$_2$OH, —C(O)OH, —PO(OH)$_2$, —OP(OH)$_3$, and —NHS(O)$_2$OH;

each X is either absent or independently selected from the group consisting of substituted or unsubstituted $(C_1$-$C_6)$alkyl and substituted or unsubstituted $(C_6$-$C_{18})$aryl;

each Y is independently selected from the group consisting of substituted or unsubstituted $(C_1$-$C_6)$alkyl and substituted or unsubstituted $(C_6$-$C_{18})$aryl; and the mole ratio of m to n is from about 120:1 to about 40:1; and wherein the crosslinked potassium binding polymer comprises substantially spherical particles having a median diameter from about 5 μm to about 70 μm, wherein the potassium binding polymer has a Mouth Feel score greater than 3.5, and wherein the crosslinked potassium binding polymer is characterized by a crosslinking of about 1.8%, wherein the term about means ±10%.

Another aspect of the invention relates to a calcium salt of a crosslinked potassium binding polymer having the structure of Formula (I):

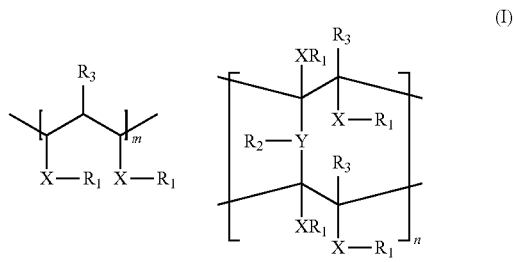

and pharmaceutically acceptable salts thereof,
wherein:
each $R_1$ is independently selected from the group consisting of H, —S(O)$_2$OH, —OS(O)$_2$OH, —C(O)OH, —PO(OH)$_2$, —OP(OH)$_3$, and —NHS(O)$_2$OH;

each $R_2$ is independently selected from the group consisting of H, substituted or unsubstituted $(C_1$-$C_6)$alkyl, substituted or unsubstituted $(C_6$-$C_{18})$aryl, —S(O)$_2$OH, —OS(O)$_2$OH, —C(O)OH, —PO(OH)$_2$, —OP(OH)$_3$, and —NHS(O)$_2$OH;

each $R_3$ is H;
each X is either absent or substituted or unsubstituted $(C_6$-$C_{18})$aryl;
each Y is independently selected from the group consisting of substituted or unsubstituted $(C_1$-$C_6)$alkyl and substituted or unsubstituted $(C_6$-$C_{18})$aryl; and the mole ratio of m to n is from about 120:1 to about 40:1; and wherein the crosslinked potassium binding polymer comprises substantially spherical particles having a median diameter from about 20 μm to about 130 μm and wherein the crosslinked potassium binding polymer is characterized by a crosslinking of about 1.8%, wherein the term about means ±10%.

Another aspect of the invention relates to a calcium salt of a crosslinked potassium binding polymer having the structure of Formula (I):

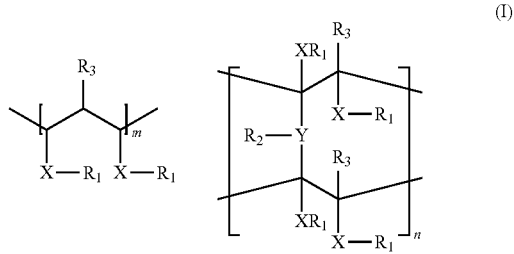

and pharmaceutically acceptable salts thereof,
wherein:
each $R_1$ is independently selected from the group consisting of H, —S(O)$_2$OH, —OS(O)$_2$OH, —C(O)OH, —PO(OH)$_2$, —OP(OH)$_3$, and —NHS(O)$_2$OH;
each $R_2$ is independently selected from the group consisting of H, substituted or unsubstituted ($C_1$-$C_6$)alkyl, substituted or unsubstituted ($C_6$-$C_{18}$)aryl, —S(O)$_2$OH, —OS(O)$_2$OH, —C(O)OH, —PO(OH)$_2$, —OP(OH)$_3$, and —NHS(O)$_2$OH;
each $R_3$ is H;
each X is either absent or substituted or unsubstituted ($C_6$-$C_{18}$)aryl;
each Y is independently selected from the group consisting of substituted or unsubstituted ($C_1$-$C_6$)alkyl and substituted or unsubstituted ($C_6$-$C_{18}$)aryl; and
the mole ratio of m to n is from about 120:1 to about 40:1; and
wherein the crosslinked potassium binding polymer comprises substantially spherical particles having a median diameter from about 5 µm to about 70 µm and wherein the crosslinked potassium binding polymer is characterized by a crosslinking of about 1.8%, wherein the term about means ±10%.

Another aspect of the invention relates to a pharmaceutical composition comprising a crosslinked potassium binding polymer of Formula (I) and a pharmaceutically acceptable carrier, diluent, or excipient.

Another aspect of the invention relates to a pharmaceutical composition comprising a calcium salt of a crosslinked potassium binding polymer that has a potassium exchange capacity from about 1 mEq to about 4 mEq per gram of potassium binding polymer and a pharmaceutically acceptable carrier, diluent, or excipient, wherein the potassium binding polymer is characterized by a swelling ratio in water of between about 3 grams of water per gram of polymer to about 8 grams of water per gram of polymer and a crosslinking of less than 5% and wherein the polymer comprises substantially spherical particles and is substantially endotoxin free.

Another aspect of the invention relates to a pharmaceutical composition comprising a calcium salt of a crosslinked potassium binding polymer that has a potassium exchange capacity from about 1 mEq to about 4 mEq per gram of potassium binding polymer and a pharmaceutically acceptable carrier, diluent, or excipient, wherein the potassium binding polymer is characterized by a swelling ratio in water of between about 3 grams of water per gram of polymer to about 8 grams of water per gram of polymer and a crosslinking of less than 5%.

Another aspect of the invention relates to a pharmaceutical composition comprising a calcium salt of a crosslinked potassium binding polymer that has a potassium exchange capacity from about 1 mEq to about 4 mEq per gram of potassium binding polymer and a pharmaceutically acceptable carrier, diluent, or excipient, wherein the potassium binding polymer is characterized by a crosslinking of less than 5% and a swelling ratio in water of between about 3 grams of water per gram of polymer to about 8 grams of water per gram of polymer.

Another aspect of the invention relates to a pharmaceutical composition comprising a calcium salt of a crosslinked potassium binding polymer that has a potassium exchange capacity from about 1 mEq to about 4 mEq per gram of potassium binding polymer and a pharmaceutically acceptable carrier, diluent, or excipient, wherein the potassium binding polymer is characterized by a crosslinking of less than 5% and wherein median diameter is from about 1 µm to about 130 µm when said particles are in their calcium salt form and swollen in water.

Another aspect of the invention relates to a pharmaceutical composition comprising a calcium salt of a crosslinked potassium binding polymer and a pharmaceutically acceptable carrier, diluent, or excipient, wherein the crosslinked potassium binding polymer is characterized by a crosslinking of less than 5% and wherein median diameter is from about 1 µm to about 130 µm when said particles are in their calcium salt form and swollen in water.

Another aspect of the invention relates to a method for removing potassium from the gastrointestinal tract of a patient showing clinical signs of hyperkalemia or suspected of having hyperkalemia. The method comprises administering a calcium salt of a crosslinked potassium binding polymer, or salt thereof, to the patient, wherein the potassium binding polymer comprises at least one monomer and one crosslinker, the crosslinker comprising from about 1 mole % to about 3 mole % of the potassium binding polymer and wherein the potassium binding polymer is characterized by a crosslinking of less than 5%.

Another aspect of the invention relates to a method for removing potassium from the gastrointestinal tract of a patient showing clinical signs of hyperkalemia or suspected of having hyperkalemia. The method comprises administering a calcium salt of a crosslinked potassium binding polymer, or salt thereof, to the patient, wherein the potassium binding polymer comprises at least one monomer and one crosslinker, wherein the potassium binding polymer comprises substantially spherical particles having a median diameter from about 1 µm to about 25 µm, and wherein the crosslinked potassium binding polymer is characterized by a crosslinking of less than 5%.

Another aspect of the invention relates to a method for removing potassium from the gastrointestinal tract of a patient showing clinical signs of hyperkalemia or suspected of having hyperkalemia. The method comprises administering of a calcium salt of a potassium binding polymer, or salt thereof, to the patient, wherein the crosslinked potassium binding polymer has a structure of Formula (I):

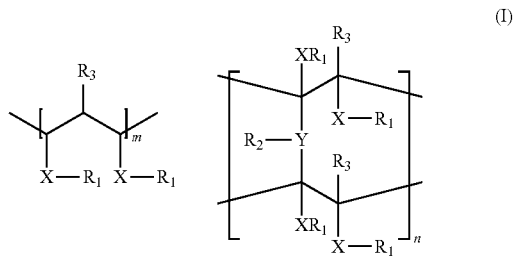

and pharmaceutically acceptable salts thereof,
wherein:
each $R_1$ is independently selected from the group consisting of H, substituted or unsubstituted ($C_1$-$C_6$) alkyl, substituted or unsubstituted ($C_6$-$C_{18}$) aryl, —S(O)$_2$OH, —OS(O)$_2$OH, —C(O)OH, —PO(OH)$_2$, —OP(OH)$_3$, and —NHS(O)$_2$OH;
each $R_2$ is independently selected from the group consisting of H, substituted or unsubstituted ($C_1$-$C_6$)alkyl, substituted or unsubstituted ($C_6$-$C_{18}$)aryl, —S(O)$_2$OH, —OS(O)$_2$OH, —C(O)OH, —PO(OH)$_2$, —OP(OH)$_3$, and —NHS(O)$_2$OH;

each $R_3$ is independently selected from the group consisting of H, halogen, substituted or unsubstituted ($C_1$-$C_6$) alkyl, substituted or unsubstituted ($C_6$-$C_{18}$)aryl, —S(O)$_2$OH, —OS(O)$_2$OH, —C(O)OH, —PO(OH)$_2$, —OP(OH)$_3$, and —NHS(O)$_2$OH;

each X is either absent or independently selected from the group consisting of substituted or unsubstituted ($C_1$-$C_6$)alkyl and substituted or unsubstituted ($C_6$-$C_{18}$)aryl;

each Y is independently selected from the group consisting of substituted or unsubstituted ($C_1$-$C_6$)alkyl and substituted or unsubstituted ($C_6$-$C_{18}$)aryl; and the mole ratio of m to n is from about 120:1 to about 40:1;

wherein the crosslinked potassium binding polymer is characterized by a crosslinking of less than 5%.

Another aspect of the invention relates to a method for removing potassium from the gastrointestinal tract of a patient showing clinical signs of hyperkalemia or suspected of having hyperkalemia is provided, the method comprising administering a calcium salt of crosslinked potassium binding polymer, or salt thereof, to the patient, wherein the crosslinked potassium binding polymer comprises at least one monomer and one crosslinker, the crosslinker comprising from about 1 wt. % to about 3 wt. % of the potassium binding polymer. In some embodiments, the crosslinker comprises from about 1 mole % to about 4 mole % of the potassium binding polymer.

Another aspect of the invention relates to a method for removing potassium from the gastrointestinal tract of a patient showing clinical signs of hyperkalemia or suspected of having hyperkalemia is provided, the method comprising administering a calcium salt of crosslinked potassium binding polymer, or salt thereof, to the patient, wherein the potassium binding polymer comprises substantially spherical particles having a median diameter from about 1 μm to about 200 μm.

Another aspect of the invention relates to a method for removing potassium from the gastrointestinal tract of a patient showing clinical signs of hyperkalemia or suspected of having hyperkalemia is provided, the method comprising administering a calcium salt of crosslinked potassium binding polymer, or salt thereof, to the patient, wherein the crosslinked potassium binding polymer has a structure of Formula (I):

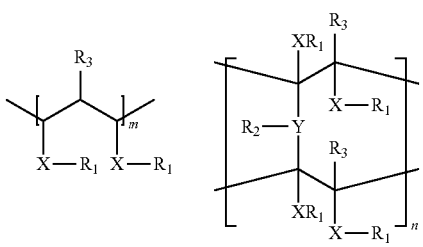

(I)

and pharmaceutically acceptable salts thereof,
wherein:
each $R_1$ is independently selected from the group consisting of H, substituted or unsubstituted ($C_1$-$C_6$)alkyl, substituted or unsubstituted ($C_6$-$C_{18}$)aryl, —S(O)$_2$OH, —OS(O)$_2$OH, —C(O)OH, —PO(OH)$_2$, —OP(OH)$_3$, and —NHS(O)$_2$OH;

each $R_2$ is independently selected from the group consisting of H, substituted or unsubstituted ($C_1$-$C_6$)alkyl, substituted or unsubstituted ($C_6$-$C_{18}$)aryl, —S(O)$_2$OH, —OS(O)$_2$OH, —C(O)OH, —PO(OH)$_2$, —OP(OH)$_3$, and —NHS(O)$_2$OH;

each $R_3$ is independently selected from the group consisting of H, halogen, substituted or unsubstituted ($C_1$-$C_6$) alkyl, substituted or unsubstituted ($C_6$-$C_{18}$)aryl, —S(O)$_2$OH, —OS(O)$_2$OH, —C(O)OH, —PO(OH)$_2$, —OP(OH)$_3$, and —NHS(O)$_2$OH;

each X is either absent or independently selected from the group consisting of substituted or unsubstituted ($C_1$-$C_6$)alkyl and substituted or unsubstituted ($C_6$-$C_{18}$)aryl;

each Y is a divalent group; and the ratio of m to n is from about 120:1 to about 40:1 wherein the crosslinked potassium binding polymer is characterized by a crosslinking of less than 5%.

Another aspect of the invention relates to a calcium salt of crosslinked potassium binding polymer having the structure of Formula (I):

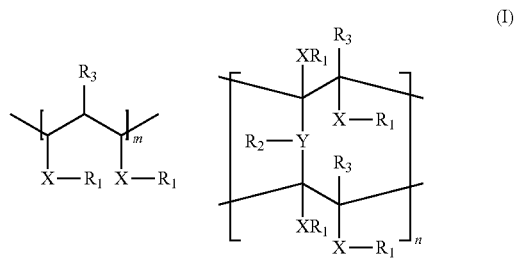

(I)

and pharmaceutically acceptable salts thereof,
wherein:
each $R_1$ is independently selected from the group consisting of H, substituted or unsubstituted ($C_1$-$C_6$)alkyl, substituted or unsubstituted ($C_6$-$C_{18}$)aryl, —S(O)$_2$OH, —OS(O)$_2$OH, —C(O)OH, —PO(OH)$_2$, —OP(OH)$_3$, and —NHS(O)$_2$OH;

each $R_2$ is independently selected from the group consisting of H, substituted or unsubstituted ($C_1$-$C_6$)alkyl, substituted or unsubstituted ($C_6$-$C_{18}$)aryl, —S(O)$_2$OH, —OS(O)$_2$OH, —C(O)OH, —PO(OH)$_2$, —OP(OH)$_3$, and —NHS(O)$_2$OH;

each $R_3$ is independently selected from the group consisting of H, halogen, substituted or unsubstituted ($C_1$-$C_6$) alkyl, substituted or unsubstituted ($C_6$-$C_{18}$)aryl, —S(O)$_2$OH, —OS(O)$_2$OH, —C(O)OH, —PO(OH)$_2$, —OP(OH)$_3$, and —NHS(O)$_2$OH;

each X is either absent or independently selected from the group consisting of substituted or unsubstituted ($C_1$-$C_6$)alkyl and substituted or unsubstituted ($C_6$-$C_{18}$)aryl;

each Y is a divalent group; and the ratio of m to n is from about 120:1 to about 40:1;

wherein the crosslinked potassium binding polymer is characterized by a crosslinking of less than 5%.

Another aspect of the invention relates to a pharmaceutical composition comprising a calcium salt of crosslinked potassium binding polymer having the structure of Formula (I):

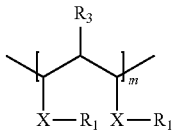 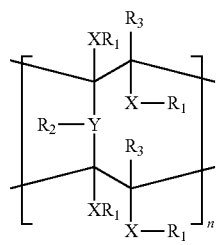 (I)

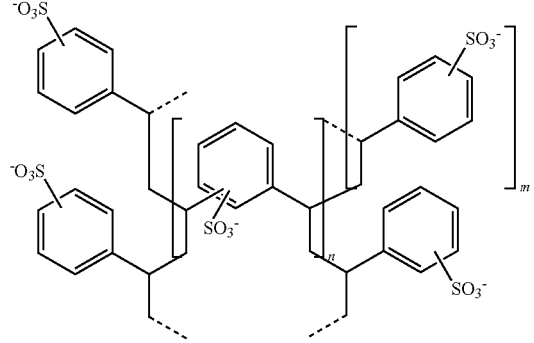

and pharmaceutically acceptable salts thereof,
wherein:
each $R_1$ is independently selected from the group consisting of H, substituted or unsubstituted $(C_1-C_6)$alkyl, substituted or unsubstituted $(C_6-C_{18})$aryl, —S(O)$_2$OH, —OS(O)$_2$OH, —C(O)OH, —PO(OH)$_2$, —OP(OH)$_3$, and —NHS(O)$_2$OH;
each $R_2$ is independently selected from the group consisting of H, substituted or unsubstituted $(C_1-C_6)$alkyl, substituted or unsubstituted $(C_6-C_{18})$aryl, —S(O)$_2$OH, —OS(O)$_2$OH, —C(O)OH, —PO(OH)$_2$, —OP(OH)$_3$, and —NHS(O)$_2$OH;
each $R_3$ is independently selected from the group consisting of H, halogen, substituted or unsubstituted $(C_1-C_6)$ alkyl, substituted or unsubstituted $(C_6-C_{18})$aryl, —S(O)$_2$OH, —OS(O)$_2$OH, —C(O)OH, —PO(OH)$_2$, —OP(OH)$_3$, and —NHS(O)$_2$OH;
each X is either absent or independently selected from the group consisting of substituted or unsubstituted $(C_1-C_6)$alkyl and substituted or unsubstituted $(C_6-C_{18})$aryl;
each Y is a divalent group; and
the ratio of m to n is from about 120:1 to about 40:1;
wherein the crosslinked potassium binding polymer is characterized by a crosslinking of less than 5%; and
a pharmaceutically acceptable carrier, diluent, or excipient.

Another aspect of the invention relates to a calcium salt of crosslinked potassium binding polymer having the following structure:

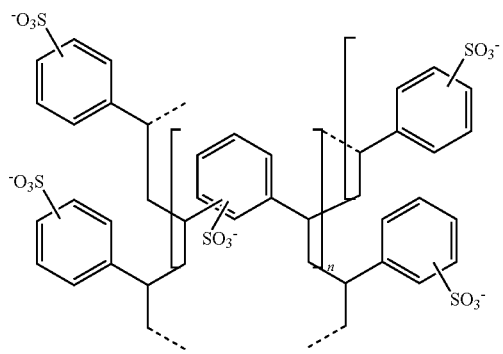

and pharmaceutically acceptable salts thereof,
wherein the mole ratio of m to n is from about 120:1 to about 40:1; and
wherein the crosslinked potassium binding polymer is characterized by a crosslinking of less than 5%.

Another aspect of the invention relates to a pharmaceutical composition comprising:
i) about 86.5% to about 91% of a calcium salt of a crosslinked potassium binding polymer having the following structure:

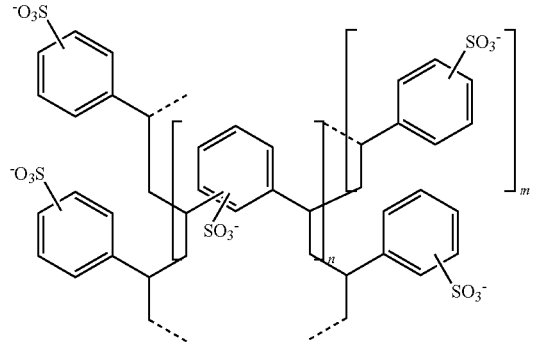

and pharmaceutically acceptable salts thereof,
wherein the mole ratio of m to n is from about 120:1 to about 40:1; and
wherein the crosslinked potassium binding polymer is characterized by a crosslinking of less than 5%;
ii) about 2.0% to about 3.0% of calcium citrate tetrahydrate;
iii) about 2.0% to about 3.0% of anhydrous citric acid;
iv) about 0.1% to about 1.0% of sucralose;
v) about 2.0% to about 3.0% of artificial orange flavored powder; and
vi) about 2.5% to about 3.5% of methyl cellulose A4C.

Another aspect of the invention relates to a pharmaceutical composition comprising:
i) about 86.5% to about 91% of a calcium salt of a crosslinked potassium binding polymer of Formula (I) and pharmaceutically acceptable salts thereof;
ii) about 2.0% to about 3.0% of calcium citrate tetrahydrate;
iii) about 2.0% to about 3.0% of anhydrous citric acid;
iv) about 0.1% to about 1% of sucralose;
v) about 2.0% to about 3.0% of artificial orange flavored powder; and
vi) about 2.5% to about 3.5% of methyl cellulose A4C.

Another aspect of the invention relates to a pharmaceutical composition comprising:
i) about 89% to about 94.5% of a calcium salt of a crosslinked potassium binding polymer having the following structure:

and pharmaceutically acceptable salts thereof,
wherein the mole ratio of m to n is from about 120:1 to about 40:1; and
wherein the crosslinked potassium binding polymer is characterized by a crosslinking of less than 5%;

ii) about 0.6% to about 1.6% of calcium citrate tetrahydrate;
iii) about 0.02% to about 0.5% of anhydrous citric acid;
iv) about 0.1% to about 1% of sucralose;
v) about 0.6% to about 1.6% of vanillin powder;
vi) about 2.5% to about 3.5% of methyl cellulose A4C; and
vii) about 1.6% to about 2.6% of titanium dioxide.

Another aspect of the invention relates to a pharmaceutical composition comprising:
i) about 89% to about 94.5% of a calcium salt of a crosslinked potassium binding polymer of Formula (I) and pharmaceutically acceptable salts thereof;
ii) about 0.6% to about 1.6% of calcium citrate tetrahydrate;
iii) about 0.02% to about 0.5% of anhydrous citric acid;
iv) about 0.1% to about 1% of sucralose;
v) about 0.6% to about 1.6% of vanillin powder;
vi) about 2.5% to about 3.5% of methyl cellulose A4C; and
vii) about 1.6% to about 2.6% of titanium dioxide.

Another aspect of the invention relates to a pharmaceutical composition comprising:
i) about 10% to about 26% of a calcium salt of a crosslinked potassium binding polymer having the following structure:

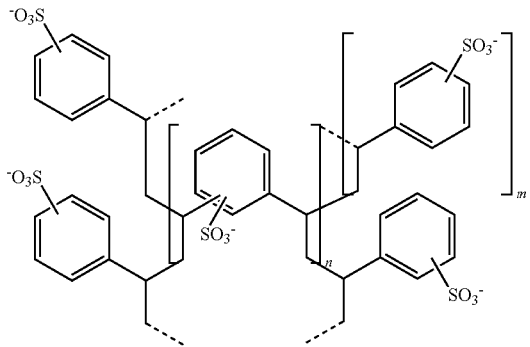

and pharmaceutically acceptable salts thereof,
wherein the mole ratio of m to n is from about 120:1 to about 40:1; and
wherein the crosslinked potassium binding polymer is characterized by a crosslinking of less than 5%;
ii) about 0.1% to about 1.0% of calcium citrate tetrahydrate;
iii) about 0.015% to about 0.15% of benzoic acid;
iv) about 0.1% to about 1% of anhydrous citric acid;
v) about 0.015% to about 0.15% of sucralose;
vi) about 0.1% to about 1.0% of natural orange WONF FV7466;
vii) about 0.1% to about 1.0% of xanthan gum cp; and
viii) about 73.7% to about 85.57% of water.

Another aspect of the invention relates to a pharmaceutical composition comprising:
i) about 10% to about 26% of a calcium salt of a crosslinked potassium binding polymer of Formula (I) and pharmaceutically acceptable salts thereof;
ii) about 0.1% to about 1.0% of calcium citrate tetrahydrate;
iii) about 0.015% to about 0.15% of benzoic acid;
iv) about 0.1% to about 1% of anhydrous citric acid;
v) about 0.015% to about 0.15% of sucralose;
vi) about 0.1% to about 1.0% of natural orange WONF FV7466;
vii) about 0.1% to about 1.0% of xanthan gum cp; and
viii) about 73.7% to about 85.57% of water.

Another aspect of the invention relates to a pharmaceutical composition comprising:
i) about 10% to about 26% of a calcium salt of a crosslinked potassium binding polymer having the following structure:

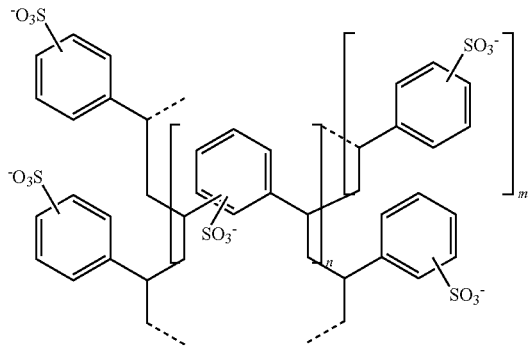

and pharmaceutically acceptable salts thereof,
wherein the mole ratio of m to n is from about 120:1 to about 40:1; and
wherein the crosslinked potassium binding polymer is characterized by a crosslinking of less than 5%;
ii) about 0.01% to about 0.5% of calcium citrate tetrahydrate;
iii) about 0.01% to about 0.1% of sorbic acid;
iv) about 0.001% to about 0.1% of anhydrous citric acid;
v) about 0.05% to about 0.15% of sucralose;
vi) about 0.1% to about 1.0% of SuperVan art vanilla VM36;
vii) about 0.1% to about 1.0% of xanthan gum cp;
viii) about 0.1% to about 1.0% of titanium dioxide; and
ix) about 73.2% to about 86.65% of water.

Another aspect of the invention relates to a pharmaceutical composition comprising:
i) about 10% to about 26% of a calcium salt of a crosslinked potassium binding polymer of Formula (I) and pharmaceutically acceptable salts thereof;
ii) about 0.01% to about 0.5% of calcium citrate tetrahydrate;
iii) about 0.01% to about 0.1% of sorbic acid;
iv) about 0.001% to about 0.1% of anhydrous citric acid;
v) about 0.05% to about 0.15% of sucralose;
vi) about 0.1% to about 1.0% of SuperVan art vanilla VM36;
vii) about 0.1% to about 1.0% of xanthan gum cp;
viii) about 0.1% to about 1.0% of titanium dioxide; and
ix) about 73.2% to about 86.65% of water.

BRIEF DESCRIPTION OF THE DRAWINGS

FIG. 12: shows the relationship between DVB weight percent, DVB mole percent, and styrene:DVB ratio for crosslinked polystyrene.

DETAILED DESCRIPTION OF THE INVENTION

Figure 1:
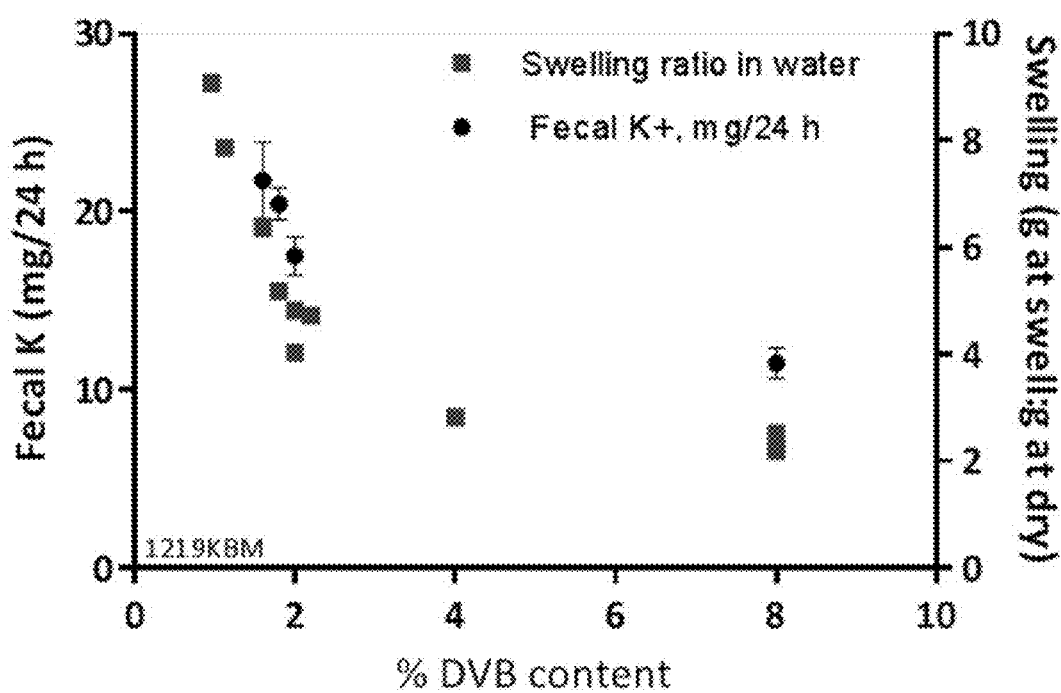
FIG. 1: shows the swelling ratio of calcium polystyrene sulfonate resins in water as well as the observed fecal potassium excretion from rodents orally dosed with selected resins.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs.

Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs. The initial definition provided for a group or term provided in this disclosure applies to that group or term throughout the present disclosure individually or as part of another group, unless otherwise indicated.

A first aspect of the invention relates to a calcium salt of a crosslinked potassium binding polymer having the structure of Formula (I):

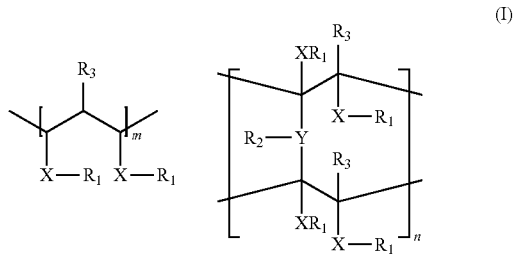

and pharmaceutically acceptable salts thereof,
wherein:
$R_1$, $R_2$, $R_3$, X, Y, m, and n are as defined above; and
wherein the crosslinked potassium binding polymer is characterized by a crosslinking of less than 5%.

In some embodiments, $R_1$ is selected from the group consisting of H, substituted or unsubstituted $(C_1-C_6)$alkyl, substituted or unsubstituted $(C_6-C_{18})$aryl, or —$S(O)_2OH$. In another embodiment, $R_1$ is H and —$S(O)_2OH$.

In some embodiments, $R_2$ is selected from the group consisting of H, substituted or unsubstituted $(C_1-C_6)$alkyl, substituted or unsubstituted $(C_6-C_{18})$aryl, or —$S(O)_2OH$. In another embodiment, $R_2$ is H or —$S(O)_2OH$.

In some embodiments, $R_3$ is selected from the group consisting of H, halogen, substituted or unsubstituted $(C_1-C_6)$alkyl, substituted or unsubstituted $(C_6-C_{18})$aryl, and —$S(O)_2OH$. In another embodiment, $R_3$ is H or phenyl. In yet another embodiment, $R_3$ is H.

In some embodiments, X is either absent. In another embodiment, X is selected from the group consisting of substituted or unsubstituted $(C_1-C_6)$alkyl and substituted or unsubstituted $(C_6-C_{18})$aryl. In yet another embodiment, X is absent or substituted or unsubstituted $(C_6-C_{18})$aryl. In yet another embodiment, X is absent or unsubstituted $(C_6-C_{18})$aryl. In another embodiment, X is absent or phenyl. In yet another embodiment, X is absent and $R_1$ is H when $XR_1$ is attached to the carbon atom substituted with Y.

In some embodiments, Y is selected from the group consisting of substituted or unsubstituted $(C_1-C_6)$alkyl and substituted or unsubstituted $(C_6-C_{18})$aryl. In another embodiment, Y is substituted or unsubstituted $(C_6-C_{18})$aryl. In another embodiment, Y is unsubstituted $(C_6-C_{18})$aryl. In yet another embodiment, Y is phenyl.

In some embodiments, the mole ratio of m to n is from about 120:1 to about 40:1. In another embodiment, the ratio of m to n is from about 70:1 to about 50:1. In yet another embodiment, the ratio of m to n is from about 70:1 to about 60:1. In another embodiment, the ratio of m to n is about 68:1.

In some embodiments, the polymer is a styrene polymer. In another embodiment, the polymer is crosslinked with divinyl benzene. In yet another embodiment, the divinyl benzene is divinyl benzene sulfonate. In another embodiment, the polymer is a salt of crosslinked polystyrene sulfonate. In yet another embodiment, the composition is further substantially active as a phosphate binder. In another embodiment, the patient is experiencing hyperkalemia. In yet another embodiment, the polymer has a capacity to increase fecal phosphorous output in a subject. In another embodiment, the polymer has a capacity to decrease urinary phosphorous output in a subject.

In another aspect, the present invention relates to a pharmaceutical composition comprising a calcium salt of a crosslinked potassium binding polymer that has a potassium exchange capacity from about 1 mEq to about 4 mEq per gram of potassium binding polymer and a pharmaceutically acceptable carrier, diluent, or excipient, wherein the potassium binding polymer is characterized by a swelling ratio in water of between about 3 grams of water per gram of polymer to about 8 grams of water per gram of polymer and a crosslinking of less than 5% and wherein the polymer comprises substantially spherical particles and is substantially endotoxin free. In some embodiments, the polymer is a styrene polymer. In another embodiment, the polymer is crosslinked with divinyl benzene. In yet another embodiment, the divinyl benzene is divinyl benzene sulfonate. In another embodiment, the polymer is a salt of crosslinked polystyrene sulfonate. In yet another embodiment, the composition is further substantially active as a phosphate binder. In another embodiment, the patient is experiencing hyperkalemia. In yet another embodiment, the polymer has a capacity to increase fecal phosphorous output in a subject. In another embodiment, the polymer has a capacity to decrease urinary phosphorous output in a subject.

Another aspect of the invention relates to a pharmaceutical composition comprising a calcium salt of a crosslinked potassium binding polymer that has a potassium exchange capacity from about 1 mEq to about 4 mEq per gram of potassium binding polymer and a pharmaceutically acceptable carrier, diluent, or excipient, wherein the potassium binding polymer is characterized by a swelling ratio in water of between about 3 grams of water per gram of polymer to about 8 grams of water per gram of polymer and a crosslinking of less than 5%. In some embodiments, the polymer is a styrene polymer. In another embodiment, the polymer is crosslinked with divinyl benzene. In yet another embodiment, the divinyl benzene is divinyl benzene sulfonate. In another embodiment, the polymer is a salt of crosslinked polystyrene sulfonate. In yet another embodiment, the composition is further substantially active as a phosphate binder. In another embodiment, the patient is experiencing hyperkalemia. In yet another embodiment, the polymer has a capacity to increase fecal phosphorous output in a subject. In another embodiment, the polymer has a capacity to decrease urinary phosphorous output in a subject.

In another aspect, the present invention relates to a pharmaceutical composition comprising a calcium salt of a crosslinked potassium binding polymer that has a potassium exchange capacity from about 1 mEq to about 4 mEq per gram of potassium binding polymer and a pharmaceutically acceptable carrier, diluent, or excipient, wherein the potassium binding polymer is characterized by a crosslinking of less than 5% and a swelling ratio in water of between about 3 grams of water per gram of polymer to about 8 grams of water per gram of polymer. In some embodiments, the polymer is a styrene polymer. In another embodiment, the polymer is crosslinked with divinyl benzene. In yet another embodiment, the divinyl benzene is divinyl benzene sulfonate. In another embodiment, the polymer is a salt of crosslinked polystyrene sulfonate. In yet another embodiment, the composition is further substantially active as a phosphate binder. In another embodiment, the patient is experiencing hyperkalemia. In yet another embodiment, the polymer has a capacity to increase fecal phosphorous output in a subject. In another embodiment, the polymer has a capacity to decrease urinary phosphorous output in a subject.

Another aspect of the invention relates to a pharmaceutical composition comprising a calcium salt of a crosslinked potassium binding polymer that has a potassium exchange capacity from about 1 mEq to about 4 mEq per gram of potassium binding polymer and a pharmaceutically acceptable carrier, diluent, or excipient, wherein the potassium binding polymer is characterized by a crosslinking of less than 5% and wherein median diameter is from about 1 µm to about 130 µm when said particles are in their calcium salt form and swollen in water. In some embodiments, the polymer is a styrene polymer. In another embodiment, the polymer is crosslinked with divinyl benzene. In yet another embodiment, the divinyl benzene is divinyl benzene sulfonate. In another embodiment, the polymer is a salt of crosslinked polystyrene sulfonate. In yet another embodiment, the composition is further substantially active as a phosphate binder. In another embodiment, the patient is experiencing hyperkalemia. In yet another embodiment, the polymer has a capacity to increase fecal phosphorous output in a subject. In another embodiment, the polymer has a capacity to decrease urinary phosphorous output in a subject.

In another aspect, the present invention relates to a pharmaceutical composition comprising a calcium salt of a crosslinked potassium binding polymer and a pharmaceutically acceptable carrier, diluent, or excipient, wherein the crosslinked potassium binding polymer is characterized by a crosslinking of less than 5% and wherein median diameter is from about 1 μm to about 130 μm when said particles are in their calcium salt form and swollen in water. In some embodiments, the polymer is a styrene polymer. In another embodiment, the polymer is crosslinked with divinyl benzene. In yet another embodiment, the divinyl benzene is divinyl benzene sulfonate. In another embodiment, the polymer is a salt of crosslinked polystyrene sulfonate. In yet another embodiment, the composition is further substantially active as a phosphate binder. In another embodiment, the patient is experiencing hyperkalemia. In yet another embodiment, the polymer has a capacity to increase fecal phosphorous output in a subject. In another embodiment, the polymer has a capacity to decrease urinary phosphorous output in a subject.

Another aspect of the invention relates to a composition for removing potassium from the gastrointestinal tract of a patient showing clinical signs of hyperkalemia or suspected of having hyperkalemia, comprising a calcium salt of a potassium binding polymer, or salt thereof, to the patient, wherein the crosslinked potassium binding polymer has a structure of Formula (I):

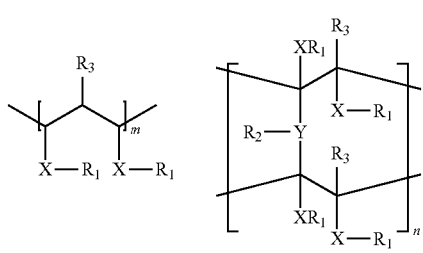

and pharmaceutically acceptable salts thereof
wherein:
each $R_1$ is independently selected from the group consisting of H, substituted or unsubstituted ($C_1$-$C_6$) alkyl, substituted or unsubstituted ($C_6$-$C_{18}$) aryl, —S(O)$_2$OH, —OS(O)$_2$OH, —C(O)OH, —PO(OH)$_2$, —OP(OH)$_3$, and —NHS(O)$_2$OH;
each $R_2$ is independently selected from the group consisting of H, substituted or unsubstituted ($C_1$-$C_6$)alkyl, substituted or unsubstituted ($C_6$-$C_{18}$)aryl, —S(O)$_2$OH, —OS(O)$_2$OH, —C(O)OH, —PO(OH)$_2$, —OP(OH)$_3$, and —NHS(O)$_2$OH;
each $R_3$ is independently selected from the group consisting of H, halogen, substituted or unsubstituted ($C_1$-$C_6$) alkyl, substituted or unsubstituted ($C_6$-$C_{18}$)aryl, —S(O)$_2$OH, —OS(O)$_2$OH, —C(O)OH, —PO(OH)$_2$, —OP(OH)$_3$, and —NHS(O)$_2$OH;
each X is either absent or independently selected from the group consisting of substituted or unsubstituted ($C_1$-$C_6$)alkyl and substituted or unsubstituted ($C_6$-$C_{18}$)aryl;
each Y is independently selected from the group consisting of substituted or unsubstituted ($C_1$-$C_6$)alkyl and substituted or unsubstituted ($C_6$-$C_{18}$)aryl; and
the mole ratio of m to n is from about 120:1 to about 40:1;
wherein the crosslinked potassium binding polymer is characterized by a crosslinking of less than 5%; and
a pharmaceutically acceptable carrier, diluent, or excipient.

Another aspect of the invention relates to a pharmaceutical composition comprising: a i) a calcium salt of a crosslinked potassium binding polymer of Formula (I) and pharmaceutically acceptable salts thereof; ii) calcium citrate tetrahydrate; iii) anhydrous citric acid; iv) sucralose; v) artificial orange flavored powder; and vi) methyl cellulose.

In some embodiments, the pharmaceutical composition comprises about 86.5% to about 91% of a calcium salt of a crosslinked potassium binding polymer of Formula (I) and pharmaceutically acceptable salts thereof. In another embodiment, the pharmaceutical composition comprises about 87% to about 90% of a calcium salt of a crosslinked potassium binding polymer of Formula (I) and pharmaceutically acceptable salts thereof. In yet another embodiment, the pharmaceutical composition comprises about 88% to about 89% of the calcium salt of a crosslinked potassium binding polymer of Formula (I) and pharmaceutically acceptable salts thereof. In another embodiment, the pharmaceutical composition comprises about 86%, about 87%, about 88%, about 89%, or about 90% of a calcium salt of a crosslinked potassium binding polymer of Formula (I) and pharmaceutically acceptable salts thereof. In yet another embodiment, the pharmaceutical composition comprises about 88.6% of a calcium salt of a crosslinked potassium binding polymer of Formula (I) and pharmaceutically acceptable salts thereof.

In some embodiments, the pharmaceutical composition comprises about 2.0% to about 3.0% of calcium citrate tetrahydrate. In another embodiment, the pharmaceutical composition comprises about 2.1% to about 2.9% of calcium citrate tetrahydrate. In yet another embodiment, the pharmaceutical composition comprises about 2.2% to about 2.8% of calcium citrate tetrahydrate. In another embodiment, the pharmaceutical composition comprises about 2.3% to about 2.7% of calcium citrate tetrahydrate. In yet another embodiment, the pharmaceutical composition comprises about 2.4% to about 2.6% of calcium citrate tetrahydrate. In another embodiment, the pharmaceutical composition comprises about 2.5% to about 2.7% of calcium citrate tetrahydrate. In yet another embodiment, the pharmaceutical composition comprises about 2.0%, about 2.1%, about 2.2%, about 2.3%, about 2.4%, about 2.5%, about 2.6%, about 2.8%, about 2.9%, or about 3.0% of calcium citrate tetrahydrate. In another embodiment, the pharmaceutical composition comprises about 2.64% of calcium citrate tetrahydrate.

In some embodiments, the pharmaceutical composition comprises about 2.0% to about 3.0% of anhydrous citric acid. In another embodiment, the pharmaceutical composition comprises about 2.1% to about 2.9% of anhydrous citric acid. In yet another embodiment, the pharmaceutical composition comprises about 2.2% to about 2.8% of anhydrous citric acid. In another embodiment, the pharmaceutical composition comprises about 2.3% to about 2.7% of anhydrous citric acid. In yet another embodiment, the pharmaceutical composition comprises about 2.4% to about 2.6% of anhydrous citric acid. In another embodiment, the pharmaceutical composition comprises about 2.5% to about 2.7% of anhydrous citric acid. In yet another embodiment, the pharmaceutical composition comprises about 2.0%, about 2.1%, about 2.2%, about 2.3%, about 2.4%, about 2.5%, about 2.6%, about 2.7%, about 2.8%, about 2.9%, or about 3.0% of anhydrous citric acid. In another embodiment, the pharmaceutical composition comprises about 2.66% of anhydrous citric acid.

In some embodiments, the pharmaceutical composition comprises about 0.1% to about 1% of sucralose. In another embodiment, the pharmaceutical composition comprises about 0.2% to about 0.9% of sucralose. In yet another embodiment, the pharmaceutical composition comprises about 0.3% to about 0.8% of sucralose. In another embodiment, the pharmaceutical composition comprises about 0.4% to about 0.8% of sucralose. In another embodiment, the pharmaceutical composition comprises about 0.5% to about 0.7% of sucralose. In yet another embodiment, the pharmaceutical composition comprises about 0.1%, about 0.2%, about 0.3%, about 0.4%, about 0.5%, about 0.6%, about 0.7%, about 0.8%, about 0.9%, or about 1.0% of sucralose. In another embodiment, the pharmaceutical composition comprises about 0.53% of sucralose.

In some embodiments, the pharmaceutical composition comprises about 2.0% to about 3.0% of artificial orange flavored powder. In another embodiment, the pharmaceutical composition comprises about 2.1% to about 2.9% of artificial orange flavored powder. In yet another embodiment, the pharmaceutical composition comprises about 2.2% to about 2.8% of artificial orange flavored powder. In another embodiment, the pharmaceutical composition comprises about 2.3% to about 2.7% of artificial orange flavored powder. In yet another embodiment, the pharmaceutical composition comprises about 2.4% to about 2.6% of artificial orange flavored powder. In another embodiment, the pharmaceutical composition comprises about 2.5% to about 2.7% of artificial orange flavored powder. In yet another embodiment, the pharmaceutical composition comprises about 2.0%, about 2.1%, about 2.2%, about 2.3%, about 2.4%, about 2.5%, about 2.6%, about 2.7%, about 2.8%, about 2.9%, or about 3.0% of artificial orange flavored powder. In another embodiment, the pharmaceutical composition comprises about 2.66% of artificial orange flavored powder. In one embodiment, the artificial orange flavored powder is artificial orange flavored powder FV633.

In some embodiments, the pharmaceutical composition comprises about 2.5% to about 3.5% of methyl cellulose. In another embodiment, the pharmaceutical composition comprises about 2.6% to about 3.4% of methyl cellulose. In yet another embodiment, the pharmaceutical composition comprises about 2.7% to about 3.3% of methyl cellulose. In another embodiment, the pharmaceutical composition comprises about 2.8% to about 3.2% of methyl cellulose. In yet another embodiment, the pharmaceutical composition comprises about 2.9% to about 3.1% of methyl cellulose. In another embodiment, the pharmaceutical composition comprises about 2.8% to about 3.0% of methyl cellulose. In yet another embodiment, the pharmaceutical composition comprises about 2.5%, about 2.6%, about 2.7%, about 2.8%, about 2.9%, about 3.0%, about 3.1%, about 3.2%, about 3.3%, about 3.4%, or about 3.5% of methyl cellulose. In yet another embodiment, the pharmaceutical composition comprises about 2.92% of methyl cellulose. In one embodiment, the methyl cellulose is methyl cellulose A4C.

Another aspect of the invention relates to a pharmaceutical composition comprising: i) a calcium salt of a crosslinked potassium binding polymer of Formula (I) and pharmaceutically acceptable salts thereof; ii) calcium citrate tetrahydrate; iii) anhydrous citric acid; iv) sucralose; v) vanillin powder; vi) methyl cellulose; and vii) titanium dioxide.

In some embodiments, the pharmaceutical composition comprises about 89% to about 94.5% of a calcium salt of a crosslinked potassium binding polymer of Formula (I) and pharmaceutically acceptable salts thereof. In another embodiment, the pharmaceutical composition comprises about 90% to about 93.5% of a calcium salt of a crosslinked potassium binding polymer of Formula (I) and pharmaceutically acceptable salts thereof. In yet another embodiment, the pharmaceutical composition comprises about 91% to about 92.5% of a calcium salt of a crosslinked potassium binding polymer of Formula (I) and pharmaceutically acceptable salts thereof. In another embodiment, the pharmaceutical composition comprises about 89%, about 89.5%, about 90%, about 90.5%, about 91%, about 91.5%, about 92%, about 92.5%, about 93%, about 93.5%, about 94%, about 94.5% of a calcium salt of a crosslinked potassium binding polymer of Formula (I) and pharmaceutically acceptable salts thereof. In yet another embodiment, the pharmaceutical composition comprises about 91.7% of a calcium salt of a crosslinked potassium binding polymer of Formula (I) and pharmaceutically acceptable salts thereof.

In some embodiments, the pharmaceutical composition comprises about 0.6% to about 1.6% of calcium citrate tetrahydrate. In another embodiment, the pharmaceutical composition comprises about 0.7% to about 1.5% of calcium citrate tetrahydrate. In yet another embodiment, the pharmaceutical composition comprises about 0.8% to about 1.4% of calcium citrate tetrahydrate. In another embodiment, the pharmaceutical composition comprises about 0.8% to about 1.3% of calcium citrate tetrahydrate. In yet another embodiment, the pharmaceutical composition comprises about 0.9% to about 1.2% of calcium citrate tetrahydrate. In another embodiment, the pharmaceutical composition comprises about 0.6%, about 0.7%, about 0.8%, about 0.9%, about 1.0%, about 1.1%, about 1.2%, about 1.3%, about 1.4%, about 1.5%, or about 1.6% of calcium citrate tetrahydrate. In another embodiment, the pharmaceutical composition comprises about 1.21% of calcium citrate tetrahydrate.

In some embodiments, the pharmaceutical composition comprises about 0.02% to about 0.5% of anhydrous citric acid. In another embodiment, the pharmaceutical composition comprises about 0.03% to about 0.4% of anhydrous citric acid. In yet another embodiment, the pharmaceutical composition comprises about 0.04% to about 0.3% of anhydrous citric acid. In another embodiment, the pharmaceutical composition comprises about 0.05% to about 0.2% of anhydrous citric acid. In yet another embodiment, the pharmaceutical composition comprises about 0.1% to about 0.3% of anhydrous citric acid. In another embodiment, the pharmaceutical composition comprises about 0.2% to about 0.3% of anhydrous citric acid. In yet another embodiment, the pharmaceutical composition comprises about 0.02%, about 0.03%, about 0.04%, about 0.05%, about 0.06%, about 0.07%, about 0.08%, about 0.09%, about 0.1%, about 0.2%, about 0.3%, about 0.4%, or about 0.5% of anhydrous citric acid. In another embodiment, the pharmaceutical composition comprises about 0.24% of anhydrous citric acid.

In some embodiments, the pharmaceutical composition comprises about 0.1% to about 1% of sucralose. In another embodiment, the pharmaceutical composition comprises about 0.2% to about 0.9% of sucralose. In yet another embodiment, the pharmaceutical composition comprises about 0.3% to about 0.8% of sucralose. In another embodiment, the pharmaceutical composition comprises about 0.4% to about 0.7% of sucralose. In yet another embodiment, the pharmaceutical composition comprises about 0.5% to about 0.6% of sucralose. In another embodiment, the pharmaceutical composition comprises about 0.1%, about 0.2%, about 0.3%, about 0.4%, about 0.5%, about 0.6%, about 0.7%, about 0.8%, about 0.9%, or about 1.0% of sucralose. In yet another embodiment, the pharmaceutical composition comprises about 0.55% of sucralose.

In some embodiments, the pharmaceutical composition comprises about 0.6% to about 1.6% of vanillin powder. In another embodiment, the pharmaceutical composition comprises about 0.7% to about 1.5% of vanillin powder. In yet another embodiment, the pharmaceutical composition comprises about 0.8% to about 1.4% of vanillin powder. In another embodiment, the pharmaceutical composition comprises about 0.9% to about 1.3% of vanillin powder. In yet another embodiment, the pharmaceutical composition comprises about 1.0% to about 1.2% of vanillin powder. In another embodiment, the pharmaceutical composition comprises about 0.6%, about 0.7%, about 0.8%, about 0.9%, about 1.0%, about 1.1%, about 1.2%, about 1.3%, about 1.4%, about 1.5%, or about 1.6% of vanillin powder.

In some embodiments, the pharmaceutical composition comprises about 2.5% to about 3.5% of methyl cellulose. In another embodiment, the pharmaceutical composition comprises about 2.6% to about 3.4% of methyl cellulose. In yet another embodiment, the pharmaceutical composition comprises about 2.7% to about 3.3% of methyl cellulose. In another embodiment, the pharmaceutical composition comprises about 2.8% to about 3.3% of methyl cellulose. In yet another embodiment, the pharmaceutical composition comprises about 2.9% to about 3.3% of methyl cellulose. In another embodiment, the pharmaceutical composition comprises about 3.0% to about 3.2% of methyl cellulose. In yet another embodiment, the pharmaceutical composition comprises about 2.9% to about 3.1% of methyl cellulose. In another embodiment, the pharmaceutical composition comprises about 2.5%, about 2.6%, about 2.7%, about 2.8%, about 2.9%, about 3.0%, about 3.1%, about 3.2%, about 3.3%, about 3.4%, or about 3.5% of methyl cellulose. In yet another embodiment, the pharmaceutical composition comprises about 3.03% of methyl cellulose. In one embodiment, the methyl cellulose is methyl cellulose A4C.

In some embodiments, the pharmaceutical composition comprises about 1.6% to about 2.6% of titanium dioxide. In another embodiment, the pharmaceutical composition comprises about 1.7% to about 2.5% of titanium dioxide. In yet another embodiment, the pharmaceutical composition comprises about 1.8% to about 2.4% of titanium dioxide. In another embodiment, the pharmaceutical composition comprises about 1.9% to about 2.3% of titanium dioxide. In yet another embodiment, the pharmaceutical composition comprises about 2.0% to about 2.3% of titanium dioxide. In another embodiment, the pharmaceutical composition comprises about 1.6%, about 1.7%, about 1.8%, about 1.9%, about 2.0%, about 2.1%, about 2.2%, about 2.3%, about 2.4%, about 2.5%, or about 2.6% of titanium dioxide.

Another aspect of the invention relates to a pharmaceutical composition comprising: i) a calcium salt of a crosslinked potassium binding polymer of Formula (I) and pharmaceutically acceptable salts thereof; ii) calcium citrate tetrahydrate; iii) benzoic acid; iv) anhydrous citric acid; v) sucralose; vi) of natural orange WONF FV7466; vii) xanthan gµm; and viii) water.

In some embodiments, the pharmaceutical composition comprises about 10% to about 26% of a calcium salt of a crosslinked potassium binding polymer of Formula (I) and pharmaceutically acceptable salts thereof. In another embodiment, the pharmaceutical composition comprises about 11% to about 25% of a calcium salt of a crosslinked potassium binding polymer of Formula (I) and pharmaceutically acceptable salts thereof. In yet another embodiment, the pharmaceutical composition comprises about 12% to about 24% of a calcium salt of a crosslinked potassium binding polymer of Formula (I) and pharmaceutically acceptable salts thereof. In another embodiment, the pharmaceutical composition comprises about 13% to about 23% of a calcium salt of a crosslinked potassium binding polymer of Formula (I) and pharmaceutically acceptable salts thereof. In yet another embodiment, the pharmaceutical composition comprises about 14% to about 22% of a calcium salt of a crosslinked potassium binding polymer of Formula (I) and pharmaceutically acceptable salts thereof. In another embodiment, the pharmaceutical composition comprises about 15% to about 21% of a calcium salt of a crosslinked potassium binding polymer of Formula (I) and pharmaceutically acceptable salts thereof. In yet another embodiment, the pharmaceutical composition comprises about 16% to about 20% of a calcium salt of a crosslinked potassium binding polymer of Formula (I) and pharmaceutically acceptable salts thereof. In another embodiment, the pharmaceutical composition comprises about 15% to about 19% of a calcium salt of a crosslinked potassium binding polymer of Formula (I) and pharmaceutically acceptable salts thereof. In yet another embodiment, the pharmaceutical composition comprises about 16% to about 18% of a calcium salt of a crosslinked potassium binding polymer of Formula (I) and pharmaceutically acceptable salts thereof. In another embodiment, the pharmaceutical composition comprises about 15% to about 17% of a calcium salt of a crosslinked potassium binding polymer of Formula (I) and pharmaceutically acceptable salts thereof. In yet another embodiment, the pharmaceutical composition comprises about 10%, about 11%, about 12%, about 13%, about 14%, about 15%, about 16%, about 17%, about 18%, about 19%, about 20%, about 21%, about 22%, about 23%, about 24%, about 25%, or about 26% of a calcium salt of a crosslinked potassium binding polymer of Formula (I) and pharmaceutically acceptable salts thereof. In another embodiment, the pharmaceutical composition comprises about 16.28% of a calcium salt of a crosslinked potassium binding polymer of Formula (I) and pharmaceutically acceptable salts thereof.

In some embodiments, the pharmaceutical composition comprises about 0.1% to about 1.0% of calcium citrate tetrahydrate. In another embodiment, the pharmaceutical composition comprises about 0.2% to about 0.9% of calcium citrate tetrahydrate. In yet another embodiment, the pharmaceutical composition comprises about 0.3% to about 0.8% of calcium citrate tetrahydrate. In another embodiment, the pharmaceutical composition comprises about 0.4% to about 0.7% of calcium citrate tetrahydrate. In yet another embodiment, the pharmaceutical composition comprises about 0.5% to about 0.6% of calcium citrate tetrahydrate. In another embodiment, the pharmaceutical composition comprises about 0.4% to about 0.6% of calcium citrate tetrahydrate. In yet another embodiment, the pharmaceutical composition comprises about 0.4% to about 0.5% of calcium citrate tetrahydrate. In another embodiment, the pharmaceutical composition comprises about 0.1%, about 0.2%, about 0.3%, about 0.4%, about 0.5%, about 0.6%, about 0.7%, about 0.8%, about 0.9%, or about 1.0% of calcium citrate tetrahydrate. In yet another embodiment, the pharmaceutical composition comprises about 0.49% of calcium citrate tetrahydrate.

In some embodiments, the pharmaceutical composition comprises about 0.015% to about 0.15% of benzoic acid. In another embodiment, the pharmaceutical composition comprises about 0.02% to about 0.12% of benzoic acid. In yet another embodiment, the pharmaceutical composition comprises about 0.03% to about 0.13% of benzoic acid. In another embodiment, the pharmaceutical composition comprises about 0.04% to about 0.12% of benzoic acid. In yet another embodiment, the pharmaceutical composition comprises about 0.05% to about 0.11% of benzoic acid. In another embodiment, the pharmaceutical composition comprises about 0.06% to about 0.10% of benzoic acid. In yet another embodiment, the pharmaceutical composition comprises about 0.07% to about 0.11% of benzoic acid. In another embodiment, the pharmaceutical composition comprises about 0.08% to about 0.11% of benzoic acid. In yet another embodiment, the pharmaceutical composition comprises about 0.090% to about 0.11% of benzoic acid. In another embodiment, the pharmaceutical composition comprises about 0.015%, 0.02%, 0.03%, 0.04%, 0.05%, 0.06%, 0.07%, 0.08%, 0.09%, 0.10%, 0.11%, 0.12%, 0.13%, 0.14%, or about 0.15% of benzoic acid.

In some embodiments, the pharmaceutical composition comprises about 0.1% to about 1% of anhydrous citric acid. In another embodiment, the pharmaceutical composition comprises about 0.2% to about 0.9% of anhydrous citric acid. In yet another embodiment, the pharmaceutical composition comprises about 0.3% to about 0.8% of anhydrous citric acid. In another embodiment, the pharmaceutical composition comprises about 0.4% to about 0.8% of anhydrous citric acid. In yet another embodiment, the pharmaceutical composition comprises about 0.5% to about 0.7% of anhydrous citric acid. In another embodiment, the pharmaceutical composition comprises about 0.4% to about 0.6% of anhydrous citric acid. In yet another embodiment, the pharmaceutical composition comprises about 0.4% to about 0.5% of anhydrous citric acid. In another embodiment, the pharmaceutical composition comprises about 0.1%, about 0.2%, about 0.3%, about 0.4%, about 0.5%, about 0.6%, about 0.7%, about 0.8%, about 0.9%, or about 1% of anhydrous citric acid. In yet another embodiment, the pharmaceutical composition comprises about 0.49% of anhydrous citric acid.

In some embodiments, the pharmaceutical composition comprises about 0.015% to about 0.15% of sucralose. In another embodiment, the pharmaceutical composition comprises about 0.02% to about 0.14% of sucralose. In yet another embodiment, the pharmaceutical composition comprises about 0.03% to about 0.13% of sucralose. In another embodiment, the pharmaceutical composition comprises about 0.04% to about 0.12% of sucralose. In another embodiment, the pharmaceutical composition comprises about 0.05% to about 0.11% of sucralose. In yet another embodiment, the pharmaceutical composition comprises about 0.06% to about 0.10% of sucralose. In another embodiment, the pharmaceutical composition comprises about 0.07% to about 0.11% of sucralose. In yet another embodiment, the pharmaceutical composition comprises about 0.08% to about 0.11% of sucralose. In another embodiment, the pharmaceutical composition comprises about 0.09% to about 0.11% of sucralose. In yet another embodiment, the pharmaceutical composition comprises about 0.10% to about 0.11% of sucralose. In another embodiment, the pharmaceutical composition comprises about 0.015%, about 0.02%, about 0.03%, about 0.04%, about 0.05%, about 0.06%, about 0.07%, about 0.08%, about 0.09%, about 0.10%, about 0.11%, about 0.12%, about 0.13%, about 0.14%, or about 0.15% of sucralose.

In some embodiments, the pharmaceutical composition comprises about 0.1% to about 1.0% of natural orange WONF FV7466. In another embodiment, the pharmaceutical composition comprises about 0.2% to about 0.9% of natural orange WONF FV7466. In yet another embodiment, the pharmaceutical composition comprises about 0.3% to about 0.8% of natural orange WONF FV7466. In another embodiment, the pharmaceutical composition comprises about 0.4% to about 0.8% of natural orange WONF FV7466. In yet another embodiment, the pharmaceutical composition comprises about 0.5% to about 0.7% of natural orange WONF FV7466. In another embodiment, the pharmaceutical composition comprises about 0.4% to about 0.6% of natural orange WONF FV7466. In yet another embodiment, the pharmaceutical composition comprises about 0.4% to about 0.5% of natural orange WONF FV7466. In another embodiment, the pharmaceutical composition comprises about 0.1%, about 0.2%, about 0.3%, about 0.4%, about 0.5%, about 0.6%, about 0.7%, about 0.8%, about 0.9%, or about 1% of natural orange WONF FV7466. In yet another embodiment, the pharmaceutical composition comprises about 0.49% of natural orange WONF FV7466.

In some embodiments, the pharmaceutical composition comprises about 0.1% to about 1.0% of xanthan gum. In another embodiment, the pharmaceutical composition comprises about 0.2% to about 0.9% of xanthan gum. In yet another embodiment, the pharmaceutical composition comprises about 0.3% to about 0.8% of xanthan gum. In another embodiment, the pharmaceutical composition comprises about 0.4% to about 0.8% of xanthan gum. In yet another embodiment, the pharmaceutical composition comprises about 0.5% to about 0.7% of xanthan gum. In another embodiment, the pharmaceutical composition comprises about 0.4% to about 0.6% of xanthan gum. In yet another embodiment, the pharmaceutical composition comprises about 0.4% to about 0.5% of xanthan gum. In another embodiment, the pharmaceutical composition comprises about 0.1%, about 0.2%, about 0.3%, about 0.4%, about 0.5%, about 0.6%, about 0.7%, about 0.8%, about 0.9%, or about 1% of xanthan gum. In yet another embodiment, the pharmaceutical composition comprises about 0.68% of xanthan gum. In one embodiment, the xanthan gum is xanthan gum cp.

In some embodiments, the pharmaceutical composition comprises about 73.7% to about 85.6% of water. In another embodiment, the pharmaceutical composition comprises about 74% to about 84% of water. In yet another embodiment, the pharmaceutical composition comprises about 75% to about 83% of water. In another embodiment, the pharmaceutical composition comprises about 76% to about 82% of water. In yet another embodiment, the pharmaceutical composition comprises about 77% to about 81% of water. In another embodiment, the pharmaceutical composition comprises about 78% to about 82% of water. In yet another embodiment, the pharmaceutical composition comprises about 79% to about 82% of water. In another embodiment, the pharmaceutical composition comprises about 80% to about 82% of water. In yet another embodiment, the pharmaceutical composition comprises about 73.7%, about 74%, about 75%, about 76%, about 77%, about 78%, about 79%, about 80%, about 81%, about 82%, about 83%, or about 84% of water. In another embodiment, the pharmaceutical composition comprises about 81.4% of water.

Another aspect of the invention relates to a pharmaceutical composition comprising: i) a calcium salt of a crosslinked potassium binding polymer of Formula (I) and pharmaceutically acceptable salts thereof; ii) calcium citrate tetrahydrate; iii) sorbic acid; iv) anhydrous citric acid; v) sucralose; vi) SuperVan art vanilla VM36; vii) xanthan gum cp; viii) titanium dioxide; and ix) water.

In some embodiments, the pharmaceutical composition comprises about 10% to about 26% of a calcium salt of a crosslinked potassium binding polymer of Formula (I) and pharmaceutically acceptable salts thereof. In another embodiment, the pharmaceutical composition comprises about 11% to about 25% of a calcium salt of a crosslinked potassium binding polymer of Formula (I) and pharmaceutically acceptable salts thereof. In yet another embodiment, the pharmaceutical composition comprises about 12% to about 24% of a calcium salt of a crosslinked potassium binding polymer of Formula (I) and pharmaceutically acceptable salts thereof. In another embodiment, the pharmaceutical composition comprises about 13% to about 23% of a calcium salt of a crosslinked potassium binding polymer of Formula (I) and pharmaceutically acceptable salts thereof. In yet another embodiment, the pharmaceutical composition comprises about 14% to about 22% of a calcium salt of a crosslinked potassium binding polymer of Formula (I) and pharmaceutically acceptable salts thereof. In another embodiment, the pharmaceutical composition comprises about 15% to about 21% of a calcium salt of a crosslinked potassium binding polymer of Formula (I) and pharmaceutically acceptable salts thereof. In yet another embodiment, the pharmaceutical composition comprises about 16% to about 20% of a calcium salt of a crosslinked potassium binding polymer of Formula (I) and pharmaceutically acceptable salts thereof. In another embodiment, the pharmaceutical composition comprises about 15% to about 19% of a calcium salt of a crosslinked potassium binding polymer of Formula (I) and pharmaceutically acceptable salts thereof. In yet another embodiment, the pharmaceutical composition comprises about 16% to about 18% of a calcium salt of a crosslinked potassium binding polymer of Formula (I) and pharmaceutically acceptable salts thereof. In another embodiment, the pharmaceutical composition comprises about 15% to about 17% of a calcium salt of a crosslinked potassium binding polymer of Formula (I) and pharmaceutically acceptable salts thereof. In yet another embodiment, the pharmaceutical composition comprises about 10%, about 11%, about 12%, about 13%, about 14%, about 15%, about 16%, about 17%, about 18%, about 19%, about 20%, about 21%, about 22%, about 23%, about 24%, about 25%, or about 26% of a calcium salt of a crosslinked potassium binding polymer of Formula (I) and pharmaceutically acceptable salts thereof. In another embodiment, the pharmaceutical composition comprises about 16.36% of a calcium salt of a crosslinked potassium binding polymer of Formula (I) and pharmaceutically acceptable salts thereof.

In some embodiments, the pharmaceutical composition comprises about 0.01% to about 0.5% of calcium citrate tetrahydrate. In another embodiment, the pharmaceutical composition comprises about 0.02% to about 0.4% of calcium citrate tetrahydrate. In yet another embodiment, the pharmaceutical composition comprises about 0.03% to about 0.3% of calcium citrate tetrahydrate. In another embodiment, the pharmaceutical composition comprises about 0.04% to about 0.2% of calcium citrate tetrahydrate. In yet another embodiment, the pharmaceutical composition comprises about 0.06% to about 0.3% of calcium citrate tetrahydrate. In another embodiment, the pharmaceutical composition comprises about 0.07% to about 0.3% of calcium citrate tetrahydrate. In yet another embodiment, the pharmaceutical composition comprises about 0.08% to about 0.3% of calcium citrate tetrahydrate. In another embodiment, the pharmaceutical composition comprises about 0.09% to about 0.3% of calcium citrate tetrahydrate. In yet another embodiment, the pharmaceutical composition comprises about 0.01% to about 0.3% of calcium citrate tetrahydrate. In another embodiment, the pharmaceutical composition comprises about 0.01%, 0.02%, 0.03%, 0.04%, 0.05%, 0.06%, 0.07%, 0.08%, 0.09%, about 0.1%, about 0.2%, about 0.3%, about 0.4%, or about 0.5% of calcium citrate tetrahydrate. In yet another embodiment, the pharmaceutical composition comprises about 0.22% of calcium citrate tetrahydrate.

In some embodiments, the pharmaceutical composition comprises about 0.01% to about 0.1% of sorbic acid. In another embodiment, the pharmaceutical composition comprises about 0.02% to about 0.09% of sorbic acid. In yet another embodiment, the pharmaceutical composition comprises about 0.03% to about 0.08% of sorbic acid. In another embodiment, the pharmaceutical composition comprises about 0.04% to about 0.07% of sorbic acid. In yet another embodiment, the pharmaceutical composition comprises about 0.04% to about 0.06% of sorbic acid. In another embodiment, the pharmaceutical composition comprises about 0.01%, about 0.02%, about 0.03%, about 0.04%, about 0.05%, about 0.06%, about 0.07%, about 0.08%, about 0.09%, or about 0.1% of sorbic acid.

In some embodiments, the pharmaceutical composition comprises about 0.001% to about 0.1% of anhydrous citric acid. In another embodiment, the pharmaceutical composition comprises about 0.002% to about 0.09% of anhydrous citric acid. In yet another embodiment, the pharmaceutical composition comprises about 0.003% to about 0.08% of anhydrous citric acid. In another embodiment, the pharmaceutical composition comprises about 0.004% to about 0.07% of anhydrous citric acid. In yet another embodiment, the pharmaceutical composition comprises about 0.005% to about 0.06% of anhydrous citric acid. In another embodiment, the pharmaceutical composition comprises about 0.006% to about 0.05% of anhydrous citric acid. In yet another embodiment, the pharmaceutical composition comprises about 0.007% to about 0.04% of anhydrous citric acid. In another embodiment, the pharmaceutical composition comprises about 0.008% to about 0.03% of anhydrous citric acid. In yet another embodiment, the pharmaceutical composition comprises about 0.009% to about 0.02% of anhydrous citric acid. In another embodiment, the pharmaceutical composition comprises about 0.001%, about 0.002%, about 0.003%, about 0.004%, about 0.005%, about 0.006%, about 0.007%, about 0.008%, about 0.009%, about 0.01%, about 0.02%, about 0.03%, about 0.04%, about 0.05%, about 0.06%, about 0.07%, about 0.08%, about 0.09%, or about 0.1% of anhydrous citric acid In some embodiments, the pharmaceutical composition comprises about 0.05% to about 0.15% of sucralose. In another embodiment, the pharmaceutical composition comprises about 0.06% to about 0.14% of sucralose. In yet another embodiment, the pharmaceutical composition comprises about 0.07% to about 0.13% of sucralose. In another embodiment, the pharmaceutical composition comprises about 0.08% to about 0.12% of sucralose. In yet another embodiment, the pharmaceutical composition comprises about 0.09% to about 0.11% of sucralose. In another embodiment, the pharmaceutical composition comprises about 0.05%, about 0.06%, about 0.07%, about 0.08%, about 0.09%, about 0.10%, about 0.11%, about 0.12%, about 0.13%, or about 0.14% of sucralose.

In some embodiments, the pharmaceutical composition comprises about 0.1% to about 1.0% of SuperVan art vanilla VM36. In another embodiment, the pharmaceutical composition comprises about 0.2% to about 0.9% of SuperVan art vanilla VM36. In yet another embodiment, the pharmaceutical composition comprises about 0.3% to about 0.8% of SuperVan art vanilla VM36. In another embodiment, the pharmaceutical composition comprises about 0.4% to about 0.8% of SuperVan art vanilla VM36. In yet another embodiment, the pharmaceutical composition comprises about 0.5% to about 0.7% of SuperVan art vanilla VM36. In another embodiment, the pharmaceutical composition comprises about 0.4% to about 0.6% of SuperVan art vanilla VM36. In yet another embodiment, the pharmaceutical composition comprises about 0.4% to about 0.5% of SuperVan art vanilla VM36. In another embodiment, the pharmaceutical composition comprises about 0.1%, about 0.2%, about 0.3%, about 0.4%, about 0.5%, about 0.6%, about 0.7%, about 0.8%, about 0.9%, or about 1% of SuperVan art vanilla VM36. In yet another embodiment, the pharmaceutical composition comprises about 0.49% of SuperVan art vanilla VM36.

In some embodiments, the pharmaceutical composition comprises about 0.1% to about 1.0% of xanthan gum. In another embodiment, the pharmaceutical composition comprises about 0.2% to about 0.9% of xanthan gum. In yet another embodiment, the pharmaceutical composition comprises about 0.3% to about 0.8% of xanthan gum. In another embodiment, the pharmaceutical composition comprises about 0.4% to about 0.8% of xanthan gum. In yet another embodiment, the pharmaceutical composition comprises about 0.5% to about 0.7% of xanthan gum. In another embodiment, the pharmaceutical composition comprises about 0.4% to about 0.6% of xanthan gum. In yet another embodiment, the pharmaceutical composition comprises about 0.4% to about 0.5% of xanthan gum. In another embodiment, the pharmaceutical composition comprises about 0.1%, about 0.2%, about 0.3%, about 0.4%, about 0.5%, about 0.6%, about 0.7%, about 0.8%, about 0.9%, or about 1% of xanthan gum. In yet another embodiment, the pharmaceutical composition comprises about 0.59% of xanthan gum. In one embodiment, the xanthan gum is xanthan gum cp.

In some embodiments, the pharmaceutical composition comprises about 0.1% to about 1.0% of titanium dioxide. In another embodiment, the pharmaceutical composition comprises about 0.2% to about 0.9% of titanium dioxide. In yet another embodiment, the pharmaceutical composition comprises about 0.3% to about 0.8% of titanium dioxide. In another embodiment, the pharmaceutical composition comprises about 0.4% to about 0.8% of titanium dioxide. In yet another embodiment, the pharmaceutical composition comprises about 0.5% to about 0.7% of titanium dioxide. In another embodiment, the pharmaceutical composition comprises about 0.3% to about 0.6% of titanium dioxide. In yet another embodiment, the pharmaceutical composition comprises about 0.3% to about 0.5% of titanium dioxide. In another embodiment, the pharmaceutical composition comprises about 0.1%, about 0.2%, about 0.3%, about 0.4%, about 0.5%, about 0.6%, about 0.7%, about 0.8%, about 0.9%, or about 1% of titanium dioxide. In yet another embodiment, the pharmaceutical composition comprises about 0.39% of titanium dioxide.

In some embodiments, the pharmaceutical composition comprises about 73.2% to about 86.65% water. In another embodiment, the pharmaceutical composition comprises about 74% to about 86% of water. In yet another embodiment, the pharmaceutical composition comprises about 75% to about 85% of water. In another embodiment, the pharmaceutical composition comprises about 76% to about 84% of water. In yet another embodiment, the pharmaceutical composition comprises about 77% to about 83% of water. In another embodiment, the pharmaceutical composition comprises about 78% to about 82% of water. In yet another embodiment, the pharmaceutical composition comprises about 79% to about 82% of water. In another embodiment, the pharmaceutical composition comprises about 80% to about 82% of water. In yet another embodiment, the pharmaceutical composition comprises about 73.2%, about 74%, about 75%, about 76%, about 77%, about 78%, about 79%, about 80%, about 81%, about 82%, about 83%, or about 84% of water. In another embodiment, the pharmaceutical composition comprises about 81.8% of water.

Unless the context requires otherwise, throughout the present specification and claims, the word "comprise" and variations thereof, such as, "comprises" and "comprising" are to be construed in an open, inclusive sense, that is, as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Among the various aspects of the invention are crosslinked cation exchange polymers having desirable particle size, particle shape, particle size distribution, swelling ratio, potassium binding capacity, and methods of removing potassium by administering the polymer—or a pharmaceutical composition including the polymer—to an animal subject in need thereof. Another aspect of the invention is a method for removing potassium and/or treating hyperkalemia from an animal subject in need thereof comprising administering a potassium binding polymer to the animal subject. The potassium binding polymer is a crosslinked cation exchange polymer comprising acid groups in their acid or salt form and in the form of substantially spherical particles having a more controlled particle size distribution than Kayexylate, Kalimate and the like.

Unless particles are perfectly monodisperse, i.e., all the particles have the same dimensions, polymer resins will typically consist of a statistical distribution of particles of different sizes. This distribution of particles can be represented in several ways. Without being bound to a particular theory, it is often convenient to assess particle size using both number weighted distributions and volume weighted distributions. Image analysis is a counting technique and can provide a number weighted distribution: each particle is given equal weighting irrespective of its size. Light scattering techniques such as laser diffraction give a volume weighted distribution: the contribution of each particle in the distribution relates to the volume of that particle, i.e. the relative contribution will be proportional to $(size)^3$.

When comparing particle size data for the same sample measured by different techniques, it is important to realize that the types of distribution being measured and reported can produce very different particle size results. For example, for a sample consisting of equal numbers of particles with diameters of 5 μm and 50 μm, an analytical method that provides a weighted distribution would give equal weighting to both types of particles and said sample would consist of 50% 5 μm particles and 50% 50 μm particles, by number. The same sample, analyzed using an analytical method that provides a volume weighted distribution, would represent the 50 μm samples as present at 1000× the intensity of the 5 μm particles (since volume is a $(radius)^3$ function if assuming the particles are spheres).

For volume weighted particle size distributions, such as those measured by laser diffraction, it is often convenient to report parameters based upon the maximum particle size for a given percentage volume of the sample. Percentiles are defined here using the nomenclature "Dv(B)" where "D"=diameter, "v"=volume, and "B"=is percentage written as a decimal fraction. For example, when expressing particle size for a given sample as "$D_v(0.5)$=50 µm," 50% of the sample is below this particle size. Thus, the $D_v(0.5)$ would be the maximum particle diameter below which 50% of the sample volume exists—also known as the median particle size by volume. For the scenario described earlier wherein a sample consists of equal numbers of particles with diameters of 5 µm and 50 µm, a volume analysis of this sample performed via laser diffraction could theoretically afford: $D_v(0.999)$=50 µm and $D_v(0.001)$=5 µm. In practice, samples are typically characterized by reporting a range of percentiles, typically the median, $D_v(0.5)$, and values above and below the median (e.g., typically $D_v(0.1)$ and $D_v(0.9)$).

The potassium binding polymer is a crosslinked cation exchange polymer comprising acid groups in their acid or salt form and in the form of substantially spherical particles having a median diameter, when in their calcium salt form and swollen in water, of from about 1 µm to about 200 µm. In other embodiments, the substantially spherical particles have a median diameter, when in their calcium salt form and swollen in water, of about 1 µm to about 130 µm. In another embodiment, the substantially spherical particles have a median diameter, when in their calcium salt form and swollen in water, of about 1 µm to about 60 µm. In yet another embodiment, the substantially spherical particles have a median diameter, when in their calcium salt form and swollen in water, of about 60 µm to about 120 µm.

In some embodiments, the $D_v50$—the median particle size by volume and defined as the maximum particle diameter below which 50% of the sample volume exists—is between about 20 µm and about 100 µm. In yet another embodiment, $D_v(0.5)$ is between about 60 µm and about 90 µm. In another embodiment, $D_v(0.5)$ is between about 60 µm and about 70 µm. In another embodiment, $D_v(0.5)$ is between about 80 µm and about 90 µm. In another embodiment, $D_v(0.5)$ is between about 70 µm and about 80 µm. In some embodiments, the $D_v(0.5)$ is about 75 µm.

In other embodiments, the $D_v50$ is between about 20 µm and about 50 µm. In another embodiment, $D_v(0.5)$ is between about 40 µm and about 50 µm. In yet another embodiment, $D_v(0.5)$ is between about 20 µm and about 30 µm. In another embodiment, $D_v(0.5)$ is between about 25 µm and about 35 µm. In yet another embodiment, $D_v(0.5)$ is between about 35 µm and about 45 µm. In another embodiment, $D_v(0.5)$ is between about 30 µm and about 40 µm. In yet another embodiment, $D_v(0.5)$ is about 35 µm. In yet another embodiment, $D_v(0.5)$ is about 30 µm. In another embodiment, $D_v(0.5)$ is about 40 µm. In yet another embodiment, $D_v(0.5)$ is about 45 µm. In another embodiment, $D_v(0.5)$ is about 25 µM.

In some embodiments, the $D_v90$—the median particle size by volume and defined as the maximum particle diameter below which 90% of the sample volume exists—is between about 40 µm and about 140 µm. In yet another embodiment, $D_v(0.9)$ is between about 80 µm and about 130 µm. In another embodiment, $D_v(0.9)$ is between about 90 µm and about 120 µm. In another embodiment, $D_v(0.9)$ is between about 90 µm and about 100 µm. In another embodiment, $D_v(0.9)$ is between about 100 µm and about 120 µm. In other embodiments, the $D_v(0.9)$ is between about 85 µm and about 115 µm. In another embodiment, $D_v(0.9)$ is between about 100 µm and about 120 µm. In yet another embodiment, $D_v(0.9)$ is about 100 µm. In another embodiment, $D_v(0.9)$ is about 105 µm. In yet another embodiment, $D_v(0.9)$ is about 110 µm. In another embodiment, $D_v(0.9)$ is about 90 µm. In yet another embodiment, $D_v(0.9)$ is about 95 µm. In yet another embodiment, $D_v(0.9)$ is about 85 µm.

In other embodiments, the $D_v90$ is between about 20 µm and about 70 µm. In another embodiment, $D_v(0.9)$ is between about 20 µm and about 60 µm. In yet another embodiment, $D_v(0.9)$ is between about 20 µm and about 40 µm. In another embodiment, $D_v(0.9)$ is between about 25 µm and about 35 µm. In yet another embodiment, $D_v(0.9)$ is between about 40 µm and about 70 µm. In another embodiment, $D_v(0.9)$ is between about 40 and about 70 µm. In yet another embodiment, $D_v(0.9)$ is between about 50 µm and about 70 µm. In another embodiment, $D_v(0.9)$ is between about 50 µm and about 60 µm. In yet another embodiment, $D_v(0.9)$ is about 55 µm. In another embodiment, $D_v(0.9)$ is about 50 µm. In yet another embodiment, $D_v(0.9)$ is about 30 µm. In another embodiment, $D_v(0.9)$ is about 35 µm. In yet another embodiment, $D_v(0.9)$ is about 40 µm. In another embodiment, $D_v(0.9)$ is about 45 µm. In yet another embodiment, $D_v(0.9)$ is about 55 µm. In another embodiment, $D_v(0.9)$ is about 60 µm. In yet another embodiment, $D_v(0.9)$ is about 25 µm.

In some embodiments, the $D_v10$—the median particle size by volume and defined as the maximum particle diameter below which 10% of the sample volume exists—is between about 20 µm and about 100 µm. In yet another embodiment, $D_v(0.1)$ is between about 20 µm and about 70 µm. In another embodiment, $D_v(0.1)$ is between about 30 µm and about 60 µm. In yet another embodiment, $D_v(0.1)$ is between about 20 µm and about 40 µm. In another embodiment, $D_v(0.1)$ is between about 20 µm and about 40 µm. In yet another embodiment, $D_v(0.1)$ is between about 40 µm and about 60 µm. In another embodiment, $D_v(0.1)$ is between about 25 µm and about 35 µm. In yet another embodiment, $D_v(0.1)$ is between about 45 µm and about 55 µm.

In other embodiments, the $D_v10$ is between about 1 µm and about 60 µm. In another embodiment, $D_v(0.1)$ is between about 5 µm and about 30 µm. In yet another embodiment, $D_v(0.1)$ is between about 6 µm and about 23 µm. In another embodiment, $D_v(0.1)$ is between about 15 µm and about 25 µm. In another embodiment, $D_v(0.1)$ is between about 1 µm and about 15 µm. In another embodiment, $D_v(0.1)$ is between about 1 µm and about 10 µm. In another embodiment, $D_v(0.1)$ is between about 10 µm and about 20 µm. In another embodiment, $D_v(0.1)$ is about 15 µm. In another embodiment, $D_v(0.1)$ is about 20 µm.

In these embodiments, $D_v(0.1)$ is between about 10 and 80 µm, more preferably between about 30 and 60 µm, and $D_v(0.9)$ is between about 80 and 150 µm, more preferably between about 90 and 120 µm. In another embodiment, Dv(0.5) is between about 60 and 90 µm. In another embodiment, Dv(0.5) is between about 70 and 80 µm.

In some embodiments, the $D_v(0.5)$ is between 60 µm and about 90 µm and $D_v(0.9)$ is between 80 µm and about 130 µm. In another embodiment, the $D_v(0.5)$ is between 70 µm and about 80 µm and $D_v(0.9)$ is between 80 µm and about 130 µm. In yet another embodiment, the $D_v(0.5)$ is between 70 µm and about 80 µm and $D_v(0.9)$ is between 90 µm and about 120 µm.

In another embodiment, the $D_v(0.5)$ is between 60 µm and about 90 µm, $D_v(0.9)$ is between 80 µm and about 130 µm, $D_v(0.1)$ is between 20 µm and about 70 µm. In yet another embodiment, the $D_v(0.5)$ is between 70 µm and about 80 µm, $D_v(0.9)$ is between 80 µm and about 130 µm, $D_v(0.1)$ is between 20 µm and about 70 µm. In another embodiment, the $D_v(0.5)$ is between 60 µm and about 90 µm, $D_v(0.9)$ is between 90 µm and about 120 µm, $D_v(0.1)$ is between 20 µm and about 70 µm. In yet another embodiment, the $D_v(0.5)$ is between 70 µm and about 80 µm, $D_v(0.9)$ is between 90 µm and about 120 µm, $D_v(0.1)$ is between 20 µm and about 70 µm.

In another embodiment, the $D_v(0.5)$ is between 60 µm and about 90 µm, $D_v(0.9)$ is between 80 µm and about 130 µm, $D_v(0.1)$ is between 30 µm and about 60 µm. In yet another embodiment, the $D_v(0.5)$ is between 70 µm and about 80 µm, $D_v(0.9)$ is between 80 µm and about 130 µm, $D_v(0.1)$ is between 30 µm and about 60 µm. In another embodiment, the $D_v(0.5)$ is between 60 µm and about 90 µm, $D_v(0.9)$ is between 90 µm and about 120 µm, $D_v(0.1)$ is between 30 µm and about 60 µm. In yet another embodiment, the $D_v(0.5)$ is between 70 µm and about 80 µm, $D_v(0.9)$ is between 90 µm and about 120 µm, $D_v(0.1)$ is between 30 µm and about 60 µm.

In another embodiment, the $D_v(0.5)$ is between 20 µm and about 50 µm, $D_v(0.9)$ is between 40 µm and about 70 µm, $D_v(0.1)$ is between 5 µm and about 30 µm. In yet another embodiment, the $D_v(0.5)$ is between 30 µm and about 40 µm, $D_v(0.9)$ is between 40 µm and about 70 µm, $D_v(0.1)$ is between 5 µm and about 30 µm. In another embodiment, the $D_v(0.5)$ is between 20 µm and about 50 µm, $D_v(0.9)$ is between 50 µm and about 60 µm, $D_v(0.1)$ is between 5 µm and about 30 µm. In yet another embodiment, the $D_v(0.5)$ is between 30 µm and about 40 µm, $D_v(0.9)$ is between 50 µm and about 60 µm, $D_v(0.1)$ is between 5 µm and about 30 µm.

In another embodiment, the $D_v(0.5)$ is between 20 µm and about 50 µm, $D_v(0.9)$ is between 40 µm and about 70 µm, $D_v(0.1)$ is between 6 µm and about 23 µm. In yet another embodiment, the $D_v(0.5)$ is between 30 µm and about 40 µm, $D_v(0.9)$ is between 40 µm and about 70 µm, $D_v(0.1)$ is between 6 µm and about 23 µm. In another embodiment, the $D_v(0.5)$ is between 20 µm and about 50 µm, $D_v(0.9)$ is between 50 µm and about 60 µm, $D_v(0.1)$ is between 6 µm and about 23 µm. In yet another embodiment, the $D_v(0.5)$ is between 30 µm and about 40 µm, $D_v(0.9)$ is between 50 µm and about 60 µm, $D_v(0.1)$ is between 6 µm and about 23 µm.

In another embodiment, the $D_v(0.5)$ is between 70 µm and about 80 µm, $D_v(0.9)$ is between 110 µm and about 120 µm, $D_v(0.1)$ is between 50 µm and about 60 µm. In yet another embodiment, the $D_v(0.5)$ is between 50 µm and about 60 µm, $D_v(0.9)$ is between 85 µm and about 95 µm, $D_v(0.1)$ is between 25 µm and about 35 µm. In another embodiment, the $D_v(0.5)$ is between 70 µm and about 80 µm, $D_v(0.9)$ is between 100 µm and about 110 µm, $D_v(0.1)$ is between 50 µm and about 60 µm.

In another embodiment, the $D_v(0.5)$ is between 25 µm and about 35 µm, $D_v(0.9)$ is between 45 µm and about 55 µm, $D_v(0.1)$ is between 10 µm and about 20 µm. In yet another embodiment, the $D_v(0.5)$ is between 10 µm and about 20 µm, $D_v(0.9)$ is between 25 µm and about 35 µm, $D_v(0.1)$ is between 1 µm and about 10 µm. In another embodiment, the $D_v(0.5)$ is <35 µm, $D_v(0.9)$ is <55 µm, $D_v(0.1)$ is >5 µm.

In yet another embodiment, $D_v(0.5)$ is between about 60 µm and about 90 µm. In another embodiment, $D_v(0.5)$ is between about 60 µm and about 70 µm. In another embodiment, $D_v(0.5)$ is between about 80 µm and about 90 µm. In another embodiment, $D_v(0.5)$ is between about 70 µm and about 80 µm. In some embodiments, the $D_v(0.5)$ is about 75 µm.

In some embodiments, the ratios of Dv(0.9):Dv(0.5) and Dv(0.5):Dv(0.1) are each independently <2. In another embodiment, the ratio of Dv(0.9):Dv(0.5) is about two or less and the ratio of Dv(0.5):Dv(0.1) is about five or less. In yet another embodiment, the ratio of Dv(0.9):Dv(0.5) is <1.8. In another embodiment, the ratio of Dv(0.9):Dv(0.5) is about 2.0. In yet another embodiment, the ratio of Dv(0.9):Dv(0.5) is about 1.8. In another embodiment, the ratio of Dv(0.9):Dv(0.5) is about 1.6.

In another embodiment, the ratio of Dv(0.5):Dv(0.1) is <2.0. In yet another embodiment, Dv(0.5):Dv(0.1) is <1.9. In another embodiment, the ratio of Dv(0.5):Dv(0.1) is about 2.0. In yet another embodiment, the ratio of Dv(0.5):Dv(0.1) is about 1.8. In another embodiment, the ratio of Dv(0.9):Dv(0.5) is about 1.6.

In another embodiment, the ratio of Dv(0.9):Dv(0.5) is <5.0 and the ratio of Dv(0.5):Dv(0.1) is <5.0. In yet another embodiment, the ratio of Dv(0.9):Dv(0.5) is <2.0 and the ratio of Dv(0.5):Dv(0.1) is <2.0. In another embodiment, the ratio of Dv(0.9):Dv(0.5) is <1.8 and the ratio of Dv(0.5):Dv(0.1) is <1.8. In another embodiment, the ratio of Dv(0.9):Dv(0.5) is <1.6 and the ratio of Dv(0.5):Dv(0.1) is <2.0.

In some embodiments, the $D_v50$ is about 75 µm. In some embodiments, $D_v(0.5)$ is between about 30 and 100 µm. More preferably, $D_v(0.5)$ is between about 60 and 90 µm. In these embodiments, $D_v(0.1)$ is between about 10 and 80 µm, more preferably between about 30 and 60 µm, and $D_v(0.9)$ is between about 80 and 150 µm, more preferably between about 90 and 120 µm. In another embodiment, Dv(0.5) is between about 60 and 90 µm. In another embodiment, Dv(0.5) is between about 70 and 80 µm. In one embodiment, the ratios of Dv(0.9):Dv(0.5) and Dv(0.5):Dv(0.1) are each independently less than about two. In one embodiment, the ratio of Dv(0.9):Dv(0.5) is about two or less and the ratio of Dv(0.5):Dv(0.1) is about five or less.

In other embodiments, $D_v(0.5)$ is between about 1 and 25 µm, more preferably between about 5 and 20 µm. In these embodiments, $D_v(0.1)$ is between about 1 and 10 µm, more preferably between about 2 and 6 µm, and $D_v(0.9)$ is between about 5 and 50 µm, more preferably between about 20 and 35 µm. In another embodiment, Dv(0.5) is between about 5 and 20 µm. In another embodiment, Dv(0.5) is between about 10 and 20 µm. In another embodiment, Dv(0.5) is about 15 µm. In one embodiment, the ratios of Dv(0.9):Dv(0.5) and Dv(0.5):Dv(0.1) are each independently less than about two. In one embodiment, the ratio of Dv(0.9):Dv(0.5) is about two or less and the ratio of Dv(0.5):Dv(0.1) is about five or less.

In some embodiments, the particle size distribution is relatively narrow. For example, 90% of the particles are within the range of 10 µm to 25 µm. In some embodiments, particles are essentially monodisperse with controlled sized from about 5-10 µm.

It has been theorized that small particles, less than 3 µm in diameter, could potentially be absorbed into a patient's bloodstream resulting in undesirable effects such as the accumulation of particles in the urinary tract of the patient, and particularly in the patient's kidneys. Following ingestion, translocation of particles into and across the gastrointestinal mucosa can occur via four different pathways: 1) endocytosis through epithelial cells; 2) transcytosis at the M-cells located in the Peyer's Patches (small intestinal lymphoid aggregates), persorption (passage through "gaps" at the villous tip) and 4) putative paracellular uptake (Powell, J. J. et al *Journal of Autoimmunity* 2010, 34, J226-J233). The most documented and common route of uptake for micro particles is via the M-cell rich layer of Peyer's Patches, especially for small microparticles on the order of 0.1 to 0.5 µm in size (Powell, *Journal of Autoimmunity* 2010). Thus, excessively small particles, often called the "fines," should be controlled during the polymer manufacturing process. The presence of such fine particulate matter could present a safety challenge, and at minimum would impact the non-absorbed nature of the polymeric drug and associated safety advantages.

In another aspect of the invention, the swelling ratios of the polymer particles have been optimized. In some embodiments, polymers have a swelling ratio of less than about 10 grams of water per gram of polymer and more than about 2 grams of water per gram of polymer. In another embodiment, the polymer particles have a swelling ratio of less than about 7 grams of water per gram of polymer, but greater than about 2 grams of water per gram of polymer. In yet another embodiment, the swelling ratio is less than about 4.5 grams of water per gram of polymer, and more than about 3 grams of water per gram of polymer.

In some embodiments, the polymers have a swelling ratio in water of between about 3 grams of water per gram of polymer to about 8 grams of water per gram of polymer. In another embodiment, the polymers have a swelling ratio in water of between about 3 grams of water per gram of polymer to about 4.5 grams of water per gram of polymer. In yet another embodiment, the polymers have a swelling ratio in water of about 4.3 grams of water per gram of polymer. In another embodiment, the polymers have a swelling ratio in water of between about 3.5 to about 6.5 grams of water per gram of polymer. In another embodiment, the polymers have a swelling ratio in water of between about 4.0 to about 6.0 grams of water per gram of polymer. In another embodiment, the polymers have a swelling ratio in water of between about 4.0 to about 5.8 grams of water per gram of polymer.

In some embodiments, the potassium binding polymer is characterized by a swelling ratio in water of between about 3 grams of water per gram of polymer to about 8 grams of water per gram of polymer. In another embodiment, the potassium binding polymer is characterized by a swelling ratio in water of between about 3 grams of water per gram of polymer to about 4.5 grams of water per gram of polymer. In yet another embodiment, the potassium binding polymer is characterized by a swelling ratio in water of about 3.3 grams of water per gram of polymer. In another embodiment, the potassium binding polymer is characterized by a swelling ratio in water of about 4.3 grams of water per gram of polymer.

The present invention provides a method of removing potassium and/or treating hyperkalemia in an animal subject in need thereof, comprising administering an effective amount once, twice or three times per day to the subject of a crosslinked cation exchange polymer in the form of substantially spherical particles having a well-defined particle size distribution and a preferred swelling ratio in water. The particle shape, size distribution and swelling ratio of the polymer is chosen to not only increase the amount of potassium that can be diverted into the feces in an animal subject consuming said polymer, but these physical properties also improve the palatability (mouth feel, taste, etc.) of the polymer when it is ingested by a subject in need thereof. Preferred physical properties include a generally spherical shape of the particles, a well-defined particle size distribution with the smallest particles typically no smaller than 1-2 μm and the largest particles typically no larger than 100-120 μm, and a swelling ratio between about 2 grams of water per gram of polymer to 6 grams of water per gram of polymer when measured in water with the polymer in the calcium salt form.

Generally, the potassium binding polymers described herein are not absorbed from the gastrointestinal tract. The term "non-absorbed" and its grammatical equivalents (such as "non-systemic," "non-bioavailable," etc.) is not intended to mean that the polymer cannot be detected outside of the gastrointestinal tract. It is anticipated that certain amounts of the polymer may be absorbed. For example, about 90% or more of the polymer is not absorbed, more particularly, about 95% of the polymer is not absorbed, and more particularly still about 98% or more of the polymer is not absorbed.

In some embodiments, the potassium-binding polymers described herein are crosslinked cation exchange polymers (or "resins") derived from at least one crosslinker and at least one monomer. The monomer (or crosslinker) can contain an acid group in several forms, including protonated or ionized forms, or in a chemically protected form that can be liberated ("deprotected") later in the synthesis of the polymer. Alternatively, the acid group can be chemically installed after first polymerizing the crosslinker and monomer groups. Acid groups can include sulfonic, sulfuric, carboxylic, phosphonic, phosphoric or sulfamic groups, or combinations thereof. In general, the acidity of the group should be such that, at physiological pH in the gastrointestinal tract of the subject in need, the conjugate base is available to interact favorably with potassium ions.

The polymer of the present invention can be characterized by a crosslinking of between about 0.5% to about 6%. In some embodiments, the polymer is characterized by a crosslinking of less than 6%. In another embodiment, the polymer is characterized by a crosslinking of less than 5%. In yet another embodiment, the polymer is characterized by a crosslinking of less than 3%. In another embodiment, the polymer is characterized by a crosslinking of about 1.8%, wherein the term "about" means ±20%. In yet another embodiment, the polymer is characterized by a crosslinking of about 1.8%, wherein the term "about" means ±10%. In another embodiment, the polymer is characterized by a crosslinking of about 1.8%, wherein the term "about" means ±5%. In other embodiments, the polymer is characterized by a crosslinking of 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, or 5.0%.

The ratio of monomer(s) to crosslinker(s) can be chosen to affect the physical properties of the polymer. Additional factors include the time of addition of the crosslinker, the time and temperature of the polymerization reaction, the nature of the polymerization initiator, the use of different additives to help modulate agglomeration of the growing polymer or otherwise stabilize reactants prior to, or during, the polymerization process. The ratio of the monomer(s) and crosslinker(s), or the "repeat units," can be chosen by those of skill in the art based on the desired physical properties of the polymer particles. For example, the swelling ratio can be used to determine the amount of crosslinking based on general principles that indicate that as crosslinking increases, the selling ratio in water generally decreases. In one specific embodiment, the amount of crosslinker in the polymerization reaction mixture is in the range of 1 wt. % to 10 wt. %, more specifically in the range of 1 wt. % to 8 wt. %, and even more specifically in the range of 1.8 wt. % to 2.5 wt. %. To one skilled in the art, these weight ratios can be converted to mole ratios—based on the molecular weights of said monomers—and these mole-based calculations can be used to assign numerical values to "m" and "n" in (Formula I). It is also noted that to one skilled in the art that in practice, individual monomers can react at different rates and hence their incorporation into the polymer is not necessarily quantitative. With this in mind, the amount of crosslinker in the polymerization reaction mixture is in the range of 1 mole % to 8 mole %, more specifically in the range of 1 mole % to 7 mole %, and even more specifically in the range of 1.5 mole % to 2 mole %.

In another aspect of the invention, the polymers of the invention have a mouth feel score greater than 3. In some embodiments, the polymers have a mouth feel score greater than 3.5. In another embodiment, the polymers have a mouth feel score greater than 4.0. In yet another embodiment, the polymers have a mouth feel score greater than 5.0. In another embodiment, the polymers of the invention have a mouth feel score of between about 3.0 to about 6.0. In yet another embodiment, the polymers of the invention have a mouth feel score of between about 4.0 to about 6.0. In another embodiment, the polymers of the invention have a mouth feel score of between about 5.0 to about 6.0.

The polymers of the invention can also have a grittiness score that is greater than 3. In some embodiments, the polymers have a grittiness score greater than 3. In another embodiment, the polymers have a grittiness score greater than 4. In yet another embodiment, the polymers have a grittiness score greater than 4.5. In another embodiment, the polymers have a grittiness score greater than 5. In another embodiment, the polymers have a grittiness score greater than 5.5. In yet another embodiment, the polymers have a grittiness score of between about 3.0 to about 6.0. In yet another embodiment, the polymers have a grittiness score of between about 3.5 to about 6.0. In yet another embodiment, the polymers have a grittiness score of between about 4.5 to about 6.0

Definitions

"Amino" refers to the —$NH_2$ radical.
"Aminocarbonyl" refers to the —C(=O)$NH_2$ radical.
"Carboxy" refers to the —$CO_2H$ radical. "Carboxylate" refers to a salt or ester thereof.
"Cyano" refers to the —CN radical.
"Hydroxy" or "hydroxyl" refers to the —OH radical.
"Imino" refers to the =NH radical.
"Nitro" refers to the —$NO_2$ radical.
"Oxo" or "carbonyl" refers to the =O radical.
"Thioxo" refers to the =S radical.
"Guanidinyl" (or "guanidine") refers to the —NHC(=NH)$NH_2$ radical.
"Amidinyl" (or "amidine") refers to the —C(=NH)$NH_2$ radical.
"Phosphate" refers to the —OP(=O)$(OH)_2$ radical.
"Phosphonate" refers to the —P(=O)$(OH)_2$ radical.
"Phosphinate" refers to the —PH(=O)OH radical, wherein each $R^a$ is independently an alkyl group as defined herein.
"Sulfate" refers to the —OS(=O)$_2$OH radical.
"Sulfonate" or "hydroxysulfonyl" refers to the —S(=O)$_2$OH radical.
"Sulfinate" refers to the —S(=O)OH radical.
"Sulfonyl" refers to a moiety comprising a —$SO_2$— group. For example, "alkysulfonyl" or "alkylsulfone" refers to the —$SO_2$—$R^a$ group, wherein $R^a$ is an alkyl group as defined herein.
"Alkyl" refers to a straight or branched hydrocarbon chain radical consisting solely of carbon and hydrogen atoms, which is saturated or unsaturated (i.e., contains one or more double and/or triple bonds), having from one to twelve carbon atoms ($C_{1-12}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Unless stated otherwise specifically in the specification, an alkyl group may be optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted.

"Alkoxy" refers to a radical of the formula —$OR_a$ where $R_a$ is an alkyl radical as defined above containing one to twelve carbon atoms. Unless stated otherwise specifically in the specification, an alkoxy group may be optionally substituted.

"Alkylamino" refers to a radical of the formula —$NHR_a$ or —$NR_aR_a$ where each $R_a$ is, independently, an alkyl radical as defined above containing one to twelve carbon atoms. Unless stated otherwise specifically in the specification, an alkylamino group may be optionally substituted.

"Thioalkyl" refers to a radical of the formula —$SR_a$ where $R_a$ is an alkyl radical as defined above containing one to twelve carbon atoms. Unless stated otherwise specifically in the specification, a thioalkyl group may be optionally substituted.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may include fused or bridged ring systems. Unless stated otherwise specifically in the specification, the term "aryl" or the prefix "ar-" (such as in "aralkyl") is meant to include aryl radicals that are optionally substituted.

"Aralkyl" refers to a radical of the formula —$R_b$—$R_c$ where $R_b$ is an alkylene chain as defined above and R, is one or more aryl radicals as defined above, for example, benzyl, diphenylmethyl and the like. Unless stated otherwise specifically in the specification, an aralkyl group may be optionally substituted.

"Cycloalkyl" or "carbocyclic ring" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Unless otherwise stated specifically in the specification, a cycloalkyl group may be optionally substituted.

"Cycloalkylalkyl" refers to a radical of the formula —$R_bR_d$ where $R_d$ is an alkylene chain as defined above and $R_g$ is a cycloalkyl radical as defined above. Unless stated otherwise specifically in the specification, a cycloalkylalkyl group may be optionally substituted.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above that is substituted by one or more halo radicals, as defined above. Unless stated otherwise specifically in the specification, a haloalkyl group may be optionally substituted.

"Heterocyclyl" or "heterocyclic ring" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Unless stated otherwise specifically in the specification, a heterocyclyl group may be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group may be optionally substituted.

"Heterocyclylalkyl" refers to a radical of the formula —$R_b R_e$ where $R_b$ is an alkylene chain as defined above and $R_e$ is a heterocyclyl radical as defined above, and if the heterocyclyl is a nitrogen-containing heterocyclyl, the heterocyclyl may be attached to the alkyl radical at the nitrogen atom. Unless stated otherwise specifically in the specification, a heterocyclylalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Unless stated otherwise specifically in the specification, a heteroaryl group may be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group may be optionally substituted.

"Heteroarylalkyl" refers to a radical of the formula —$R_b R_f$ where $R_b$ is an alkylene chain as defined above and $R_f$ is a heteroaryl radical as defined above. Unless stated otherwise specifically in the specification, a heteroarylalkyl group may be optionally substituted.

The term "substituted" used herein means any of the above groups (i.e., alkyl, alkylene, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, carboxyl groups, phosphate groups, sulfate groups, alkoxy groups, and ester groups; a sulfur atom in groups such as thiol groups, thioalkyl groups, sulfinate groups, sulfone groups, sulfonyl groups, and sulfoxide groups; a phosphorus atom in groups such as phosphinate groups and phosphonate groups; a nitrogen atom in groups such as guanidine groups, amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_g R_h$, —$NR_g C(=O)R_h$, —$NR_g C(=O)NR_g R_h$, —$NR_g C(=O)OR_h$, —$NR_g SO_2 R_h$, —$OC(=O)NR_g R_h$, —$OR_g$, —$SR_g$, —$SOR_g$, —$SO_2 R_g$, —$OSO_2 R_g$, —$SO_2 OR_g$, =$NSO_2 R_g$, and —$SO_2 NR_g R_h$. "Substituted" also means any of the above groups in which one or more hydrogen atoms are replaced with —$C(=O)R_g$, —$C(=O)OR_g$, —$C(=O)NR_g R_h$, —$CH_2 SO_2 R_g$, —$CH_2 SO_2 NR_g R_h$, —$(CH_2 CH_2 O)_{1-10} R_g$, —$(CH_2 CH_2 O)_{2-10} R_g$, —$(OCH_2 CH_2)_{1-10} R_g$ and —$(OCH_2 CH_2)_{2-10} R_g$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. The above non-hydrogen groups are generally referred to herein as "substituents" or "non-hydrogen substituents". In addition, each of the foregoing substituents may also be optionally substituted with one or more of the above substituents.

By "crosslink" and "crosslinking" is meant a bond or chain of atoms attached between and linking two different polymer chains.

The articles "a" and "an" are used herein to refer to one or to more than one (i.e., to at least one) of the grammatical object of the article. By way of example, "an element" means one element or more than one element.

Unless specifically stated, as used herein, the term "about" refers to a range of values ±10% of a specified value. For example, the phrase "about 200" includes ±10% of 200, or from 180 to 220. When stated otherwise the term about will refer to a range of values that include ±20%, ±10%, or ±5%, etc.

The term "activate" refers to the application of physical, chemical, or biochemical conditions, substances or processes that a receptor (e.g., pore receptor) to structurally change in a way that allows passage of ions, molecules, or other substances.

The term "active state" refers to the state or condition of a receptor in its non-resting condition.

"Efflux" refers to the movement or flux of ions, molecules, or other substances from an intracellular space to an extracellular space.

"Enteral" or "enteric" administration refers to administration via the gastrointestinal tract, including oral, sublingual, sublabial, buccal, and rectal administration, and including administration via a gastric or duodenal feeding tube.

The term "inactive state" refers to the state of a receptor in its original endogenous state, that is, its resting state.

The term "modulating" includes "increasing" or "enhancing," as well as "decreasing" or "reducing," typically in a statistically significant or a physiologically significant amount as compared to a control. An "increased" or "enhanced" amount is typically a "statistically significant" amount, and may include an increase that is about 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.2, 3.4, 3.6, 3.8, 4.0, 4.2, 4.3, 4.4, 4.6, 4.8, 5, 6, 7, 8, 9, 10, 15, 20, 30, 40, 50 or more times (e.g., 100, 200, 500, 1000 times) (including all integers and decimal points and ranges in between and above 1, e.g., 5.5, 5.6, 5.7, 5.8, etc.) the amount produced by a control (e.g., the absence or lesser amount of a compound, a different compound or treatment), or the amount of an earlier time-point (e.g., prior to treatment with a compound). A "decreased" or "reduced" amount is typically a "statistically significant" amount, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease (including all integers and decimal points and ranges in between) in the amount or activity produced by a control (e.g., the absence or lesser amount of a compound, a different compound or treatment), or the amount of an earlier time-point (e.g., prior to treatment with a compound).

"Mammal" includes humans and both domestic animals such as laboratory animals and household pets (e.g., cats, dogs, swine, cattle, sheep, goats, horses, rabbits), and non-domestic animals such as wildlife and the like.

The term "mouthfeel" of a substance according to the present invention is the tactile sensations perceived at the lining of the mouth, including the tongue, gums and teeth.

"Optional" or "optionally" means that the subsequently described event or circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Stable compound" and "stable structure" are meant to indicate a compound that is sufficiently robust to survive isolation to a useful degree of purity from a reaction mixture, and formulation into an efficacious therapeutic agent.

By "statistically significant," it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

"Substantially" or "essentially" includes nearly totally or completely, for instance, 80%, 85%, 90%, 95%, 96%, 97%, 98%, 99% or greater of some given quantity.

The term "secondary" refers to a condition or state that can occur with another disease state, condition, or treatment, can follow on from another disease state, condition, or treatment, or can result from another disease state, condition or treatment. The term also refers to situations where a disease state, condition, or treatment can play only a minor role in creating symptoms or a response in a patient's final diseased state, symptoms or condition.

"Subjects" or "patients" (the terms are used interchangeably herein) in need of treatment with a compound of the present disclosure include, for instance, subjects "in need of potassium lowering." Included are mammals with diseases and/or conditions described herein, particularly diseases and/or conditions that can be treated with the compounds of the invention, with or without other active agents, to achieve a beneficial therapeutic and/or prophylactic result. A beneficial outcome includes a decrease in the severity of symptoms or delay in the onset of symptoms, modulation of one or more indications described herein (e.g., reduced potassium ion levels in serum or blood of patients with or at risk for hyperkalemia, increased fecal output of potassium ions in patients with or at risk for hyperkalemia), increased longevity, and/or more rapid or more complete resolution of the disease or condition.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

A "therapeutically effective amount" or "effective amount" includes an amount of a compound of the invention which, when administered to a mammal, preferably a human, is sufficient to increase fecal output of potassium ions, reduce serum levels of potassium ions, treat hyperkalemia in the mammal, preferably a human, and/or treat any one or more other conditions described herein. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;
(ii) inhibiting the disease or condition, i.e., arresting its development;
(iii) relieving the disease or condition, i.e., causing regression of the disease or condition; or
(iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

Methods of Making the Potassium Binding Crosslinked Polymers

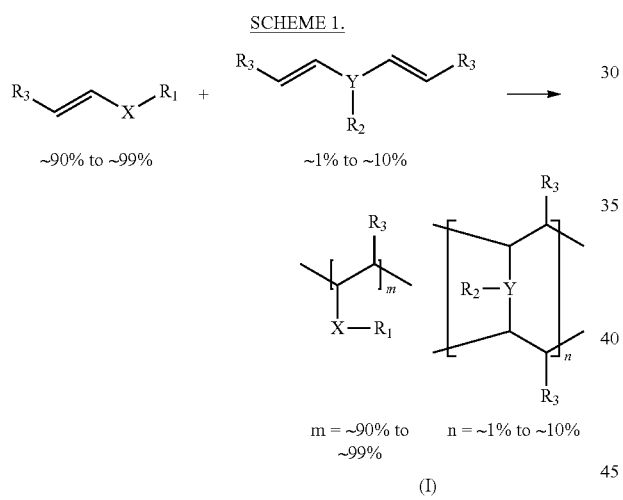

SCHEME 1.

Copolymerization of an organic monomer "$R_1$—X" displaying a single olefin with a "crosslinker" organic monomer "$R_2$—Y" that displays two olefins.

Scheme 1 illustrates the copolymerization of an organic monomer displaying a single olefin ($R_1$—X—CH=CH—$R_3$) with a second organic monomer displaying two olefin groups ($R_2$—Y—(CH=CH—$R_3$)$_2$; a crosslinker). $R_1$ and $R_2$ can be —H, acidic functional groups such as sulfonic, sulfuric, carboxylic, phosphonic, phosphoric or sulfamic groups, or combinations thereof, or substituted or unsubstituted alkyl or aryl radicals. $R_3$ can be —H, halogen, acidic functional groups such as sulfonic, sulfuric, carboxylic, phosphonic, phosphoric or sulfamic groups, or combinations thereof, or substituted or unsubstituted alkyl or aryl radicals. X and Y can be the same or different, and can be substituted or unsubstituted alkyl or aryl radicals. More preferably, $R_1$—X represents an aromatic group, and $R_2$—Y represents an aromatic group. Most preferably, $R_1$—X is phenyl and $R_2$—Y is phenyl and $R_3$ is —H—hence $R_1$—X—CH=CH—$R_3$ is styrene and $R_2$—Y—(CH=CH—$R_3$)$_2$ is divinylbenzene. Divinylbenzene can be ortho-, meta- or para-divinylbenzene, and is most commonly a mixture of two or three of these isomers. When $R_1$—X is phenyl, $R_2$—Y is phenyl and $R_3$ is —H, the resulting polymer is further modified to display acidic functionality capable of binding to potassium ions. In a preferred embodiment, the polymer is sulfonated by treatment with concentrated sulfuric acid, optionally using a catalyst such as silver sulfate. The resulting sulfonylated material can be retained in its acid form, or alternatively treated with base and converted to a salt form. This salt form can include metal salts such as sodium, calcium, magnesium or iron salts. These can also be organic salts, including salts of amines or amino acids and the like. In a preferred embodiment, the calcium salt is formed. In this preferred embodiment, (I) in Scheme 1 consists of X=Y=phenyl (Ph), $R_1$=$R_2$=—SO$_3^-$[0.5 Ca$^{2+}$], and $R_3$ is —H. In this preferred embodiment, the ratio of m to n (m:n) is about:11:1 to about 120:1, more preferably about 14:1, more preferably still about 40:1, and most preferably about 50:1, about 60:1, and about 70:1.

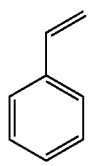

Formula 1

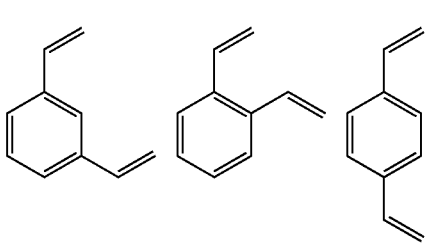

Formula 2

In one embodiment, the polymer is prepared from structural units of Formula 1 (e.g. styrene) and Formula 2 (e.g., divinylbenzene), which afford a polystyrene divinylbenzene copolymer intermediate. The weight ratio of the structural units of Formula 1 to Formula 2 is such that the polymer consists of about 90% Formula 1 and 10% of Formula 2. It should be noted, that in most cases, Formula 2 can be a mixture. In the case of divinylbenzene, the ortho, meta, and para positional isomers can be present Most preferable compositions include about 97.5% Formula 1 and 2.5% Formula 2, 98% Formula 1 and 2% Formula 2, and 98.2% Formula 1 and 1.8% Formula 2, by weight. Scheme 2 illustrates a copolymerization of this description, where "m" and "n" in the product reflect the varying amounts of styrene (m) and divinylbenzene (n).

SCHEME 2.

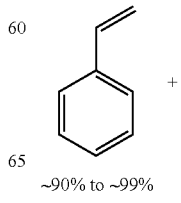

~90% to ~99%

-continued

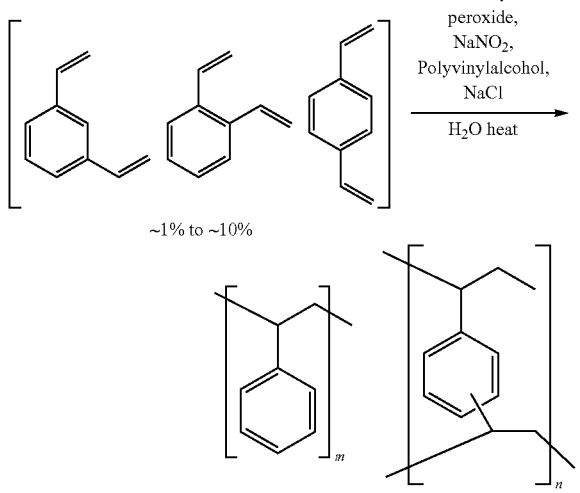

In one embodiment, the polymerization initiator used in the suspension polymerization plays a role in the quality of the polymer particles, including yield, shape and other physical attributes. Without being bound to a particular theory, the use of water-insoluble free radical initiators, such as benzoyl peroxide, initiates polymerization primarily within the phase containing the monomers. Such a reaction strategy provides polymer particles rather than a bulk polymer gel. Other suitable free radical initiators include other peroxides such as lauroyl peroxide (LPO), tert-butyl hydro peroxide, and the like. Azo type initiators commonly include azobisisobutyronitrile (AIBN), but also used are dimethyl-2,2'-azobis(2-methyl-proprionate), 2,2''-azo bis(2,4-dimethylvaleronitrile) and the like. These agents initiate the polymerization process.

Additional polymerization components that are not intended to be incorporated into the polymer include additives such as surfactants, solvents, salts, buffers, aqueous phase polymerization inhibitors and/or other components known to those of skill in the art. When the polymerization is carried out in a suspension mode, the additional components may be contained in an aqueous phase while the monomers and initiator may be contained in an organic phase. A surfactant may be selected from the group consisting of anionic, cationic, nonionic, amphoteric or zwitterionic, or a combination thereof. Anionic sufactants are typically based on sulfate, sulfonate or carboxylate anions and include sodium dodecyl sulfate (SDS), ammonium lauryl sulfate, other alkyl sulfate salts, sodium laureth sulfate (or sodium lauryl ether sulfate (SLES)), N-lauroylsarcosine sodium salt, lauryldimethylamine-oxide (LDAO), ethyltrimethylammoniumbromide (CTAB), bis(2-ethylhexyl)sulfosuccinate sodium salt, alkyl benzene sulfonate, soaps, fatty acid salts, or a combination thereof. Cationic surfactants, for example, contain quaternary ammonium cations. These surfactants are cetyl trimethylammonium bromide (CTAB or hexadecyl trimethyl ammonium bromide), cetylpyridinium chloride (CPC), polyethoxylated tallow amine (POEA), benzalkonium chloride (BAC), benzethonium chloride (BZT), or a combination thereof. Zwitterionic or amphoteric surfactants include dodecyl betaine, dodecyl dimethylamine oxide, cocamidopropyl betaine, coco ampho glycinate, or a combination thereof. Nonionic surfactants include alkyl poly(ethylene oxide), copolymers of poly(ethylene oxide) and poly(propylene oxide) (commercially called Poloxamers or Poloxamines), alkyl polyglucosides (including octyl glucoside, decyl maltoside), fatty alcohols, cetyl alcohol, oleyl alcohol, cocamide MEA, cocamide DEA, or a combination thereof. Other pharmaceutically acceptable surfactants are well known in the art and are described in McCutcheon's Emulsifiers and Detergents, N. American Edition (2007).

Polymerization reaction stabilizers may be selected from the group consisting of organic polymers and inorganic particulate stabilizers. Examples include polyvinyl alcohol-co-vinyl acetate and its range of hydrolyzed products, polyvinylacetate, polyvinylpyrrolidinone, salts of polyacrylic acid, cellulose ethers, natural gums, or a combination thereof. Buffers may be selected from the group consisting of 4-2-hydroxyethyl-1-piperazineethanesulfonic acid, 2-{[tris(hydroxymethyl)methyl]amino}ethanesulfonic acid, 3-(N-morpholino)propanesulfonic acid, piperazine-N,N'-bis(2-ethanesulfonic acid), sodium phosphate dibasic heptahydrate, sodium phosphate monobasic monohydrate or a combination thereof.

Generally, the mixture of monomers and additives are subjected to polymerization conditions. These can include suspension polymerization conditions as well as bulk, solution or emulsion polymerization processes. The polymerization conditions typically include polymerization reaction temperatures, pressures, mixing and reactor geometry, sequence and rate of addition of polymerization mixtures and the like. Polymerization temperatures are typically in the range of about 50° C. to 100° C. Polymerizations are typically performed at atmospheric pressures, but can be run at higher pressures (for example 130 PSI of nitrogen). Mixing depends upon the scale of the polymerization and the equipment used, but can include agitation with the impeller of a reactor to the use of immersion or in-line homogenizers capable of creating smaller droplets under certain conditions.

In one embodiment, polymerization can be achieved using a suspension polymerization approach. Suspension polymerization is a heterogeneous radical polymerization process. In this approach, mechanical agitation is used to mix a monomer or mixture of monomers in an immiscible liquid phase, such as water. While the monomers polymerize, they retain their nearly spherical suspension shape, forming spheres of polymer. Polymerization suspension stabilizers, such as polyvinyl alcohol, can be used to prevent coalescence of particles during the polymerization process. Factors such as the ratio of monomers to cross linker, agitation speed, ionic strength of the liquid phase, the nature of the suspension stabilizer, etc., contribute to the yield, shape, size and other physical properties of the polymer.

In one embodiment, highly uniform sized particles can be produced via a multi-step approach inspired by Ugelstad (Ugelstad_1979). In this approach, "seeds" are first prepared by dispersion polymerization of styrene in the presence of a steric stabilizer such as polyvinylpyrrolidone, using an initiator such as AIBN, and using a water/alcohol polymerization medium. The seeds are isolated, and then swollen with a monomer-initiator solution containing additional styrene as well as divinylbenzene and BPO, and then polymerized to give highly uniform styrene-divinylbenzene beads. Alternatively, a jetting process using vibrating nozzles can also be used to create microdispersed droplets of monomers, and in this fashion permit the synthesis of highly uniform crosslinked polymer beads (Dow Chemical, U.S. Pat. No. 4,444,961.)

In another embodiment, the crosslinked styrene-sulfonate particles of the invention can be produced by an inverse suspension process, wherein a solution of styrene-sulfonate, a water soluble crosslinker and a free-radical initiator are dispersed in an organic solvent and converted to crosslinked beads.

The polymers illustrated in Scheme 1 and Scheme 2 are most preferably sulfonylated, and the resulting sulfonic acid converted to a pharmaceutically acceptable salt. Scheme 3 illustrates the sulfonation of a preferred embodiment. The resulting sulfonic acid can be further treated with calcium acetate to afford the calcium salt. At the physiological pH within the gastrointestinal tract of a subject in need, the conjugate base of the sulfonic acid is available to interact favorably with potassium ions. By interacting favorably, this means binding to or otherwise sequestering potassium cations for subsequent fecal elimination.

SCHEME 3.

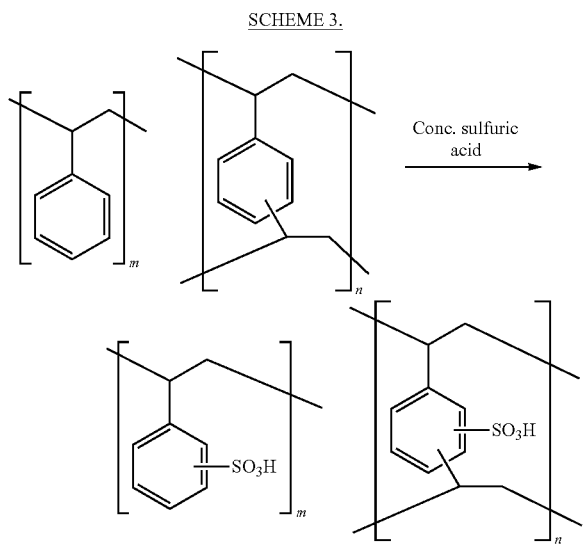

Polymer Sulfonylation

Resins comprising the general structure of polystyrene sulfonate cross linked with divinylbenzene are available and used clinically, e.g., Kayexalate®, Argamate®, Kionex® and Resonium®. However, these resins do not possess the optimized cross-linking, particle shape, particle size distribution, and swelling properties as do the novel polymers described herein. For example, the crosslinked cation exchange polymers described in this invention generally have a higher efficacy for potassium in vivo than resins such as Kayexalate. When healthy rodents are administered the polymers of the present invention, approximately 1.4- to 1.5-fold more potassium is excreted fecally than is achieved when, for example, Resonium is similarly dosed (same dosing and fecal collection conditions). In some embodiments, approximately 2.0-fold more potassium is excreted fecally than is achieved when, for example, Na-PSS, USP (e.g. Kayexylate) is similarly dosed (same dosing and fecal collection conditions). The higher capacity of the polymers of this invention may enable the administration of a lower dose of the polymer. Typically, the dose of Na-PSS or Ca-PSS used clinically to obtain the desired therapeutic and/or prophylactic benefits is about 10 to 60 grams/day and can be as high as 120 g/day. A typical dose range is 10-20 g, 30-40 g and 45-120 g, which can be divided into one, two or three doses/day (Fordjour, Am. J. Med. Sci. 2014). The polymers of the current invention could permit a significant reduction in drug load for the patient.

Methods of Using Potassium Binding Crosslinked Polymers

Patients suffering from CKD and/or CHF can be particularly in need of potassium removal because agents used to treat these conditions may cause potassium retention. Many of these subjects are also taking medications that interfere with potassium excretion, e.g., potassium-sparing diuretics, RAAS inhibitors, beta blockers, aldosterone synthase inhibitors, non-steroidal anti-inflammatory drugs, heparin, or trimethoprim. In certain particular embodiments, the polymers of the present invention can be administered on a periodic basis to treat chronic hyperkalemia. Such a treatment would enable patients to continue using drugs that may cause hyperkalemia. Also, use of the polymer compositions described herein will enable patient populations, who were previously unable to use the above-listed medications, to being treatable with these beneficial therapeutics.

The cation exchange polymers described herein can be delivered to the patient using a wide variety of routes or modes of administration. The most preferred routes are oral, intestinal (e.g., via gastrointestinal tube) or rectal. Rectal routes of administration are known to those of skill in the art. The most preferred route for administration is oral.

The polymers described herein can be administered as neat, dry powders or in the form of a pharmaceutical composition wherein the polymer is in admixture with one or more pharmaceutically acceptable excipients. These can include carriers, diluents, binder, disintegrants and other such generally-recognized-as-safe (GRAS) excipients designed to present the active ingredient in a form convenient for consumption by the patient. The nature and composition of these excipients are dependent upon the chosen route of administration.

For oral administration, the polymer can be formulated by combining the polymer particles with pharmaceutically acceptable excipients well known in the art. These excipients can enable the polymer to be formulated as a suspension (including thixotropic suspensions), tablets, capsules, dragees, gels (including gummies or candies), syrups, slurries, wafers, liquids, and the like, for oral ingestion by a patient. In one embodiment, the oral composition does not have an enteric coating. Pharmaceutical preparations for oral use can be obtained as a solid excipient, optionally grinding a resulting mixture, and processing the mixture of granules, after adding suitable auxiliaries, if desired, to obtain tablets or dragee cores. Suitable excipients are, in particular, fillers such as sugars, including lactose or sucrose; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinyl pyrrolidone (PVP); and various flavoring agents known in the art. If desired, disintegrating agents may be added, such as the cross-linked polyvinyl pyrrolidone, agar, or alginic acid or a salt thereof such as sodium alginate.

In various embodiments, the active ingredient (e.g., the polymer) constitutes over about 10%, more particularly over about 30%, even more particularly over about 60%, and most particularly more than about 80% by weight of the oral dosage form, the remainder comprising suitable excipient(s).

In a certain formulation, the excipients would be chosen such that the polymers of the herein invention are well dispersed and suspended, such that any sensation of particulate matter on the palate is significantly blunted or eliminated. Such formulations could include, for example, suspension as a gel or paste in an aqueous matrix of agar, or gelatin, or pectin, or carrageenan, or a mixture of such agents. Such a formulation would be of a sufficient density to suspend the polymer particles in a non-settling matrix. Flavorings, such as sweeteners can be added, and these sweeteners can include both nutritive (malt extract, high-fructose corn syrup, and the like) and non-nutritive (e.g., aspartame, nutrasweet, and the like) agents, which can create a pleasant taste. Lipids such as tripalmitin, castor oil, sterotex, and the like, can be used to suspend particles in a way that avoids a foreign sensation on the palate, and can also lead to favorable flavor properties. Milk solids, cocoa butter and chocolate products can be combined to create a pudding or custard type mixture that both suspend the polymers of the invention, and also mask their contact on the palate. Formulations of the type described herein should be readily ingested presentations for the patient.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Example 1: Preparation of Calcium Polystyrene Sulfonate (Ca-PSS) with 8% DVB, 200-400 Mesh Size Crosslinked (8%) Polystyrene sulfonate beads (200-400 mesh size) in the acid form (H+) were obtained from Sigma-Adrich (Catalog #217514). The beads (100 g, wet weight) were suspended in aqueous NaOH (1M, 300 mL) and shaken for 20 hours at 27° C., then the mixture was filtered, and the wet beads washed with water (2×300 mL). The beads were suspended in aqueous $CaCl_2$ (0.5M, 700 mL) and shaken for 2 days at 37° C. The beads were then filtered, and suspended in fresh $CaCl_2$ (0.5M, 700 mL), and shaken for 2 days at 37° C. The beads were then filtered, washed successively with water (3×400 mL), and dried under reduced pressure to give 56.9 g of Example 1 as a fine light brown sand. Approximate particle size range of 30-120 μm determined by digital visual microscopy.

Example 2: Preparation of Calcium Polystyrene Sulfonate (Ca-PSS) with 4% DVB, 200-400 Mesh Size Example 2 was prepared from 100 g crosslinked (4%) polystyrene sulfonate beads (200-400 mesh), H+ form, obtained from Sigma-Adrich (Catalog #217484) using the procedures described in Example 1 to give 37.1 g of Example 2 as a fine light brown powder. Approximate particle size range of 30-130 μm determined by digital visual microscopy.

Example 3: Preparation of Calcium Polystyrene Sulfonate (Ca-PSS) with 2% DVB, 200-400 Mesh Size Example 3 was prepared from 100 g crosslinked (2%) polystyrene sulfonate beads (200-400 mesh), H+ form, obtained from Sigma-Aldrich (Catalog #217476) using the procedures described in Example 1 to give 21.8 g of Example 3 as a light brown sand: Particle size: $d_v(0.1)=90$ μm; $d_v(0.5)=120$ μm; $d_v(0.9)=170$ μm.

Example 4: Preparation of Calcium Polystyrene Sulfonate (Ca-PSS) with 2% DVB, 200-400 Mesh Size Crosslinked (2%) Polystyrene sulfonate beads (200-400 mesh size) in the acid form (H+) were obtained from Sigma-Aldrich (Catalog #217476). The beads (400 g, wet weight) were suspended in aqueous $CaCl_2$ (200 g $CaCl_2$, 1.8 L water) and shaken for 24 hours at 38° C., then the mixture was filtered. The beads were suspended in aqueous $Ca(OAc)_2$ (166 g, 2 L water) and shaken for 2 days at 37° C. The beads were then filtered, washed with water (1 L), and dried under reduced pressure to give Example 4 as a light brown sand. Approximate particle size range of 40-160 μm determined by digital visual microscopy.

Example 5: Preparation of Calcium Polystyrene Sulfonate (Ca-PSS) with 4% DVB, 200-400 Mesh Size Example 5 was prepared from 400 g crosslinked (4%) polystyrene sulfonate beads (200-400 mesh), H+ form, obtained from Sigma-Aldrich (Catalog #217484) using the procedures described in Example 4 to give Example 5 as a light brown sand. Approximate particle size range of 30-130 μm determined by digital visual microscopy.

Example 6: Preparation of Calcium Polystyrene Sulfonate (Ca-PSS) with 8% DVB, 200-400 Mesh Size Example 6 was prepared from 400 g crosslinked (8%) polystyrene sulfonate beads (200-400 mesh), H+ form, obtained from Sigma-Aldrich (Catalog #217514) using the procedures described in Example 4 to give Example 6 as a light brown sand. Approximate particle size range of 30-120 μm determined by digital visual microscopy.

Example 7: Preparation of Calcium Polystyrene Sulfonate (Ca-PSS) with 0.96% Divinylbenzene (DVB)

Intermediate Polystyrene beads at 0.96% DVB:
To a jacketed Morton style cylindrical vessel equipped with an overhead stirrer, thermocouple, and $N_2$ inlet was added polyvinyl alcohol (10 g), NaCl (10 g), $NaNO_2$ (0.2 g) and water (1 L). The mixture was stirred and heated to 70° C. for 1 hour to form a slightly turbid solution. In a separate container, styrene (75 mL), divinylbenzene (0.94 mL, 80% Technical Grade), and benzoyl peroxide (3 g, 98%) were mixed to form a homogeneous solution of monomers and initiator. The monomer-initiator solution was added to the hot aqueous solution and within 1-2 minutes a uniform white suspension was achieved with 600 RPM stirring. The mixture was heated to 85° C. for 18 hours, and then filtered while hot using a coarse fritted funnel. The solid polystyrene beads were suspended in water (700 mL), and heated at 85° C. for 1 hour. The mixture was then filtered while hot using a coarse fritted funnel, and the polystyrene beads were suspended in methanol (700 mL), and heated at reflux for 1 hour. The mixture was then filtered while still hot using a coarse fritted funnel, and dried in a vacuum oven to give 61 g of polystyrene beads as a white powder. Particle size estimated by visual microscopy d(50)=40 µm.

Example 7

To a 1 L round bottom flask, equipped with overhead stirrer, N$_2$ inlet, and a thermocouple was added silver sulfate (0.4 g) and sulfuric acid (98%, 300 mL). The mixture was warmed to 80° C. to dissolve, and then polystyrene beads (20 g) were added and the mixture stirred to form a suspension. The mixture was warmed to 100° C. for 3 hours, then poured into ice cold 50% aqueous H$_2$SO$_4$ (3 kg) The mixture was then diluted to a final volume of 5 L with water and allowed to stand overnight to settle. The dark supernatant was discarded, and the bead layer filtered using a coarse fritted funnel. The beads were washed with water until the pH of the filtrate was >4, as measured by pH indicator strips. The wet beads were then suspended in aqueous Ca(OAc)$_2$ (20% wt, 0.5 L) and shaken for 24 hours at 37° C., then the mixture was filtered, and the beads suspended in new aqueous Ca(OAc)$_2$ (20% wt, 0.5 L) and shaken again for 24 hours at 37° C. The beads were then washed successively with water (3×150 mL), and dried under reduced pressure at 50° C. to give 27.4 g of Example 7 Ca-PSS resin as a light brown sand. Swelling ratio in DI water: 9.1 g/g with relative centrifugal force of 2000×g; Residual Styrene: Not Detected (<0.1 ppm).

Example 8: Preparation of Calcium Polystyrene Sulfonate (Ca-PSS) with 1.12% Divinylbenzene (DVB)

Example 8 was prepared from styrene (75 mL), and divinylbenzene (1.1 mL, 80% Technical Grade) using the procedure described in Example 7 to give approximately 25 g of Example 8 Ca-PSS resin as a light brown sand. Swelling ratio in DI water: 7.9 g/g with relative centrifugal force of 2000×g; Residual Styrene: Not Detected (<0.1 ppm)

Example 9: Preparation of Calcium Polystyrene Sulfonate (Ca-PSS) with 1.6% Divinylbenzene (DVB)

Intermediate Polystyrene beads at 1.6% DVB:
To a jacketed Morton style cylindrical vessel equipped with an overhead stirrer, thermocouple, and N$_2$ inlet was added polyvinyl alcohol (10 g), NaCl (10 g), NaNO$_2$ (0.2 g) and water (1 L). The mixture was stirred and heated to 70° C. for 1 hour to form a slightly turbid solution. In a separate container, styrene (75 mL), divinylbenzene (1.5 mL, 80% Technical Grade), and benzoyl peroxide (3 g, 98%) were mixed to form a homogeneous solution of monomers and initiator. The monomer-initiator solution was added to the hot aqueous solution and within 1-2 minutes a uniform white suspension was achieved with 600 RPM stirring. The mixture was heated to 85° C. for 18 hours, and then filtered while hot using a coarse fritted funnel. The solid polystyrene beads were suspended in water (1 L), and heated at 85° C. for 1 hour. The mixture was then filtered while hot using a coarse fritted funnel, and the polystyrene beads were suspended in methanol (1 L), and heated at reflux for 1 hour. The mixture was then filtered while still hot using a coarse fritted funnel, and dried in a vacuum oven to give 61 g of polystyrene beads as a white powder. Particle size: d(0.1)=27 µm; d(0.5)=40 µm; d(0.9)=60 µm.

Example 9

To a 1 L round bottom flask, equipped with overhead stirrer, N$_2$ inlet, and a thermocouple was added silver sulfate (0.4 g) and sulfuric acid (98%, 300 mL). The mixture was warmed to 80° C. to dissolve, and then polystyrene beads (20 g) were added and the mixture stirred to form a suspension. The mixture was warmed to 100° C. for 3 hours, then poured into ice cold 50% aqueous H$_2$SO$_4$ (3 kg). The mixture was then diluted to a final volume of 5 L with water and allowed to stand overnight to settle. The dark supernatant was discarded, and the bead layer filtered using a coarse fritted funnel. The beads were washed with water until the pH of the filtrate was >4, as measured by pH indicator strips. A sample of wet beads were then suspended in aqueous Ca(OAc)$_2$ (20% wt, 1 L) and shaken for 24 hours at 37° C., then the mixture was filtered, and the beads suspended in new aqueous Ca(OAc)$_2$ (20% wt, 1 L) and shaken again for 24 hours at 37° C. The beads were then washed successively with water (3×150 mL), 50% EtOH-water (2×150 mL), 75% EtOH-water (2×150 mL), and 100% EtOH (2×150 mL), and dried under reduced pressure at 50° C. to give 31 g of Example 9 Ca-PSS resin as a light brown powder. Particle Size: d(0.1)=51 µm; d(0.5)=75 µm; d(0.9)=105 µm. Ca-salt (8.53 wt % by titration); Residual Styrene: Not Detected (<0.1 ppm).

Example 10: Preparation of Calcium Polystyrene Sulfonate (Ca-PSS) with 1.8% Divinylbenzene (DVB)

Intermediate Polystyrene beads at 1.8% DVB:
To a jacketed Morton style cylindrical vessel equipped with an overhead stirrer, thermocouple, and N$_2$ inlet was added polyvinyl alcohol (10 g), NaCl (10 g), NaNO$_2$ (0.2 g) and water (1 L). The mixture was stirred and heated to 70° C. for 1 hour to form a slightly turbid solution. In a separate container, styrene (150 mL), divinylbenzene (3.5 mL, 80% Technical Grade), and benzoyl peroxide (6 g, 98%) were mixed to form a homogeneous solution of monomers and initiator. The monomer-initiator solution was added to the hot aqueous solution and within 1-2 minutes a uniform white suspension was achieved with 600 RPM stirring. The mixture was heated to 91-94° C. for 18 hours, and then filtered while hot using a coarse fritted funnel. The solid polystyrene beads were suspended in water (1 L), and heated at 90° C. for 1 hour. The mixture was then filtered while hot using a coarse fritted funnel, and the polystyrene beads were suspended in isopropanol ("IPA") (1 L), and heated at reflux for 1 hour. The mixture was then filtered while still hot using a coarse fritted funnel, and dried in a vacuum oven to give 134 g of polystyrene beads as a white powder. Particle size: d$_v$(0.1)=30 µm; d$_v$(0.5)=40 µm; d$_v$(0.9)=60 µm.

Example 10

To a 1 L round bottom flask, equipped with overhead stirrer, N$_2$ inlet, and a thermocouple was added silver sulfate (0.44 g) and sulfuric acid (98%, 330 mL). The mixture was warmed to 80° C. to dissolve, and then polystyrene beads (22 g) were added and the mixture stirred to form a suspension. The mixture was warmed to 100° C. for 2 hours, then poured into ice cold 50% aqueous H$_2$SO$_4$ (2 kg) The mixture was then diluted to a final volume of 3.5 L with water and allowed to stand overnight to settle. The dark supernatant was discarded, and the bead layer filtered using a coarse fritted funnel. The beads were washed with water until the pH of the filtrate was >4, as measured by pH indicator strips. The wet beads were then suspended in aqueous Ca(OAc)$_2$ (20% wt, 1 L) and shaken for 24 hours at 37° C., then the mixture was filtered, and the beads suspended in new aqueous Ca(OAc)$_2$ (20% wt, 1 L) and shaken again for 24 hours at 37° C. The beads were then washed successively with water (2×1 L), 50% ethanol-water ("EtOH-water") (2×150 mL), 75% EtOH-water (2×150 mL), and 100% EtOH (2×150 mL), and dried under reduced pressure at 50° C. to give 35.5 g of Example 10 Ca-PSS resin as a fine light brown powder. Particle Size: d(0.1)=53 μm; d(0.5)=78 μm; d(0.9)=114 μm. Ca-salt (7.80 wt % by titration); K+ exchange capacity 1.6 mEq/g (per BP); Residual Styrene (2.1 ppm).

Example 11: Preparation of Calcium Polystyrene Sulfonate (Ca-PSS) with 2.0% Divinylbenzene (DVB)

Intermediate Polystyrene Beads at 2.0% DVB:

To a jacketed Morton style cylindrical vessel equipped with an overhead stirrer, thermocouple, and N$_2$ inlet was added polyvinyl alcohol (10 g), NaCl (10 g), NaNO$_2$ (0.2 g) and water (1 L). The mixture was stirred and heated to 70° C. for 1 hour to form a slightly turbid solution. In a separate container, styrene (75 mL), divinylbenzene (1.9 mL, 80% Technical Grade), and benzoyl peroxide (3 g, 98%) were mixed to form a homogeneous solution of monomers and initiator. The monomer-initiator solution was added to the hot aqueous solution and within 1-2 minutes a uniform white suspension was achieved with 600 RPM stirring. The mixture was heated to 85° C. for 24 hours, and then filtered while hot using a coarse fritted funnel. The solid polystyrene beads were suspended in water (700 ml), and heated at 85° C. for 1 hour. The mixture was then filtered while hot using a coarse fritted funnel, and the polystyrene beads were suspended in IPA (700 ml), and heated at reflux for 1 hour. The mixture was then filtered while still hot using a coarse fritted funnel, and dried in a vacuum oven to give 41.9 g of polystyrene beads as a white powder.

Example 11

To a 1 L round bottom flask, equipped with overhead stirrer, N$_2$ inlet, and a thermocouple was added silver sulfate (0.4 g) and sulfuric acid (98%, 300 mL). The mixture was warmed to 80° C. to dissolve, and then polystyrene beads (20 g) were added and the mixture stirred to form a suspension. The mixture was warmed to 100° C. for 3 h, then poured into ice cold 50% aqueous H$_2$SO$_4$ (2 kg). The mixture was then diluted to a final volume of 5 L with water and allowed to stand overnight to settle. The dark supernatant was discarded, and the bead layer filtered using a coarse fritted funnel. The beads were washed with water until the pH of the filtrate was >4, as measured by pH indicator strips. The wet beads were then suspended in aqueous calcium acetate ("Ca(OAc)$_2$") (20% wt, 2 L) and shaken for 24 hours at 37° C., then the mixture was filtered, and the beads suspended in new aqueous Ca(OAc)$_2$ (20% wt, 2 L) and shaken again for 24 hours at 37° C. The beads were then washed successively with water (4×200 mL), and 100% MeOH (2×1500 mL), and dried under reduced pressure at 50° C. to give 29.8 g of Example 11 Ca-PSS resin as a fine light brown powder. Particle Size: d$_v$(0.1)=32 μm; d$_v$(0.5)=49 μm; d$_v$(0.9)=69 μm (visual microscopy). Ca-salt (8.6% wt/wt by titration); K+ exchange capacity (1.4 mE/g, per BP).

Example 12: Preparation of Calcium Polystyrene Sulfonate (Ca-PSS) with 2.2% Divinylbenzene (DVB)

Intermediate Polystyrene Beads at 2.2% DVB:

To a jacketed Morton style cylindrical vessel equipped with an overhead stirrer, thermocouple, and N$_2$ inlet was added polyvinyl alcohol (10 g), NaCl (10 g), NaNO$_2$ (0.2 g) and water (1 L). The mixture was stirred and heated to 70° C. for 1 h to form a slightly turbid solution. In a separate container, styrene (150 mL), divinylbenzene (3.5 mL, 80% Technical Grade), and benzoyl peroxide (6 g, 98%) were mixed to form a homogeneous solution of monomers and initiator. The monomer-initiator solution was added to the hot aqueous solution and within 1-2 minutes a uniform white suspension was achieved with 600 RPM stirring. The mixture was heated to 91-94° C. for 18 h, and then filtered while hot using a coarse fritted funnel. The solid polystyrene beads were suspended in water (1 L), and heated at 90° C. for 1 h. The mixture was then filtered while hot using a coarse fritted funnel, and the polystyrene beads were suspended in IPA (1 L), and heated at reflux for 1 h. The mixture was then filtered while still hot using a coarse fritted funnel, and dried in a vacuum oven to give 134 g of polystyrene beads as a white powder. Particle Size: d$_v$(0.1)=30 μm; d$_v$(0.5)=45 μm; d$_v$(0.9)=70 μm.

Example 12

To a 1 L round bottom flask, equipped with overhead stirrer, N$_2$ inlet, and a thermocouple was added silver sulfate (0.4 g) and sulfuric acid (98%, 300 mL). The mixture was warmed to 80° C. to dissolve, and then polystyrene beads (20 g) were added and the mixture stirred to form a suspension. The mixture was warmed to 90° C. for 1.5 h, then 100° C. for 1 h, then poured into ice cold 50% aqueous H$_2$SO$_4$ (2 kg) The mixture was then diluted to a final volume of 4 L with water and allowed to stand overnight to settle. The dark supernatant was discarded, and the bead layer filtered using a coarse fritted funnel. The beads were washed with water until the pH of the filtrate was >4, as measured by pH indicator strips. The wet beads were then suspended in aqueous Ca(OAc)$_2$ (20% wt, 1 L) and shaken for 24 h at 37° C., then the mixture was filtered, and the beads suspended in new aqueous Ca(OAc)$_2$ (20% wt, 1 L) and shaken again for 24 h at 37° C. The beads were then washed successively with water (2×1 L), 50% EtOH-water (2×150 mL), 75% EtOH-water (2×150 mL), and 100% EtOH 2×150 mL), and dried under reduced pressure at 50° C. to give 36.9 g of Example 12 Ca-PSS resin as a fine light brown powder. Particle Size: d(0.1)=53 pin; d(0.5)=76 pin; d(0.9)=108 pin; Ca-salt (8.3% wt/wt by titration); K+ exchange capacity (1.3 meq/g per BP); Residual Styrene (6 ppm).

Example 13: Preparation of Calcium Polystyrene Sulfonate (Ca-PSS) with 2.08% Divinylbenzene (DVB)

Intermediate Polystyrene Beads at 2.08% DVB:

To round bottom flask equipped with a heating mantle, an overhead stirrer, thermocouple, and N$_2$ inlet was added polyvinyl alcohol (1 g), NaCl (10 g), NaNO$_2$ (0.2 g) and water (1 L). The mixture was stirred and heated to 70° C. for 1 hour to dissolve, and then cooled to 20° C. In a separate container, styrene (147 g), divinylbenzene (3.9 g, 80% Technical Grade), and benzoyl peroxide (6.5 g, 98%) were mixed to form a homogeneous solution of monomers and initiator. The monomer-initiator solution was added to the aqueous solution and homogenized for 5 min at 6000 rpm (IKA Ultra-Turrax T50 basic, S50N-G45F). The mixture was stirred at 300 rpm and heated to 92° C. for 21 hours. The suspension was cooled and filtered using a coarse fritted funnel. The solid polystyrene beads were washed successively with water (2×350 mL), acetone (2×350 mL), and IPA (2×350 mL), and dried in a vacuum oven to give 135 g of polystyrene beads as a white powder. Particle size: d(0.1)=6.17 μm; d(0.5)=10.1 μm; d(0.9)=17.1 μm.

Example 13

To a 1 L round bottom flask, equipped with overhead stirrer, $N_2$ inlet, and a thermocouple was added silver sulfate (0.4 g) and sulfuric acid (98%, 300 mL). The mixture was warmed to 85° C. to dissolve, and then polystyrene beads (20 g) were added and the mixture stirred to form a suspension. The mixture was warmed to 100° C. for 3 hours, then poured into ice cold 50% aqueous $H_2SO_4$ (700 mL). The mixture was then diluted to a final volume of 3000 L with water and filtered using a coarse fritted funnel. The beads were washed with water until the pH of the filtrate was >4, as measured by pH indicator strips. The wet beads were then suspended in aqueous $Ca(OAc)_2$ (20% wt, 1.4 L) and shaken for 24 hours at 37° C., then the mixture was filtered, and the beads suspended in new aqueous $Ca(OAc)_2$ (20% wt, 1.4 L) and shaken again for 24 hours at 20° C. The beads were then washed successively with water (4×200 mL), 70% EtOH-water (2×150 mL), and 100% EtOH (2×150 mL), and dried under reduced pressure at 50° C. to give 28.6 g of Example 13 Ca-PSS resin as a light brown powder. The material was sieved using a 270 mesh (53 μm sieve to give a powder with Particle Size: $d_v(0.1)$=2 μm; $d_v(0.5)$=15 μm; $d_v(0.9)$=30 μm. Ca-salt (9.1 wt % by titration); K+ exchange capacity (1.46 mE/g, per BP); Residual Styrene: Not Detected (<0.1 ppm).

Example 14: Preparation of Calcium Polystyrene Sulfonate (Ca-PSS) with 2.5% Divinylbenzene (DVB)

Intermediate Polystyrene Beads at 2.5% DVB:
To round bottom flask equipped with a heating mantle, an overhead stirrer, thermocouple, and $N_2$ inlet was added polyvinyl alcohol (1 g), NaCl (10 g), $NaNO_2$ (0.2 g) and water (1 L). The mixture was stirred and heated to 70° C. for 1 hour to dissolve, and then cooled to 20° C. In a separate container, styrene, DVB and (147 g), divinylbenzene (4.7 g, 80% Technical Grade), and benzoyl peroxide (6.5 g, 98%) were mixed to form a homogeneous solution of monomers and initiator. The monomer-initiator solution was added to the aqueous solution and homogenized for 5 minutes at 6000 rpm (IKA Ultra-Turrax T50 basic, S50N-G45F). The mixture was stirred at 300 rpm and heated to 92° C. for 21 hours. The suspension was cooled and filtered using a coarse fritted funnel. The solid polystyrene beads were washed successively with water (2×350 mL), acetone (2×350 mL), and IPA (2×350 mL), and dried in a vacuum oven to give 133 g of polystyrene beads as a white powder. Particle size: d(0.1)=4 μm; d(0.5)=8 μm; d(0.9)=15 μm.

Example 14

To a 1 L round bottom flask, equipped with overhead stirrer, $N_2$ inlet, and a thermocouple was added silver sulfate (0.4 g) and sulfuric acid (98%, 300 mL). The mixture was warmed to 85° C. to dissolve, and then polystyrene beads (20 g) were added and the mixture stirred to form a suspension. The mixture was warmed to 100° C. for 3 hours, then poured into ice cold 50% aqueous $H_2SO_4$ (800 mL) The mixture was then diluted to a final volume of 3000 L with water and filtered using a coarse fritted funnel. The beads were washed with water until the pH of the filtrate was >4, as measured by pH indicator strips. The wet beads were then suspended in aqueous $Ca(OAc)_2$ (20% wt, 1.4 L) and shaken for 24 hours at 37° C., then the mixture was filtered, and the beads suspended in new aqueous $Ca(OAc)_2$ (20% wt, 1.4 L) and shaken again for 24 hours at 20° C. The beads were then washed successively with water (4×200 mL), 70% EtOH-water (2×150 mL), and 100% EtOH (2×150 mL), and dried under reduced pressure at 50° C. to give 30 g of Example 14 Ca-PSS resin as a light brown powder. The material was sieved using a 270 mesh (53 μm) sieve to give a powder with Particle Size: d(0.1)=3 μm; d(0.5)=15 μm; d(0.9)=27 μm; Ca-salt (9.05 wt % by titration); K+ exchange capacity (1.41 mE/g, per BP); Residual Styrene: Not Detected.

Example 15: Preparation of Calcium Polystyrene Sulfonate (Ca-PSS) with 4% Divinylbenzene (DVB)

Intermediate Polystyrene Beads at 4% DVB:
To round bottom flask equipped with a heating mantle, an overhead stirrer, thermocouple, and $N_2$ inlet was added polyvinyl alcohol (1 g), NaCl (10 g), $NaNO_2$ (0.2 g) and water (1 L). The mixture was stirred and heated to 70° C. for 1 hour to dissolve, and then cooled to 20° C. In a separate container, styrene (143.4 g), divinylbenzene (7.5 g, 80% Technical Grade), and benzoyl peroxide (6.5 g, 98%) were mixed to form a homogeneous solution of monomers and initiator. The monomer-initiator solution was added to the aqueous solution and homogenized for 5 minutes at 8000 rpm (IKA Ultra-Turrax T50 basic, S50N-G45F). The mixture was stirred at 300 rpm and heated to 92° C. for 21 hours. The suspension was cooled and filtered using a coarse fritted funnel. The solid polystyrene beads were washed successively with water (2×350 mL), acetone (2×350 mL), and IPA (2×350 mL), and dried in a vacuum oven to give 132 g of polystyrene beads as a white powder. Particle size: $d_v(0.1)$=2 μm; $d_v(0.5)$=7 μm; $d_v(0.9)$=11 μm.

Example 15

To a 1 L round bottom flask, equipped with overhead stirrer, $N_2$ inlet, and a thermocouple was added silver sulfate (0.4 g) and sulfuric acid (98%, 300 mL). The mixture was warmed to 80° C. to dissolve, and then polystyrene beads (20 g) were added and the mixture stirred to form a suspension. The mixture was warmed to 100° C. for 3 hours, then poured into ice cold 50% aqueous $H_2SO_4$ (3 kg) The mixture was then diluted to a final volume of 4 L with water and allowed to stand overnight to settle. The dark supernatant was discarded, and the bead layer filtered using a coarse fritted funnel. The beads were washed with water until the pH of the filtrate was >4, as measured by pH indicator strips. The wet beads were then suspended in aqueous $Ca(OAc)_2$ (20% wt, 1.4 L) and shaken for 24 hours at 37° C., then the mixture was filtered, and the beads suspended in new aqueous $Ca(OAc)_2$ (20% wt, 1.4 L) and shaken again for 24 hours at 37° C. The beads were then washed successively with water (4×200 mL), 70% EtOH-water (2×150 mL), and 100% EtOH (2×150 mL), and dried under reduced pressure at 50° C. to give 34 g of Example 15 Ca-PSS resin as a light brown powder. Particle Size: d(0.1)=3 μm; d(0.5)=12 μm;

d(0.9)=21 µm. Ca-salt (9.05 wt % by titration); K+ exchange capacity (1.32 mE/g, per BP); Residual Styrene (0.1 ppm).

Example 16: Preparation of Calcium Polystyrene Sulfonate (Ca-PSS) with 8% Divinylbenzene (DVB)

Intermediate Polystyrene Beads at 8% DVB:

To round bottom flask equipped with a heating mantle, an overhead stirrer, thermocouple, and $N_2$ inlet was added polyvinyl alcohol (1 g), NaCl (10 g), $NaNO_2$ (0.2 g) and water (1 L). The mixture was stirred and heated to 70° C. for 1 hour to dissolve, and then cooled to 20° C. In a separate container, styrene (98 g), divinylbenzene (10.7 g, 80% Technical Grade), and benzoyl peroxide (4.5 g, 98%) were mixed to form a homogeneous solution of monomers and initiator. The monomer-initiator solution was added to the aqueous solution and homogenized for 5 min at 8000 rpm (IKA Ultra-Turrax T50 basic, S50N-G45F). The mixture was stirred at 300 rpm and heated to 92° C. for 4 hours, then 85° C. overnight. The suspension was cooled and filtered using a coarse fritted funnel. The solid polystyrene beads were washed successively with water (2×350 mL), acetone (2×350 mL), and IPA (2×350 mL), and dried in a vacuum oven to give 91 g of polystyrene beads as a white powder. Particle size: $d_v(0.1)$=3 µm; $d_v(0.5)$=7 µm; $d_v(0.9)$=11 µm.

Example 16

To a 1 L round bottom flask, equipped with overhead stirrer, $N_2$ inlet, and a thermocouple was added silver sulfate (0.4 g) and sulfuric acid (98%, 300 mL). The mixture was warmed to 80° C. to dissolve, and then polystyrene beads (20 g) were added and the mixture stirred to form a suspension. The mixture was warmed to 100° C. for 3 hours, then poured into ice cold 50% aqueous $H_2SO_4$ (3 kg) The mixture was then diluted to a final volume of 4 L with water and allowed to stand overnight to settle. The dark supernatant was discarded, and the bead layer filtered using a coarse fritted funnel. The beads were washed with water until the pH of the filtrate was >4, as measured by pH indicator strips. The wet beads were then suspended in aqueous $Ca(OAc)_2$ (20% wt, 1.4 L) and shaken for 24 hours at 37° C., then the mixture was filtered, and the beads suspended in new aqueous $Ca(OAc)_2$ (20% wt, 1.4 L) and shaken again for 24 hours at 37° C. The beads were then washed successively with water (4×200 mL), 70% EtOH-water (2×150 mL), and 100% EtOH (2×150 mL), and dried under reduced pressure at 50° C. to give 32.4 g of Example 16 Ca-PSS resin as a light brown powder. Particle Size: $d_v(0.1)$=2 µm; $d_v(0.5)$=11 µm; $d_v(0.9)$=17 µm. Ca-salt (8.58 wt % by titration); K+ exchange capacity (1.43 mE/g, per BP).

Example 17: Preparation of Calcium Polystyrene Sulfonate from Seeded Polymerization Intermediate Polystyrene Seed Particles (2 µm) by Dispersion Polymerization:

To a jacketed Morton style cylindrical vessel equipped with an overhead stirrer, thermocouple, and $N_2$ inlet was added styrene (136 mL, used as is), polyvinylpyrrolidone ("PVP") (12 g, MW 40,000), and anhydrous EtOH (784 mL). The mixture was stirred at 200 rpm and heated to 70° C. to achieve full solution. After 30 min, AIBN (1.2 g) dissolved in anhydrous EtOH (224 mL) was added to the solution. The mixture was stirred at 70° C. for 24 hours, then cooled to 20° C. The PS seed particles were isolated by centrifugation at 5300 G for 10 minutes, the supernatant was discarded and the solid suspended in EtOH (2×150 mL) by shaking for 15 minutes, and the solid isolated by centrifugation at 5300 G for 10 minutes. The solid was dried under reduced pressure at 50° C. to give 73.9 g of seed particles as a white powder. $d_v(0.1)$=0.6 µm; $d_v(0.5)$=2 µm; $d_v(0.9)$=3 µm.

Intermediate PS Beads from Seeded Polymerization:

To a jacketed Morton style cylindrical vessel equipped with an overhead stirrer, thermocouple, and $N_2$ inlet was added PS seed particles (5 g) and sodium dodecyl sulfate aqueous solution (0.25% (w/w), 500 mL) and the mixture was stirred overnight (35° C., 120 rpm). Then, a monomer-initiator solution containing BPO (1.5 g), styrene (50 mL), divinylbenzene (3.62 g, 6.4% based on styrene) (divinylbenzene was purified by passing 10 g of technical grade DVB through 10 g of basic alumina) was added to the mixture containing PS seeds. The mixture was homogenized (VWR homogenizer, model VDI 25) at 17500 rpm for 30 minutes. The mixture was stirred overnight (35° C. at 120 rpm) to swell the seed particles. The swelling was monitored by optical microscopy. After 20 hours, the mixture was homogenized again (VWR homogenizer, model VDI 25). Separately, PVP (2.5 g, MW 350,000) was dissolved in deionized water (250 mL), and added to the swollen seed mixture. The mixture was stirred at 400 rpm and heated to 75° C. for 24 hours, then cooled to 20° C. The PS beads were isolated by centrifugation at 5300 G for 10 min. The solid was suspended in water (200 mL) for 10 minutes by shaking and isolated by centrifugation at 5300 G for 10 minutes. the solid was suspended in EtOH (2×150 mL) for 15 minutes by shaking, and isolated by centrifugation at 5300 G for 10 minutes, and the supernatant discarded. The solid was dried under reduced pressure at 50° C. to give 32.1 g of bead particles as a white powder.

Example 17

To a round bottom flask, equipped with overhead stirrer, $N_2$ inlet, and a thermocouple was added silver sulfate (0.4 g) and sulfuric acid (98%, 300 mL). The mixture was warmed to 80° C. to dissolve, and then intermediate PS beads from seeded polymerization (20 g) were added and the mixture stirred to form a suspension. The mixture was warmed to 100° C. for 3 hours, then poured into ice cold 50% aqueous $H_2SO_4$ (2 kg). The mixture was then diluted to a final volume of 5 L with water and allowed to stand overnight to settle. The dark supernatant was discarded, and the bead layer was isolated by centrifugation at 3400 G for 10 minutes; the supernatant was discarded and the beads were washed with water until the pH of the filtrate was >4, as measured by pH indicator strips. The wet beads were then suspended in aqueous $Ca(OAc)_2$ (20% wt, 2 L) and shaken for 24 hours at 37° C., then the beads were isolated by centrifugation at 3400 G for 10 minutes. The supernatant was discarded, and the beads suspended in new aqueous $Ca(OAc)_2$ (20% wt, 2 L) and shaken again for 24 hours at 37° C. The beads were isolated by centrifugation at 3400 G for 10 minutes. The beads were washed and centrifuged successively with MeOH (2×150 mL), and dried under reduced pressure at 50° C. to give 36.9 g of Example 17 Ca-PSS resin. A portion of the beads (19 g) was further washed by successive suspension and centrifugation at 3400×g with water (700 mL), 70% EtOH (2×250 mL), and 100% EtOH (2×250 mL). The isolated solid was then dried under reduced pressure at 50° C. to give 18.8 g of Example 17 as a light brown powder. Particle Size: $d_v(0.1)$=1 µm;

$d_v(0.5)=6$ μm; $d_v(0.9)=10$ μm. Ca-salt (7.55 wt % by titration); K+ exchange capacity 1.0 mEq/g (per BP); Residual Styrene 0.4 ppm.

Example 18: Preparation of Calcium Polystyrene Sulfonate (Ca-PSS) with 2.0% Divinylbenzene (DVB)

Intermediate Polystyrene Beads at 2.0% DVB:

To a jacketed Morton style cylindrical vessel equipped with an overhead stirrer, thermocouple, and $N_2$ inlet was added polyvinyl alcohol (10 g), NaCl (10 g), $NaNO_2$ (0.2 g) and water (1 L). The mixture was stirred and heated to 70° C. for 1 hour to form a slightly turbid solution. In a separate container, styrene (150 mL), divinylbenzene (3.8 mL, 80% Technical Grade), and benzoyl peroxide (6 g, 98%) were mixed to form a homogeneous solution of monomers and initiator. The monomer-initiator solution was added to the hot aqueous solution and within 1-2 minutes a uniform white suspension was achieved with 600 RPM stirring. The mixture was heated to 91-94° C. for 18 hours, and then filtered while hot using a coarse fritted funnel. The solid polystyrene beads were suspended in water (1 L), and heated at 90° C. for 1 hour. The mixture was then filtered while hot using a coarse fritted funnel, and the polystyrene beads were suspended in IPA (1 L), and heated at reflux for 1 h. The mixture was then filtered while still hot using a coarse fritted funnel, and dried in a vacuum oven to give 136 g of polystyrene beads as a white powder. Particle Size: $d_v(0.1)=30$ μm; $d_v(0.5)=40$ μm; $d_v(0.9)=60$ μm.

Example 18

To a 1 L round bottom flask, equipped with overhead stirrer, $N_2$ inlet, and a thermocouple was added silver sulfate (0.4 g) and sulfuric acid (98%, 300 mL). The mixture was warmed to 80° C. to dissolve, and then polystyrene beads (20 g) were added and the mixture stirred to form a suspension. The mixture was warmed to 100° C. for 3 hours, then poured into ice cold 50% aqueous $H_2SO_4$ (2 kg) The mixture was then diluted to a final volume of 3.5 L with water and allowed to stand overnight to settle. The dark supernatant was discarded, and the bead layer filtered using a coarse fritted funnel. The beads were washed with water until the pH of the filtrate was >4, as measured by pH indicator strips. The wet beads were then suspended in aqueous $Ca(OAc)_2$ (20% wt, 1 L) and shaken for 24 hours at 37° C., then the mixture was filtered, and the beads suspended in new aqueous $Ca(OAc)_2$ (20% wt, 1 L) and shaken again for 24 hours at 37° C. The beads were then washed successively with water (4×200 mL), 70% EtOH-water (2×150 mL), and 100% EtOH (2×150 mL), and dried under reduced pressure at 50° C. to give 35.7 g of Example 18 Ca-PSS resin as a fine light brown powder. Particle Size: $d_v(0.1)=57$ μm; $d_v(0.5)=80$ μm; $d_v(0.9)=110$ μm.

Example 19: Preparation of Calcium Polystyrene Sulfonate (Ca-PSS) with 1.8% Divinylbenzene (DVB)

Example 19 was prepared from 40 g crosslinked (1.8%) polystyrene sulfonate beads using the procedures described in Example 10 to give 69.4 g of Example 19 as a light brown powder: particle size 30-130 μm (visual microscopy). Residual Styrene: Not Detected.

Example 20: Preparation of Calcium Polystyrene Sulfonate from Seeded Polymerization Intermediate Polystyrene Seed Particles (2 μm) by Dispersion Polymerization:

Seeds were prepared following the procedures described in Example 17.

Intermediate PS Beads from Seeded Polymerization:

To a jacketed Morton style cylindrical vessel equipped with an overhead stirrer, thermocouple, and $N_2$ inlet was added PS seed particles (5 g), sodium dodecyl sulfate aqueous solution (0.25% (w/w), 500 mL). The mixture was stirred overnight (35° C., 120 rpm). Then, a monomer-initiator solution containing BPO (1.5 g), styrene (50 mL), divinylbenzene (0.91 g, 1.8% based on styrene) (divinylbenzene was purified by passing 10 g of technical grade DVB through 10 g of basic alumina) was added to the mixture containing PS seeds. The mixture was homogenized (IKA homogenizer, model T50 Digital) at 2000 rpm for 30 minutes. The mixture was stirred overnight (35° C. at 120 rpm) to swell the seed particles. The swelling was monitored by optical microscopy. After 20 hours, the mixture was homogenized again at 2000 rpm for 30 minutes (IKA homogenizer, model T50 Digital). Separately, PVP (2.5 g, MW 350,000) was dissolved in deionized water (250 mL), and added to the swollen seed mixture. The mixture was stirred at 400 rpm and heated to 75° C. for 24 hours, then cooled to 20° C. The PS beads were isolated by centrifugation at 5300 G for 10 minutes. The solid was suspended in MeOH (200 mL) for 15 min by shaking, and isolated by centrifugation at 5300 G for 10 minutes, and the supernatant discarded. The solid was dried under reduced pressure at 50° C. to give 27.74 g of bead particles as a white powder. Approximate particle size range 6-8 μm by visual microscopy.

Example 20

To a round bottom flask, equipped with overhead stirrer, $N_2$ inlet, and a thermocouple was added silver sulfate (0.4 g) and sulfuric acid (98%, 300 mL). The mixture was warmed to 80° C. to dissolve, and then intermediate PS beads from seeded polymerization (20 g) were added and the mixture stirred to form a suspension. The mixture was warmed to 100° C. for 3 hours, then poured into ice cold 50% aqueous $H_2SO_4$ (2 kg). The mixture was then diluted to a final volume of 5 L with water and allowed to stand overnight to settle. The dark supernatant was discarded, and the bead layer was isolated by centrifugation at 3400 G for 10 minutes; the supernatant was discarded and the beads were washed with water until the pH of the filtrate was >4, as measured by pH indicator strips. The wet beads were then suspended in aqueous $Ca(OAc)_2$ (20% wt, 2 L) and shaken for 24 hours at 37° C., then the beads were isolated by centrifugation at 3400 G for 10 minutes. The supernatant was discarded, and the beads suspended in new aqueous $Ca(OAc)_2$ (20% wt, 2 L) and shaken again for 24 hours at 37° C. The beads were isolated by centrifugation at 3400 G for 10 minutes. The beads were washed and centrifuged successively with water (200 mL) and 70% MeOH (2×150 mL), and dried under reduced pressure at 50° C. to give 33.2 g of Example 20 Ca-PSS resin as a dark brown chunks. The beads were suspended and centrifuged successively with water (700 mL), 70% EtOH (500 mL), and 100% IPA (200 mL) and dried under reduced pressure at 50° C. to give 27.8 g of Example 20 Ca-PSS resin as a dark brown chunks. A portion of the beads were suspended and centrifuged successively with water (2×2 L), followed by 70% EtOH (500 mL) and 100% EtOH (500 mL). The material was dried under reduced pressure (50° C.) to give 16.3 g of Example 20 Ca-PSS resin as a light brown powder: particle size $d_v(0.1)=4$ µm; $d_v(0.5)=7$ µm; $d_v(0.9)=12$ µm; Ca-salt (7.53 wt % by titration); $K^+$ exchange capacity 1.4 mEq/g (per BP); Residual Styrene 0.09 ppm.

Example 21: Preparation of Calcium Polystyrene Sulfonate from Seeded Polymerization Intermediate Polystyrene Seed Particles (4 µm) by Dispersion Polymerization:

To a jacketed Morton style cylindrical vessel equipped with an overhead stirrer, thermocouple, and $N_2$ inlet was added styrene (68 mL, used as is), Polyvinylpyrrolidone, PVP, (6 g, MW 40,000), and IPA (392 mL). The mixture was stirred at 200 rpm and heated to 70° C. to achieve full solution. After 30 minutes, Azobisisobutyronitrile ("AIBN") (0.6 g) dissolved in IPA (112 mL) was added to the solution. The mixture was stirred at 70° C. for 24 hours, then cooled to 20° C. The PS seed particles were isolated by centrifugation at 5300 G for 10 minutes, the supernatant was discarded and the solid suspended in EtOH (150 mL) by shaking for 15 minutes, and the solid isolated by centrifugation at 5300 G for 10 minutes. The solid was dried under reduced pressure at 50° C. to give 55.28 g of seed particles as a white powder. Particle size $d_v(0.1)=2$ µm; $d_v(0.5)=4$ µm; $d_v(0.9)=6$ µm.

Intermediate PS Beads from Seeded Polymerization:

To a jacketed Morton style cylindrical vessel equipped with an overhead stirrer, thermocouple, and $N_2$ inlet was added PS seed particles (3 g), sodium dodecyl sulfate aqueous solution (0.25% (w/w), 300 mL). The mixture was stirred overnight (35° C., 120 rpm). Then, a monomer-initiator solution containing BPO (1.5 g), styrene (30 mL), divinylbenzene (0.54 g, 1.8% based on styrene) (divinylbenzene was purified by passing 10 g of technical grade DVB through 10 g of basic alumina) was added to the mixture containing PS seeds. The mixture was homogenized (IKA homogenizer, model T50 Digital) at 2000 rpm for 30 minutes. The mixture was stirred overnight (35° C. at 120 rpm) to swell the seed particles. The swelling was monitored by optical microscopy. Separately, PVP (1.5 g, MW 350,000) was dissolved in deionized water (150 mL), and added to the swollen seed mixture. The mixture was stirred at 400 rpm and heated to 75° C. for 24 hours, then cooled to 20° C. The PS beads were isolated by centrifugation at 5300 G for 10 minutes. The solid was suspended in water (200 mL) for 10 minutes by shaking and isolated by centrifugation at 5300 G for 10 minutes. Then the solid was suspended in EtOH (2×150 mL) for 15 minutes by shaking, and isolated by centrifugation at 5300 G for 10 minutes, and the supernatant discarded. The solid was dried under reduced pressure at 50° C. to give 16 g of bead particles as a white powder.

Example 21

To a round bottom flask, equipped with overhead stirrer, $N_2$ inlet, and a thermocouple was added silver sulfate (0.32 g) and sulfuric acid (98%, 240 mL). The mixture was warmed to 80° C. to dissolve, and then intermediate PS beads from seeded polymerization (16 g) were added and the mixture stirred to form a suspension. The mixture was warmed to 100° C. for 3 hours, then poured into ice cold 50% aqueous $H_2SO_4$ (2 kg). The mixture was then diluted to a final volume of 5 L with water and allowed to stand overnight to settle. The dark supernatant was discarded, and the bead layer was isolated by centrifugation at 3400 G for 10 minutes; the supernatant was discarded and the beads were washed with water until the pH of the filtrate was >4, as measured by pH indicator strips. The wet beads were then suspended in aqueous $Ca(OAc)_2$ (20% wt, 1 L) and shaken for 24 hours at 37° C., then the beads were isolated by centrifugation at 3400 G for 10 minutes. The supernatant was discarded, and the beads suspended in new aqueous $Ca(OAc)_2$ (20% wt, 1 L) and shaken again for 24 hours at 37° C. The beads were isolated by centrifugation at 3400×g for 10 min. The beads were suspended and centrifuged successively with water (200 mL), 70% EtOH (350 mL), 100% EtOH (350 mL), and dried under reduced pressure.

A portion of material (19.5 g) was suspended in water (2000 mL) by shaking at 150 rpm overnight, and isolated by centrifugation at 3400 G for 10 min. The beads were washed again with water (2000 mL) and centrifuged successively with 70% EtOH (2×250 mL), and 100% EtOH (2×250 mL), dried under reduced pressure at 50° C. to give Example 21 as a light brown powder. Ca-salt (8.56 wt % by titration); Residual Styrene 0.21 ppm.

Example 22: Preparation of Calcium Polystyrene Sulfonate (Ca-PSS), ≤43 µm Particle Size, 8% Divinylbenzene (DVB)

Approximately 15 g of Ionex Ca-PSS (Phaex Polymers, India), British Pharmacopeia (BP) grade, was deposited onto a 320 mesh sieve (43 µm pore size) and mechanically agitated on an orbital shaker for approximately 30 minutes, and the sieved fraction (solids ≤43 µm) was collected (approximately 3 g). Particle size $d_v(0.1)=9$ µm; $d_v(0.5)=30$ µm; $d_v(0.9)=60$ µm; Ca-salt (8.69 wt % by titration); K+ exchange capacity 1.35 mEq/g (per BP); Residual Styrene 0.2 ppm.

Example 23: Preparation of Sodium Polystyrene Sulfonate (Ca-PSS) with 8% Divinylbenzene (DVB)

Approximately 20 g of an aqueous suspension of Na SPS (8% DVB) in a water/sorbitol suspension (Carolina Medical Products) was deposited onto a sintered glass funnel and washed several times with DI water to remove sorbitol, and then dried to afford a tan-colored solid.

Example 24: Preparation of Insoluble Cross-linked (Calcium 2-Fluoroacrylate)-Divinylbenzene-1,7-Octadiene Copolymer In an appropriately sized reactor with appropriate stirring and other equipment, a mixture of organic phase of monomers is prepared by mixing methyl 2-fluoroacrylate, 1,7-octadiene, and divinylbenzene in a mole ratio of about 120:1:1, respectively. Approximately one part of lauroyl peroxide is added as an initiator of the polymerization reaction. A stabilizing aqueous phase is prepared from water, polyvinyl alcohol, phosphates, sodium chloride, and sodium nitrite. The aqueous and monomer phases are mixed together under nitrogen at atmospheric pressure, while maintaining the temperature below 30° C. The reaction mixture is gradually heated while stirring continuously. Once the polymerization reaction starts, the temperature of the reaction mixture is allowed to rise to a maximum of 95° C.

After completion of the polymerization reaction, the reaction mixture is cooled and the aqueous phase is removed. Water is added, the mixture is stirred, and the solid material is isolated by filtration. The solid is then washed with water to yield a crosslinked (methyl 2-fluoroacrylate)-divinylbenzene-1,7-octadiene copolymer. The (methyl 2-fluoroacrylate)-divinylbenzene-1,7-octadiene copolymer is hydrolyzed with an excess of aqueous sodium hydroxide solution at 90° C. for 24 hours to yield (sodium 2-fluoroacrylate)-divinylbenzene-1,7-octadiene copolymer. After hydrolysis, the solid is filtered and washed with water. The (sodium 2-fluoroacrylate)-divinylbenzene-1,7-octadiene copolymer is exposed at room temperature to an excess of aqueous calcium chloride solution to yield insoluble cross-linked (calcium 2-fluoroacrylate)-divinylbenzene-1,7-octadiene copolymer. After the calcium ion exchange, the product is washed with water and dried.

Example 25: Preparation of Calcium Polystyrene Sulfonate (Ca-PSS) from 30 Micron Monodisperse Polystyrene Beads Example 25 was prepared from 20 g polystyrene beads (Amberchrom™ XT30; obtained from Octochemstore.com), using the procedures described in Example 7 to give Example 25 (29.6 g) as a brown powder. Particle size: dv(0.1)=25 μm; dv(0.5)=34 μm; dv(0.9)=48 μm.

Example 26: Procedure for Tactile Testing

Tactile Testing Experiment #1.

Tactile testing samples were prepared by suspending 2.1 g of dry polystyrene sulfonate resin powder (calcium and or sodium forms) in DI water (15 mL) at 20° C. in amber bottles. The mixtures were shaken vigorously for 1 mm by hand, and then allowed to stand overnight. Immediately prior to dispensing samples to test subjects, the vials were agitated using a bench top vortex mixer for approximately 20 seconds. Test subjects washed their hands with soap and water before beginning. A tactile test sample of 150 μL was dispensed onto the thenar eminence of one hand, and the test subjects were instructed to rub test sample between the thenar eminence of both hands. Test subjects rated their experience on two sensations: grittiness (Table 1), and tackiness (Table 2). Sensations were rated from 1-5 with 1=no sensation and 5=strong sensation. After each sample, test subjects washed their hands with soap and water.

TABLE 1

GRITTINESS DATA FROM TACTILE TESTING EXPERIMENT #1.

| | Example # | | | | | | | |
|---|---|---|---|---|---|---|---|---|
| | 22 | N/A[1] | 12 | 11 | 10 | 9 | 4 | 23 |
| Resin ID | 1 | 2 | 3 | 4 | 5 | 6 | 7 | 8 |
| Crosslinking | ~8% | ~8% | 2.2% | 2.0% | 1.8% | 1.6% | 2.0% | ~8% |
| Particle size (Dv50) | 45 μm | N/A | 76 μm | 44 μm | 77 μm | 75 μm | 120 μm | 69 μm |
| morphology | Shard | Shard | Sphere | Sphere | Sphere | Sphere | Sphere | Shard |
| Subject ID | | | | Grittiness | | | | |
| Subject 1 | 4 | 5 | 4 | 2 | 1 | 3 | 5 | 5 |
| Subject 2 | 3 | 2 | 2 | 1 | 1 | 2 | 3 | 3 |
| Subject 3 | 5 | 4 | 2 | 1 | 2 | 2 | 4 | 5 |
| Subject 4 | 3 | 3 | 3 | 1 | 2 | 2 | 4 | 4 |
| Subject 5 | 4 | 4 | 1 | 1 | 2 | 1 | 2 | 4 |
| Subject 6 | 4 | 3 | 3 | 1 | 2 | 2 | 4 | 4 |
| Subject 7 | 3 | 3 | 1 | 1 | 1 | 1 | 3 | 2 |
| Subject 8 | 2 | 3 | 2 | 1 | 1 | 2 | 2 | 3 |
| Subject 9 | 4 | 4 | 4 | 1 | 1 | 1 | 3 | 4 |
| Subject 10 | 3 | 3 | 2 | 1 | 1 | 2 | 4 | 5 |
| Subject 11 | 5 | 2 | 1 | 1 | 2 | 2 | 3 | 3 |
| Subject 12 | 4 | 2 | 1 | 1 | 1 | 2 | 3 | 3 |
| Subject 13 | 5 | 4 | 3 | 2 | 1 | 1 | 1 | 5 |
| Subject 14 | 5 | 4 | 2 | 2 | 1 | 1 | 3 | 4 |
| Subject 15 | 5 | 4 | 2 | 2 | 1 | 1 | 4 | 5 |
| Subject 16 | 3 | 3 | 2 | 1 | 2 | 1 | 3 | 4 |
| Subject 17 | 5 | 2 | 2 | 1 | 1 | 2 | 3 | 5 |
| Subject 18 | 5 | 4 | 3 | 2 | 1 | 2 | 4 | 5 |
| Average | 4.0 | 3.3 | 2.2 | 1.3 | 1.3 | 1.7 | 3.2 | 4.1 |
| Std Dev | 1.0 | 0.9 | 0.9 | 0.5 | 0.5 | 0.6 | 0.9 | 0.9 |
| total | 72 | 59 | 40 | 23 | 24 | 30 | 58 | 73 |

[1]RESONIUM CALCIUM ®, Ca-PSS, Sanofi-Aventis

TABLE 2

TACKINESS DATA FROM TACTILE TESTING EXPERIMENT #1.

| | \multicolumn{8}{c}{Example #} | | | | | | | |
|---|---|---|---|---|---|---|---|---|
| | 22 | N/A[1] | 12 | 11 | 10 | 9 | 4 | 23 |
| Resin ID | 1 | 2 | 3 | 4 | 5 | 6 | 7 | 8 |
| Crosslinking | ~8% | ~8% | 2.2% | 2.0% | 1.8% | 1.6% | 2.0% | ~8% |
| Particle size (Dv50) | 45 μm | N/A | 76 μm | 44 μm | 77 μm | 75 μm | 120 μm | 69 μm |
| Morphology | Shard | Shard | Sphere | Sphere | Sphere | Sphere | Sphere | shard |
| Subject ID | \multicolumn{8}{c}{Tackiness} | | | | | | | |
| Subject 1 | 1 | 1 | 1 | 1 | 1 | 1 | 1 | 1 |
| Subject 2 | 1 | 1 | 1 | 1 | 1 | 2 | 3 | 1 |
| Subject 3 | 1 | 2 | 1 | 1 | 2 | 2 | 1 | 1 |
| Subject 4 | 1 | 1 | 1 | 2 | 1 | 1 | 1 | 1 |
| Subject 5 | 1 | 1 | 1 | 1 | 1 | 2 | 1 | 1 |
| Subject 6 | 1 | 1 | 1 | 1 | 1 | 2 | 1 | 1 |
| Subject 7 | 2 | 1 | 2 | 2 | 3 | 3 | 2 | 2 |
| Subject 8 | 1 | 1 | 2 | 3 | 4 | 3 | 2 | 1 |
| Subject 9 | 1 | 1 | 1 | 2 | 3 | 4 | 3 | 1 |
| Subject 10 | 1 | 2 | 1 | 3 | 2 | 3 | 1 | 2 |
| Subject 11 | 1 | 1 | 1 | 1 | 1 | 1 | 1 | 1 |
| Subject 12 | 1 | 1 | 2 | 2 | 1 | 3 | 1 | 2 |
| Subject 13 | 1 | 1 | 1 | 2 | 3 | 3 | 3 | 1 |
| Subject 14 | 3 | 2 | 2 | 3 | 2 | 1 | 2 | 3 |
| Subject 15 | 1 | 1 | 1 | 1 | 5 | 5 | 1 | 1 |
| Subject 16 | 1 | 1 | 1 | 1 | 1 | 2 | 1 | 1 |
| Subject 17 | 3 | 2 | 2 | 1 | 2 | 3 | 3 | 3 |
| Subject 18 | 1 | 1 | 1 | 1 | 3 | 3 | 2 | 2 |
| Average | 1.3 | 1.2 | 1.3 | 1.6 | 2.1 | 2.4 | 1.7 | 1.4 |
| Std Dev | 0.7 | 0.4 | 0.4 | 0.8 | 1.2 | 1.1 | 0.8 | 0.7 |
| total | 23 | 22 | 23 | 29 | 37 | 44 | 30 | 26 |

[1]RESONIUM CALCIUM ®, Ca-PSS, Sanofi-Aventis

Tactile Testing Experiment #2.

Tactile testing samples were prepared by suspending 3 g of dry polystyrene sulfonate resin powder (Calcium and or Sodium forms) in DI water (15 mL) at 20° C. in amber bottles. The mixtures were shaken vigorously for 1 minute by hand, and then allowed to stand overnight. Immediately prior to dispensing samples to test subjects, the vials were agitated using a bench top vortex mixer for approximately 20 seconds. Test subjects washed their hands with soap and water before beginning. A tactile test sample of 150 μL was dispensed onto the thenar eminence of one hand, and the test subjects were instructed to rub the test sample between the thenar eminence of both hands. Test subjects rated their experience on two sensations: grittiness (Table 3) and tackiness (Table 4). Sensations were rated from 1-5 with 1=low sensation and 5=high sensation. After each sample, test subjects washed their hands with soap and water.

TABLE 3

GRITTINESS DATA FROM TACTILE TESTING EXPERIMENT #2

| | \multicolumn{11}{c}{Example #} | | | | | | | | | | | |
|---|---|---|---|---|---|---|---|---|---|---|---|---|
| | N/A[1] | 4 | 13 | 14 | 15 | 16 | 17 | 18 | 19 | 22 | 25 | 11 |
| Crosslinking | N/A | 2.0% | 2.08% | 2.5% | 4.0% | 8.0% | 6.5% | 2.0% | 1.8% | N/A | N/A | 2.0% |
| Particle size (Dv50) | N/A | 120 μm | 13 μm | 14 μm | 12 μm | 11 μm | 7 μm | 81 μm | N/A | 31 μm | N/A | 44 μm |
| Morphology | Shards | Sphere | Sphere | Sphere | Sphere | Sphere | Sphere | Sphere | Sphere | Shards | Sphere | Sphere |
| Resin ID | 1 | 2 | 3 | 4 | 5 | 6 | 7 | 8 | 9 | 10 | 11 | 12 |
| Subject ID | \multicolumn{11}{c}{Grittiness} | | | | | | | | | | | |
| Subject 1 | 5 | 5 | 2 | 3 | 3 | 2 | 1 | 4 | 3 | 4 | 4 | 4 |
| Subject 2 | 2 | 3 | 1 | 1 | 1 | 2 | 1 | 2 | 3 | 1 | 2 | 1 |
| Subject 3 | 2 | 1 | 1 | 1 | 2 | 1 | 2 | 1 | 1 | 3 | 2 | 1 |
| Subject 4 | 4 | 3 | 2 | 3 | 2 | 1 | 2 | 1 | 3 | 1 | 2 | 1 |
| Subject 5 | 4 | 3 | 1 | 1 | 2 | 2 | 2 | 1 | 3 | 1 | 2 | 2 |
| Subject 6 | 5 | 3 | 1 | 2 | 2 | 2 | 1 | 1 | 1 | 3 | 1 | 3 |
| Subject 7 | 4 | 5 | 1 | 1 | 2 | 3 | 1 | 1 | 2 | 3 | 2 | 1 |
| Subject 8 | 4 | 5 | 1 | 2 | 5 | 3 | 3 | 4 | 2 | 2 | 2 | 2 |
| Subject 9 | 4 | 2 | 2 | 2 | 1 | 1 | 1 | 1 | 1 | 3 | 3 | 2 |
| Subject 10 | 4 | 3 | 1 | 3 | 2 | 2 | 3 | 1 | 4 | 1 | 1 | 3 |
| Subject 11 | 3 | 2 | 1 | 2 | 1 | 1 | 1 | 1 | 1 | 1 | 1 | 2 |
| Subject 12 | 4 | 3 | 1 | 1 | 2 | 2 | 3 | 1 | 3 | 3 | 3 | 2 |

TABLE 3-continued

GRITTINESS DATA FROM TACTILE TESTING EXPERIMENT #2

| | Example # | | | | | | | | | | |
|---|---|---|---|---|---|---|---|---|---|---|---|
| | N/A[1] | 4 | 13 | 14 | 15 | 16 | 17 | 18 | 19 | 22 | 25 | 11 |
| Subject 13 | 5 | 4 | 2 | 2 | 1 | 2 | 3 | 3 | 3 | 4 | 4 | 2 |
| Average | 3.8 | 3.2 | 1.3 | 1.8 | 2.0 | 1.8 | 1.8 | 1.7 | 2.3 | 2.3 | 2.2 | 2.0 |
| Std Dev | 1.0 | 1.2 | 0.5 | 0.8 | 1.1 | 0.7 | 0.9 | 1.2 | 1.0 | 1.2 | 1.0 | 0.9 |
| total | 50 | 42 | 17 | 24 | 26 | 24 | 24 | 22 | 30 | 30 | 29 | 26 |

[1]RESONIUM CALCIUM ®, Ca-PSS, Sanofi-Aventis

TABLE 4

TACKINESS DATA FROM TACTILE TESTING EXPERIMENT #2

| | Example # | | | | | | | | | | |
|---|---|---|---|---|---|---|---|---|---|---|---|
| | N/A[1] | 4 | 13 | 14 | 15 | 16 | 17 | 18 | 19 | 22 | 25 | 11 |
| Crosslinking | N/A | 2.0% | 2.08% | 2.5% | 4.0% | 8.0% | 6.5% | 2.0% | 1.8% | N/A | N/A | 2.0% |
| Particle size (Dv50) | N/A | 120 μm | 13 μm | 14 μm | 12 μm | 11 μm | 7 μm | 81 μm | N/A | 31 μm | N/A | 44 μm |
| Morphology | Shards | Sphere | Sphere | Sphere | Sphere | Sphere | Sphere | Sphere | Sphere | Shards | Sphere | Sphere |
| Resin ID | 1 | 2 | 3 | 4 | 5 | 6 | 7 | 8 | 9 | 10 | 11 | 12 |
| Subject ID | Grittiness | | | | | | | | | | |
| Subject 1 | 1 | 1 | 1 | 1 | 1 | 1 | 1 | 1 | 1 | 1 | 1 | 1 |
| Subject 2 | 1 | 1 | 2 | 1 | 1 | 1 | 2 | 2 | 1 | 1 | 1 | 2 |
| Subject 3 | 1 | 3 | 3 | 3 | 2 | 1 | 1 | 5 | 2 | 1 | 1 | 2 |
| Subject 4 | 1 | 4 | 2 | 1 | 1 | 1 | 1 | 2 | 4 | 1 | 2 | 1 |
| Subject 5 | 1 | 1 | 2 | 2 | 2 | 1 | 2 | 2 | 2 | 1 | 2 | 2 |
| Subject 6 | 1 | 1 | 4 | 3 | 3 | 2 | 4 | 4 | 5 | 1 | 4 | 3 |
| Subject 7 | 1 | 1 | 2 | 1 | 1 | 1 | 1 | 2 | 2 | 1 | 1 | 1 |
| Subject 8 | 1 | 1 | 3 | 3 | 1 | 2 | 2 | 2 | 2 | 1 | 3 | 3 |
| Subject 9 | 1 | 2 | 3 | 2 | 2 | 1 | 2 | 3 | 4 | 1 | 2 | 3 |
| Subject 10 | 1 | 2 | 3 | 4 | 1 | 1 | 2 | 3 | 4 | 1 | 1 | 2 |
| Subject 11 | 1 | 1 | 1 | 1 | 1 | 1 | 1 | 2 | 3 | 1 | 1 | 1 |
| Subject 12 | 2 | 1 | 2 | 3 | 3 | 2 | 2 | 3 | 2 | 1 | 4 | 3 |
| Subject 13 | 1 | 2 | 2 | 2 | 1 | 1 | 2 | 3 | 3 | 2 | 1 | 2 |
| Average | 1.1 | 1.6 | 2.3 | 2.1 | 1.5 | 1.2 | 1.8 | 2.6 | 2.7 | 1.1 | 1.8 | 2.0 |
| Std Dev | 0.3 | 0.9 | 0.8 | 1.0 | 0.7 | 0.4 | 0.8 | 1.0 | 1.2 | 0.3 | 1.1 | 0.8 |
| total | 14 | 21 | 30 | 27 | 20 | 16 | 23 | 34 | 35 | 14 | 24 | 26 |

[1]RESONIUM CALCIUM ®, Ca-PSS, Sanofi-Aventis

Example 27: Measurements of Swelling Ratio of the Calcium Polystyrene Sulfonate Resin The swelling ratio was measured by centrifugation method using the following procedure: accurately weigh approximately 1 g of calcium polystyrene sulfonate (Ca-PSS) resin into a 50 mL pre-weighed centrifuge tube. Add approximately 10-15 mL of deionized water (or 0.9% saline solution) to immerse the resin, and shake for a minimum of 30 minutes. Centrifuge at relative centrifuge force (RCF) of 2000×g or 2500×g for 30 minutes and carefully remove the supernatant. Determine the wet sample weight and calculate the ratio between the wet sample weight versus the dry sample weight. The swelling ratio of Ca-PSS is correlated to the percentage of DVB cross-linking. There was no significant difference between swelling ratios measured in water versus those determined in 0.9% saline when the % DVB cross-linking was above 1.0% (FIG. 1 and Table 1).

Figure 11:
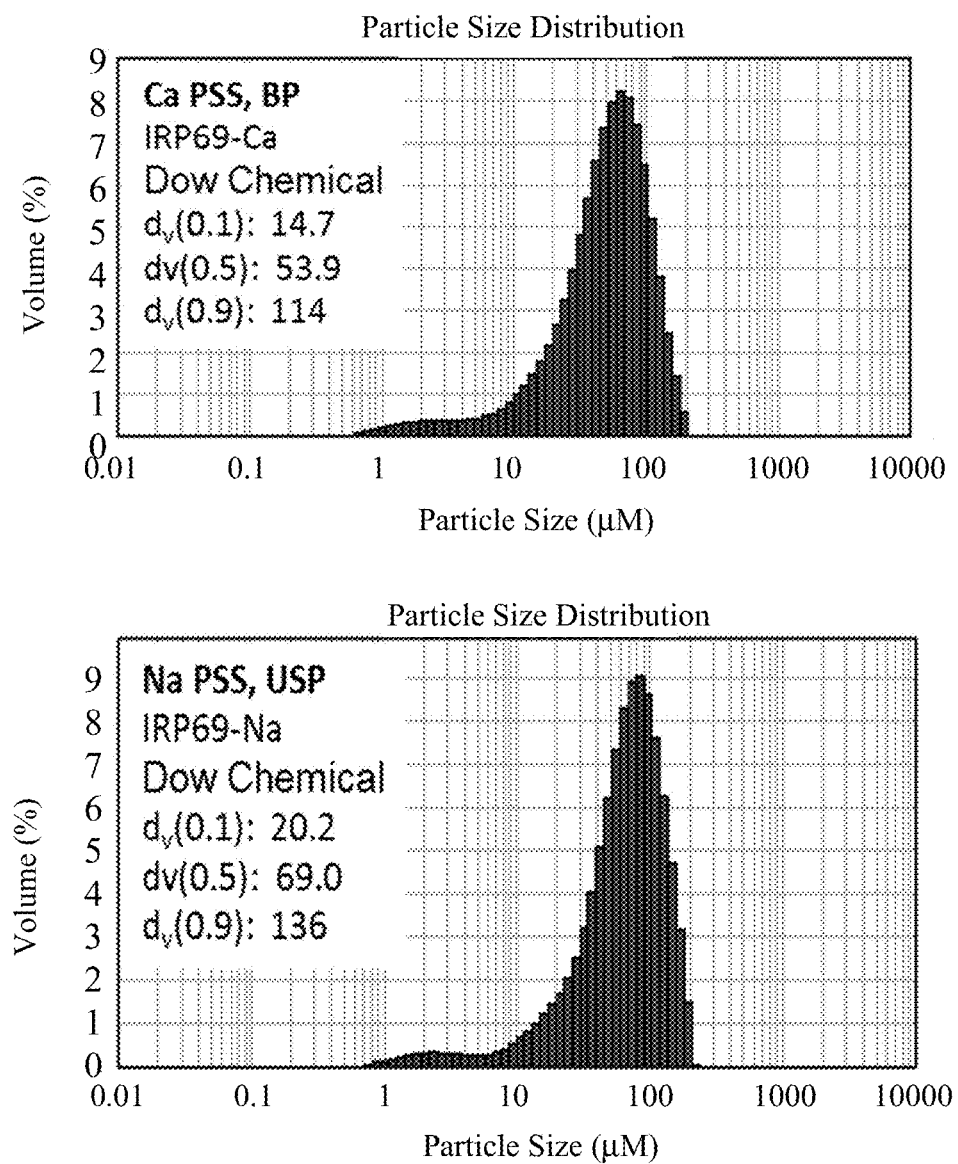
FIG. 11: shows particle size analysis data (laser diffraction) for samples of Na-PSS, USP and Ca-PSS, BP obtained from several different manufacturers compared to Example 10 of the present invention.
Figure 11:
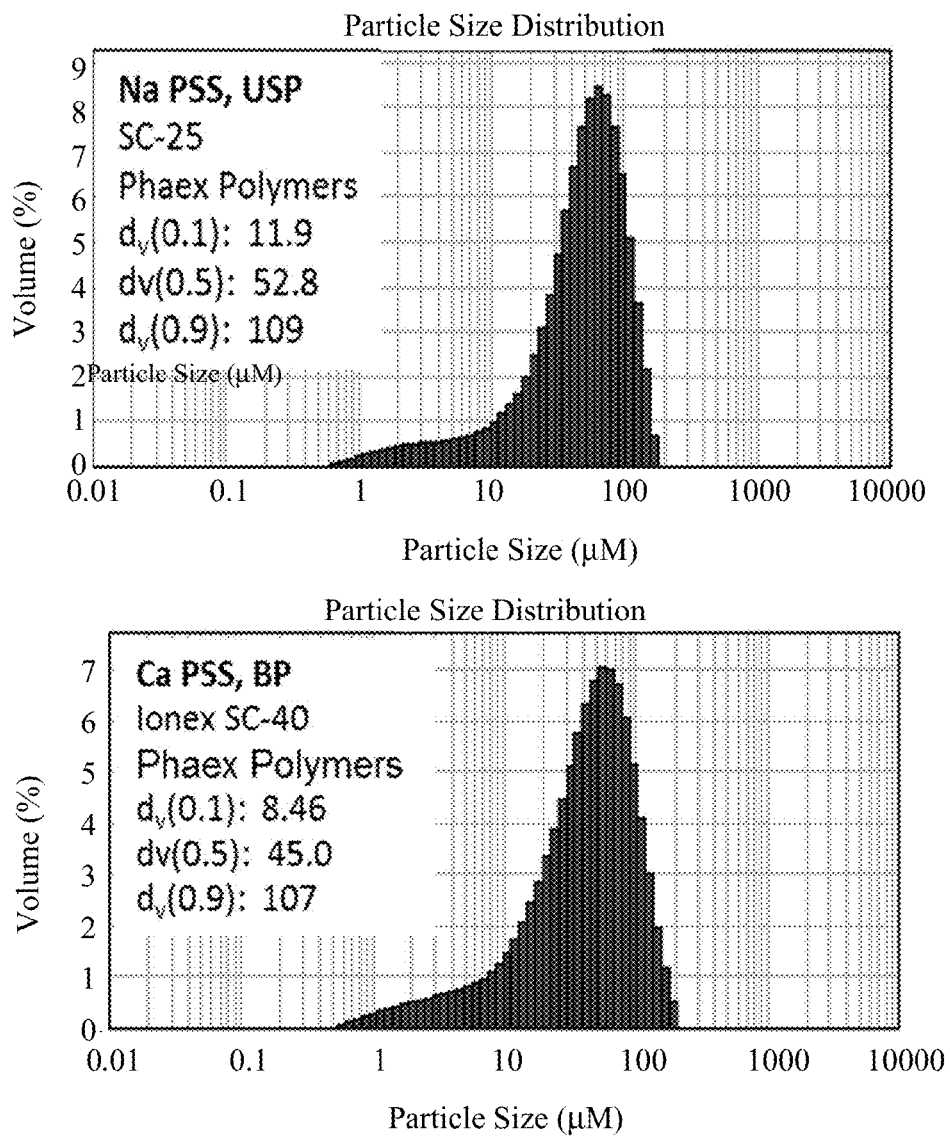
Figure 11:
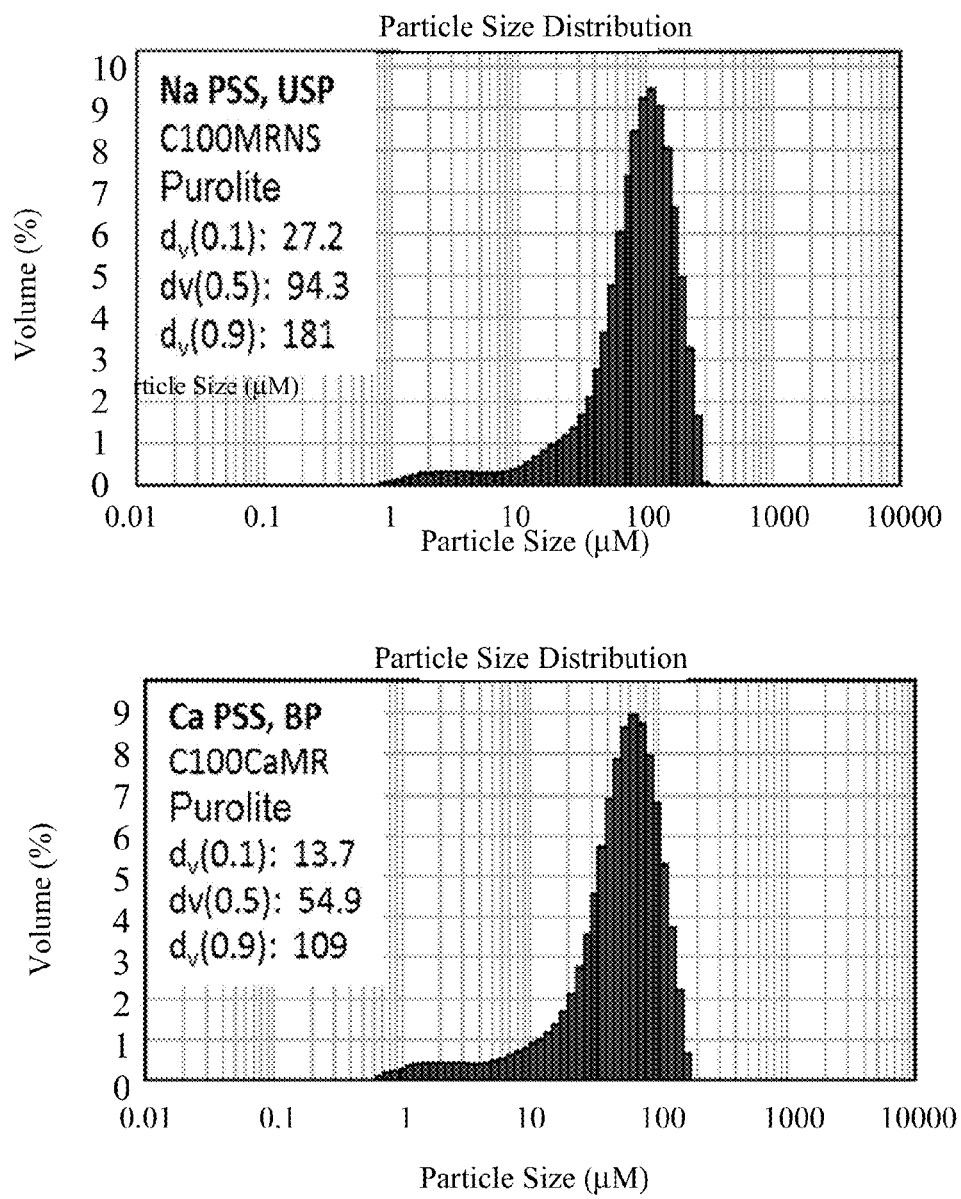
Figure 11:
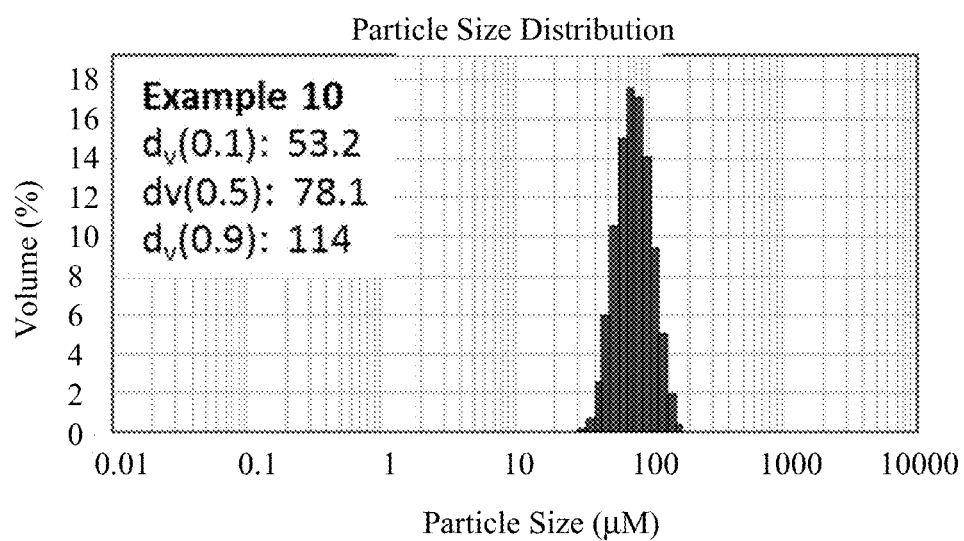

Example 28: Particle Size Analysis of Calcium and Sodium Polystyrene Sulfonate Resin Particle Size was Measured by Laser Diffraction Using a Malvern Mastersizer 2000. Samples were introduced as suspensions in DI water into a hydro2000S sampler, sonicated if necessary to break down agglomeration, and allowed 5-10 minutes circulation for equilibration prior to measurements. Results are presented in FIG. 11 (FIG. 11).

TABLE 5

SWELLING RATIO COMPARISON IN WATER AND 0.9% SALINE

| CA-PSS resin | Swelling ratio in Water (RCF = 2000 × g) | Swelling ratio in 0.9% Saline (RCF = 2000 × g) |
|---|---|---|
| Phaex SC40, BP grade; 8% DVB cross-linking[1] | 2.18 | 2.26 |
| Phaex SC47, JP grade; 8% cross-linking[2] | 2.25 | 2.27 |
| SKK Argamate 89.29% powder; 8% cross-linking[3] | 2.11 | 2.11 |
| Example 1; 8% DVB cross-linking | 2.10 | 2.08 |
| Example 2; 4% DVB cross-linking | 2.92 | 2.82 |
| Example 3; 2% DVB cross-linking | 4.03 | 3.72 |

TABLE 5-continued

SWELLING RATIO COMPARISON IN
WATER AND 0.9% SALINE

| CA-PSS resin | Swelling ratio in Water (RCF = 2000 × g) | Swelling ratio in 0.9% Saline (RCF = 2000 × g) |
|---|---|---|
| Example 8; 1.12% DVB cross-linking | 7.87 | 7.80 |
| Example 7; 0.96% DVB cross-linking | 9.08 | 8.11 |

[1]Ca-PSS, British Pharmacopeia (BP) grade, manufactured by Phaex Polymers PVT LTD, Maharashtra, India;
[2]Ca-PSS, Japanese Pharmacopeia (JP) grade, Phaex Polymers PVT LTD, Maharashtra, India;
[3]Ca-PSS, JP grade, manufactured by Sanwa Kagaku Kenkyusho Co., Ltd., Japan.

Example 29: Preparation of Calcium Polystyrene Sulfonate (Ca-PSS) with 1.8% Divinylbenzene (DVB)

Intermediate Polystyrene beads at 1.8% DVB: To a jacketed cylindrical vessel equipped with an overhead stirrer, thermocouple, and $N_2$ inlet, was added polyvinyl alcohol (0.1 kg), NaCl (1.0 kg), $NaNO_2$ (0.02 kg) and water (100 kg). The mixture was stirred and heated to 85° C. to dissolve solids, then cooled to 25° C. To a separate vessel equipped with an overhead stirrer and $N_2$ inlet was added styrene (14.7 kg), divinylbenzene (0.34 kg, 80% Technical Grade), and benzoyl peroxide (0.85 kg, 75%, stabilized with water), and the mixture was agitated to combine monomers and initiator. The aqueous and monomer liquids were then mixed in 4 portions (~25-30 L aqueous, ~5 L monomer) and homogenized using both a steel pitched blade agitator (600-800 RPM), and by a high mixer (IKA T-50 Ultra Turrax, 3000 RPM). The resulting mixtures were transferred to a jacketed cylindrical vessel equipped with an overhead stirrer, thermocouple, and $N_2$ inlet, and heated to 92° C. for 16 hours, and then cooled to 45° C. for isolation.

The suspension of polystyrene beads was filtered, and the beads were re-suspended in water (70 kg), agitated and heated to 80° C. for 20 minutes, then filtered. The beads were re-suspended in 2-propanol (55 kg), agitated and heated to 75° C. for 20 minutes, then filtered, and dried under vacuum to give 11 kg of polystyrene beads as a white powder which was used in the next step without further purification.

Example 29

To a jacketed cylindrical vessel equipped with an overhead stirrer, thermocouple and $N_2$ inlet, was added Polystyrene beads (7 kg) and sulfuric acid (98%, 156 kg). The mixture was agitated to form a suspension and warmed to 100-105° C. for 16 hours. The dark mixture was cooled to 45° C., and transferred slowly into cold water (90 kg). The mixture was filtered, and the sulfonated beads were repeatedly washed as a slurry with water at ~50° C., and filtered until the effluent contained <0.05 M sulfuric acid. The beads were washed with aqueous calcium acetate solution (34 kg water, 8.4 kg $Ca(OAc)_2$) at 50° C., agitated for 2 hours, then filtered. The beads were washed again with aqueous calcium acetate solution (34 kg water, 8.4 kg $Ca(OAc)_2$) at 50° C., agitated for 2 hours, and filtered. The beads were washed with water until the calcium content in the effluent was <1000 ppm. The filter cake was then dried under vacuum to give 12.76 kg of Example 29 as a brown solid. Particle Size: d(0.1)=13 μm; d(0.5)=29 μm; d(0.9)=52 μm. Ca-salt 8.8 wt % (dry basis, by titration); K+ exchange capacity 1.3 mEq/g (per BP, dry basis); residual styrene <1 ppm; water content 5.6% (Karl Fisher); swelling ratio 5.7 (dry basis).

Example 30: Preparation of Sodium Polystyrene Sulfonate (Na-PSS) with 1.8% Divinylbenzene (DVB)

To a jacketed vessel equipped with an overhead stirrer, thermocouple, and $N_2$ inlet, was added $Ag_2SO_4$ (2 g) and conc. $H_2SO_4$ (1050 mL). The mixture was warmed to 80° C. to dissolve. Intermediate polystyrene beads, prepared according to Example 29 (100 g), were added and the suspension warmed to 100° C. for 4 hours. The mixture was cooled to 60° C., and an equal volume of 30% aqueous $H_2SO_4$ (1050 mL) was slowly added to the mixture keeping the temperature below 85° C. The mixture was then filtered. A portion (approximately ⅓) of this filter cake was repeatedly washed and filtered as a slurry with water at ~50° C., until the effluent pH>4. Then, the filter cake was washed on the filter with IPA (2×150 mL). The beads were suspended in aqueous NaOH (200 mL water, 2 g NaOH) and agitated for 2 hours, then filtered. The material was then suspended again in aqueous NaOH (200 mL water, 2 g NaOH) and agitated for 2 hours, then filtered. The material was then washed successively with hot water (3×250 mL), IPA (2×75 mL), and Ethanol (50 mL). The beads were then dried in a vacuum oven at 50° C. to give 17.2 g Example 30 as a brown solid. Na-salt 8.9% by weight; particle size in water 20-135 μm (visual microscopy).

Example 31: Preparation of Calcium Polystyrene Sulfonate (Ca-PSS) with 1.8% Divinylbenzene (DVB)

A portion (approximately ⅓) of sulfonated resin from Example 30, was repeatedly washed and filtered as a slurry with water at ~50° C., until the effluent pH>4. Then, the filter cake was washed on the filter with IPA (2×150 mL). The beads were then suspended in aqueous calcium acetate solution (180 g water, 20 g $Ca(OAc)_2$) at ambient temperature, agitated for 2 hours, then filtered. The beads were again suspended in aqueous calcium acetate solution (180 g water, 20 g $Ca(OAc)_2$) at ambient temperature, agitated for 2 hours, then filtered. The beads were washed repeatedly with water to remove soluble calcium. The beads were then washed with IPA (2×75 mL), and ethanol (50 mL). The beads were then dried in a vacuum oven at 50° C. to give 16.7 g of Example 31 as a brown solid. Ca-salt 7.45% by weight; particle size in water 12-94 μm (visual microscopy).

Example 32: Preparation of Calcium Polystyrene Sulfonate (Ca-PSS) with 1.8% Divinylbenzene (DVB)

Intermediate Polystyrene Beads at 1.8% DVB:
To a jacketed cylindrical vessel equipped with an overhead stirrer, thermocouple, and $N_2$ inlet, was added polyvinyl alcohol (0.51 kg), NaCl (5.1 kg), $NaNO_2$ (0.10 kg) and water (470 kg). The mixture was stirred and heated to 75° C. to form a slightly turbid solution, then cooled to 25° C. To a separate jacketed cylindrical vessel equipped with an overhead stirrer, thermocouple, and $N_2$ inlet, was added styrene (75 kg), divinylbenzene (1.8 kg, 80% Technical Grade), and benzoyl peroxide (4.3 kg, 75%, stabilized with water), and the mixture was agitated to combine monomers and initiator. The monomer-initiator mixture was added to the vessel containing the aqueous solution and agitated for 0.5 hours to form a coarse suspension. This coarse suspension was then homogenized by pumping the liquid twice through a high shear mixer. The resulting homogenized mixture was heated to 92° C. for 5 hours, and then cooled to 20-30° C. for isolation.

The suspension of polystyrene beads was partitioned by centrifugation-decantation to remove small particles, and to wash the beads. The final slurry was isolated by filtration, or centrifugation, and dried under vacuum to give 55 kg of polystyrene beads as a white powder. Particle size: d(0.1)>5 µm; d (0.9)=<40 µm.

Example 32

To a jacketed cylindrical vessel equipped with an overhead stirrer, thermocouple, and $N_2$ inlet, was added Polystyrene beads (15 kg), and sulfuric acid (98%, 345 kg). The mixture was stirred to form a suspension then warmed to 100-105° C. for 3.5-4 hours. The dark mixture was cooled to 35° C., and diluted slowly with cold water (150 kg). The mixture was filtered on an agitated Neutsche type filter, and the sulfonated beads were washed with water. Aqueous calcium acetate solution (180 kg, 10% wt) was added, the mixture was agitated for 2 hours, then filtered. Aqueous calcium acetate solution (180 kg, 10% wt) was added, the mixture was agitated for 2 hours, then filtered. The beads were washed with water. The filter cake was washed with acetone and then dried under vacuum to give 25 kg of Example 32 as a light brown powder. Particle Size: d(0.1)=19 µm; d(0.5)=35 µm; d(0.9)=54 µm. Ca-salt 9.5 wt % (dry basis, by titration); K+ exchange capacity 1.5 mEq/g (per BP, dry basis); residual styrene <1 ppm; swelling ratio 5.6 (as is).

Example 33: Preparation of Calcium Polystyrene Sulfonate (Ca-PSS) with 1.8% Divinylbenzene (DVB)

Example 33 was prepared on 10 kg scale using methods analogous to those described for Example 32 with the following modifications: polymerization initiator was tert-butyl-peroxy-ethyl-hexanoate; a particle size control (Dv0.5) of 50 microns was achieved via a jetting process (See e.g., Dow Chemical, U.S. Pat. No. 4,444,961). After sulfonation and calcium exchange; drying of the Ca-PSS was achieved via a fluidized bed dryer. Particle Size (dry): d(0.1)=38; d(0.5)=51; d(0.9)=62. Ca-salt 9.7 wt % (by titration); K+ exchange capacity 1.5 mEq/g (per BP).

Example 34: Preparation of Calcium Polystyrene Sulfonate (Ca-PSS) with 2.5% Divinylbenzene (DVB)

Example 34 was prepared on 500 g scale using methods analogous to those described for Example 33, and incorporating 2.5% divinylbenzene. Particle Size: d(0.1)=54 µm; d(0.5)=75 µm; d(0.9)=104 µm. K+ exchange capacity 1.7 mEq/g (per BP); swelling ratio 3.7.

Example 35: Preparation of Calcium Polystyrene Sulfonate (Ca-PSS) with 1.5% Divinylbenzene (DVB)

Example 35 was prepared on 500 g scale using methods analogous to those described for Example 33, and incorporating 1.5% divinylbenzene. Particle Size: d(0.1)=54 µm; d(0.5)=78 µm; d(0.9)=114 µm. K+ exchange capacity 1.4 mEq/g (per BP); swelling ratio 4.5.

Example 36: Preparation of Calcium Polystyrene Sulfonate (Ca-PSS) with 1.6% Divinylbenzene (DVB)

Example 36 was prepared on 500 g scale using methods analogous to those described for Example 33, and incorporating 1.6% divinylbenzene. Particle Size: d(0.1)=53 µm; d(0.5)=75 µm; d(0.9)=106 µm. K+ exchange capacity 1.5 mEq/g (per BP); swelling ratio 4.5.

Example 37: Preparation of Calcium Polystyrene Sulfonate (Ca-PSS) with 1.7% Divinylbenzene (DVB)

Example 37 was prepared on 500 g scale using methods analogous to those described for Example 33, and incorporating 1.7% divinylbenzene. Particle Size: d(0.1)=53 µm; d(0.5)=74 µm; d(0.9)=105 K+ exchange capacity 1.5 mEq/g (per BP); swelling ratio 4.3.

Example 38: Preparation of Calcium Polystyrene Sulfonate (Ca-PSS) with 1.8% Divinylbenzene (DVB)

Example 38 was prepared on 500 g scale using methods analogous to those described for Example 33, and incorporating 1.8% divinylbenzene. Particle Size: d(0.1)=51 µm; d(0.5)=77 µm; d(0.9)=114 µm. K+ exchange capacity 1.5 mEq/g (per BP); swelling ratio 4.1.

Example 39: Calcium Polystyrene Sulfonate (Ca-PSS) with 1.8% Divinylbenzene (DVB)

Example 39 was prepared on 5.6 kg scale using methods analogous to those described for Example 29. Particle Size: d(0.1)=30 µm; d(0.5)=56 µm; d(0.9)=91 µm. K+ exchange capacity 1.4 mEq/g (per BP); swelling ratio 5.1.

Example 40: Powder for Oral Suspension (POS), "Strawberry Smoothie" Flavor and Consistency, Sodium Free Without a suspending agent, some Examples of the instant disclosure settle out from water in a few minutes, highlighting the need for a viscosifying system. Hydrocolloids retard particle sedimentation by increasing viscosity; however, at too high a viscosity, the formulation becomes un-drinkable. To determine a maximum viscosity for a drinkable liquid, the viscosity of commercial liquid products were measured (Table 6, below). Data were generated using a Brookfield EV-I viscometer using a small sample size adapter with spindle 18, starting at 60 RPM and decreasing speed as necessary to obtain an in-range reading. A target viscosity of less than 400 cps was selected for a drinkable product, similar to a fruit-based blended smoothie.

TABLE 6

Viscosity of commercial liquid products

| Product | Viscosity (cps)* | Product | Viscosity (cps)* |
|---|---|---|---|
| Hershey's Chocolate Syrup | 7528 | | |
| Vermont Maid Syrup | 635 | | |

TABLE 6-continued

Viscosity of commercial liquid products

| Product Viscosity (cps)* | Product Viscosity (cps)* |
|---|---|
| Odwalla Strawberry Banana Smoothie | 302 |
| Pepto Bismol | 195 |
| Syrpalta (Oral Dosing Vehicle) | 86 |
| Heavy Cream | 18 |
| Light Cream | 7 |

*Note: it is understood to one skilled in the art that viscosity measurement is a complicated field of science, and a single number may be an oversimplification of the system.

Additional criteria included a formulation that could readily disperse ~5 g of polymer in less than 35 mL water, and creation of a stable suspension for the anticipated duration of consumption (approximately 5 minutes). Last, it was desired to eliminate sodium from the formulation since excess consumption of this electrolyte is contraindicated in kidney failure patients. In addition, a pH of ~3-3.5 was chosen to be compatible with the stability and flavor properties of a fruit-themed formulation. The composition in Table 7, prepared from Example 39, achieves the above design considerations, and when added to ~28-30 mL of water readily wets and suspends after brief and gentle mixing (inverting 4-5 times in a closed container).

TABLE 7

Composition of Example 40 "strawberry smoothie" powder-for-oral-suspension

| Ingredient | g/30 mL Suspension |
|---|---|
| Calcium citrate tetrahydrate | 0.049 |
| Citric acid, anhydrous | 0.150 |
| Sucralose | 0.030 |
| Michaelock N&A Strawberry Flavor #2342 | 0.075 |
| Methylcellulose A4C | 0.150 |
| FD&C Red 3 (0.1% solution) | 0.430 |
| Titanium Dioxide | 0.060 |
| Example 39 | 5.00 |
| Water | Qs to 30 mL |
| | (Resulting pH: 3.41) |

Example 41: Ready-to-Use (RTU) "Strawberry Smoothie" Drinkable Suspension

Example 41, a ready-to-use variant of Example 40, was prepared from Example 39 by including a preservative system in the reconstituted formulation, replacing anhydrous citric acid with benzoic acid (0.030 g). This formulation is also sodium-free.

Example 42: Ready-to-Use (RTU) Spoonable Formulation, Chocolate Flavored, Sodium Free Higher viscosity formulations were found to attenuate the sensation of grittiness and improve the mouth feel characteristics of some Examples disclosed herein (see Biological Example 14). Example 42 is a "spoonable" yoghurt/gel based formulation that was developed with a chocolate "indulgent" flavor theme (Table 8). This formulation also avoids sodium-containing excipients and has a near neutral pH (5.0), consistent with the flavor and stability requirements of the flavoring agent.

TABLE 8

Composition of Example 42, a "spoonable" chocolate-themed formulation

| Ingredient | g/30 mL Suspension |
|---|---|
| Calcium citrate tetrahydrate | 0.003 |
| Citric acid, anhydrous | 0.004 |
| Sucralose | 0.030 |
| Xanthan gum | 0.165 |
| Natural Chocolate Flavor #37620 | 0.120 |
| Sorbic acid | 0.015 |
| Example 39 | 5.00 |
| Water | 25 g |
| | (Resulting pH: 5.0) |

Example 43: Ready-to-Use (RTU) "Spoonable" Formulation, Strawberry Flavored, Sodium Free)

Example 43 was prepared applying the principles described in Examples 40-42 and Biological Example 14 to afford a fruit-themed, lower pH spoonable formulation (Table 9).

TABLE 9

Composition of Example 43, a "spoonable," strawberry flavored sodium free formulation

| Ingredient | g/30 mL Suspension |
|---|---|
| Calcium citrate tetrahydrate | 0.042 |
| Citric acid, anhydrous | 0.130 |
| Sucralose | 0.030 |
| Xanthan gum | 0.135 |
| Michaelock N&A strawberry flavor #2342 | 0.075 |
| FD&C Red 3 (0.1% solution) | 0.430 |
| Titanium dioxide | 0.060 |
| Benzoic acid | 0.025 |
| Example 39 | 5.00 |
| Water | 25 g |
| | (Resulting pH: 3.3) |

Example 44: Chewable Tablet Formulation, Citrus Flavored

A chewable tablet was designed by first determining an appropriate tablet hardness for a chewable dosage form: the tablets must be hard enough to hold together through processing and shipping, while still maintaining a chewable texture. Accordingly, the hardness of several commercially available chewable OTC products were measured (Table 10), after which a tablet hardness target of approximately 9-15 kp was set.

TABLE 10

Hardness of OTC chewable tablets

| Product | Hardness (kp) |
|---|---|
| Tums Kids Antacid | 7.4 |
| Tums Smoothies | 10.4 |
| Spectravite Senior Chewable | 11.9 |
| Tums Regular | 12.4 |
| Centrum Children's Chewable Vitamins | 12.9 |
| CVS Children's Complete Chewable Vitamins | 15.7 |
| Flintstones Chewable Vitamins with Iron | 16.4 |

Apart from the active ingredient, a chewable tablet is composed primarily (but not exclusively) of a tablet binder, hence multiple tablet binders were explored in pilot tableting exercises. These included direct compression Lactose (Supertab 11SD—DSM), direct compression Mannitol (Pearlitol 100SD—Roquette), sucrose (Di-Pac—Domino), —sodium starch glycolate All-in-One (ProSolv Easytab SP—JRS) and a mannitol based All-in-One (ProSolv ODT G2—JRS). Drug load was explored with the goal of achieving a high percentage. Example 39 was subjected to iterative screening in a number of the binder systems listed above, and an approximately 30% loading was achieved in a chewable tablet format. Tablets were created based on a 3 g gross tablet weight, with 900 mg Example 39 per tablet. Blends were loaded into a 25 mm diameter tablet die and a Carver hydraulic hand press (Model 3912) was used to compress the blends to a maximum force of 15,000 lbs to afford tablets.

ProSolv Easytab SP had an extremely chalky mouth feel and was dropped from consideration, whereas both ProSolv ODT G2 and Pearlitol 100SD had similar, smooth mouth feels and were advanced. Active ingredient loading was re-explored, and while a 41.66% drug load could not afford sufficiently hard tablets, a load of 33.3% was acceptable. Next, the sweet/sour properties of the tablets were determined. As sucralose and citric acid had proven to be an effective pairing in the suspension formulations, varying levels of these were evaluated in both binder systems (Pearlitol 100SD w/additives and ProSolv ODT G2). A final sucralose level of 0.15% and citric acid of 1.5% provided the desired sweet/sour balance. Finally, flavor candidates were screened in both leading base binder systems, and included fruit flavored themes such as citrus, orange, mixed berry, strawberry and punch. These were incorporated into the mimetic (excipient) base starting at 0.25%, and adjusting up or down as appropriate. When the final mimetic (excipient) flavor systems (Pearlitol 100 SD with additives and ProSolv) were compared side-by-side, it was apparent that the Pearlitol (mannitol-based) system had a better mouth feel overall, and was selected as a preferred system. This formulation, Example 44, is shown below in Table 11.

TABLE 11

Composition of Example 44, a chewable tablet formulation

| Ingredient | Mannitol based formulation g/100 g |
|---|---|
| Example 39 | 33.33 |
| Colloidal Silicon Dioxide, NF-M-5P | 0.85 |
| Sucralose, NF | 0.15 |
| Magnesium Stearate, NF | 1.35 |
| Croscarmellose Sodium, NF Ac-DI-Sol SD-711 NF | 2.80 |
| Avicel CE-15 | 5.30 |
| Citric Acid, Anhydrous | 1.50 |
| Natural Orange Flavor #SC356177 | 0.45 |
| Mannitol, USP Pearlitol 100 SD | 54.27 |

Example 45: Ready-to-Use (RTU) "Smoothie" Drinkable Suspension, Orange and Vanilla Flavors Example 37 was formulated into both an orange- and vanilla-flavored ready-to-use drinkable "smoothie" using the procedures and concepts described in Example 40 and Example 41. Both formulations are sodium-free.

TABLE 12

Compositions of Example 45, drinkable "smoothie" in both orange and vanilla flavor

| Ingredient | Orange formulation (g/30 mL suspension) | Vanilla formulation (g/30 mL suspension) |
|---|---|---|
| Calcium Citrate Tetrahydrate | 0.149 | 0.066 |
| Benzoic Acid | 0.030 | — |
| Sorbic Acid | — | 0.015 |
| Citric Acid Anhydrous | 0.150 | 0.004 |
| Sucralose | 0.030 | 0.030 |
| Natural Orange WONF FV7466 | 0.150 | — |
| SuperVan Art Vanilla VM36 | — | 0.150 |
| Methylcellulose A4C | 0.165 | 0.165 |
| Titanium Dioxide | — | 0.120 |
| Example 37 | 5.624 | 5.624 |
| Water | 25.72 | 25.68 |

Example 46: Powder for Oral Suspension (POS), "Smoothie" Consistency, Orange- and Vanilla-Flavored, Sodium Free Example 37 was formulated into both an orange- and vanilla-flavored powder-for-oral-suspension using the procedures and concepts described in Example 40. Both formulations are sodium-free, and reconstitute to a drinkable suspension with the consistency of a fruit-based "smoothie" upon addition to one ounce of water and brief agitation.

TABLE 13

Compositions of Example 46, powders for oral suspension in both orange and vanilla flavor

| Ingredient | Orange formulation (g/30 mL suspension) | Vanilla formulation (g/30 mL suspension) |
|---|---|---|
| Calcium Citrate Tetrahydrate | 0.149 | 0.066 |
| Citric Acid Anhydrous | 0.150 | 0.013 |
| Sucralose | 0.030 | 0.030 |
| Artificial orange flavored powder FV653 | 0.150 | — |
| Vanillin powder | — | 0.060 |
| Methylcellulose A4C | 0.165 | 0.165 |
| Titanium Dioxide | — | 0.120 |
| Example 37 (includes 11.1% water (KF)) | 5.624 | 5.624 |

Example 47: "Spoonable" Formulation, Orange- and Vanilla-Flavored, Sodium Free Example 37 was formulated into ready-to-use "spoonable" orange- and vanilla-flavored formulations using the procedures and concepts described in Example 42 and Example 43. Both formulations are sodium-free, and their composition is illustrated in Table 14.

TABLE 14

Compositions of Example 47, RTU orange- and vanilla-flavored "spoonable" suspensions

| Ingredient | Orange formulation (g/30 mL suspension) | Vanilla formulation (g/30 mL suspension) |
| --- | --- | --- |
| Calcium Citrate Tetrahydrate | 0.149 | 0.066 |
| Benzoic Acid | 0.030 | — |
| Sorbic Acid | — | 0.015 |
| Citric Acid Anhydrous | 0.150 | 0.004 |
| Sucralose | 0.030 | 0.030 |
| Natural Orange WONF FV7466 | 0.150 | — |
| SuperVan Art Vanilla VM36 | — | 0.150 |
| Xanthan Gum CP | 0.210 | 0.180 |
| Titanium Dioxide | — | 0.120 |
| Example 37 (includes 11.1% water (KF)) | 5.624 | 5.624 |
| Water | 25.0 | 25.0 |

Biological Example 1: Preparation of Mice for In Vivo Animal Studies

Study Preparation:

Male CD-1 mice ~25-35 grams (Charles River) were used for these studies. Upon arrival animals were allowed to acclimate in standard cages, on standard chow before study initiation. The day of diet acclimation initiation, body weights were obtained and mice were placed in metabolic cages. The animals were fed ad libitum during the study. Mice were provided normal powdered chow or study compound mixed in powdered chow at the designated percentage for a period of 48 hours (to ensure the study diet has passed the length of the GI and animals achieve "steady state."). Food and water measurements were recorded upon placement of animals in metabolic cages, and every 24 hours until study completion. After 48 hours of acclimation, the 24 hour collection period began. Clean collection tubes were placed on the cage. Mice were provided their designated study diet during the collection period. Urine and feces were collected at the end of this 24 hour period. Food and water was weighed again to determine the amount consumed over the study period.

Sample Processing and Analysis:

Urine and feces were collected directly into pre-weighed tubes placed on the metabolic racks. At the collection time the urine tubes were capped and the urine was weighed. The urine was then pipetted into a pair of 96 well-plates with 0.2 ml of each urine sample added to each plate. One plate was acidified (20 μl of 6 N HCl per sample). Plates were stored frozen until analysis. The feces were removed from the metabolic cages, the jars were capped, wet weights were recorded, and then the samples were frozen for ~3-4 hours. The feces were then dried on a lyophilizer for at least 3 days before a dry weight was taken and fecal fluid content was calculated. Feces and urine were analyzed by microwave plasma-atomic emission spectroscopy (MP-AES) or ion chromatography (IC) for ion content.

Biological Example 2: Preparation of Rats for In Vivo Animal Studies

Study Preparation:

Male Sprague Dawley (Charles River) rats (~200-250 gm) were used for these studies. Upon arrival animals were allowed to acclimate in standard cages, on standard chow, for at least 2 days prior to study initiation. The day prior to being placed in metabolic cages, body weights were obtained and rats were provided normal powdered chow or study compound in powder chow, via a J-Feeder, beginning at ~1:00 μm (to ensure the study diet has passed the length of the GI). The day of the study, rats were transferred to metabolic cages at ~3:30 μm, where they were provided their designated study diet for 16 hours. Tare weights of food and water were obtained prior to animals being placed in the cages. Urine and feces were collected ~16 hours later. Food and water was weighed again to determine the amount consumed over the study period.

Chow Formulation:

Chow meal (Standard rodent chow, 2018C) was weighed out into a mixing bowl and placed on a stand mixer (KitchenAid). PSS was weighed out and added to the chow to achieve the desired final concentration (2-8% polymer in chow by weight). The mixer was set to stir on low for at least 10 minutes to evenly distribute the polymer in the chow. The chow was then transferred to a labeled zip-lock storage bag.

Sample Processing and Analysis:

Urine was collected directly into pre-weighed 50 ml conical tubes placed inside the urine collectors on the metabolic racks. At the collection time the urine tubes were capped and the urine was weighed. The urine was then pipetted into a pair of 96-well plates with 0.5 ml of each urine sample added to each plate. One plate was acidified (50 μl of 6 N HCl per sample). Both plates were submitted on the same day for bioanalytical analysis (or were placed in a −20 freezer). The feces were transferred from the metabolic collectors to pre-weighed capped jars, wet weights were recorded, and then the samples were frozen for ~3-4 hours. The feces were dried on a lyophilizer for at least 3 days before a dry weight was taken and fecal fluid content calculated. The feces were then placed on a homogenizer and ground to a fine powder. For each sample, two aliquots were weighed out. 500 mg was weighed into a 50 ml conical tube, and 50 mg into an eppindorf tube. Feces and urine were analyzed by MP-AES or IC for ion content.

Figure 2:
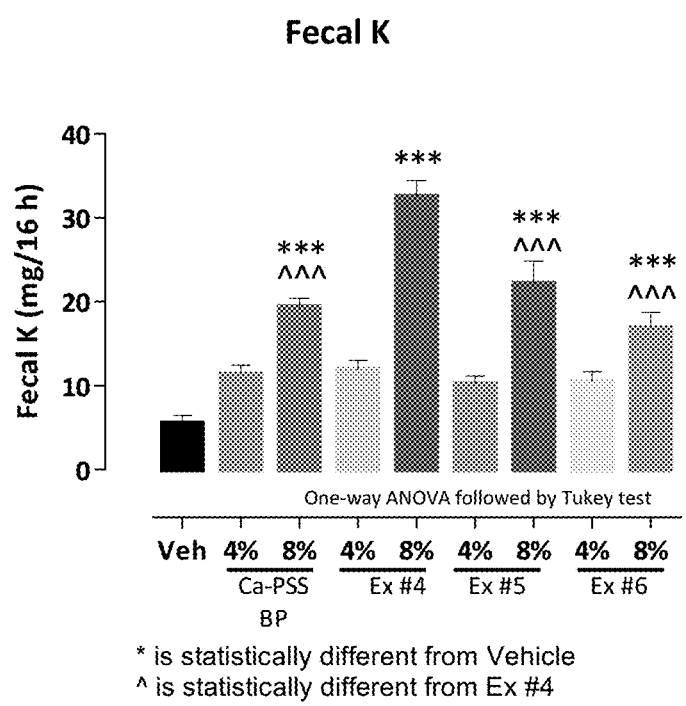
FIG. 2: shows the fecal $K^+$ excretion of rats dosed with Ca-PSS polymers with differing levels of crosslinking (2%, 4% and 8% DVB crosslinking) blended into chow at 4% or 8% wt/wt. The highest fecal $K^+$ was seen in the group that was fed a 2% DVB crosslinked polymer, when said polymer was present at 8% wt/wt in chow.

Biological Example 3: Effects on Fecal Potassium Levels in Rats Upon Dosing with Ca-PSS Using the methods described in Biological Example 2, rats were dosed Ca-PSS blended into chow at 4% or 8% wt/wt. These polymers had differing levels of crosslinking (2%, 4% and 8% DVB crosslinking). In this experiment, all rats dosed with Ca-PSS blended into the diet at 8% wt/wt had significant increases in K excretion. The highest fecal K was seen in the group that was fed a 2% DVB crosslinked polymer, when said polymer was present at 8% wt/wt in chow. This increase was significantly higher than that observed for the other polymers that were similarly dosed as 8% wt/wt blends in chow (FIG. 2).

Figure 3:
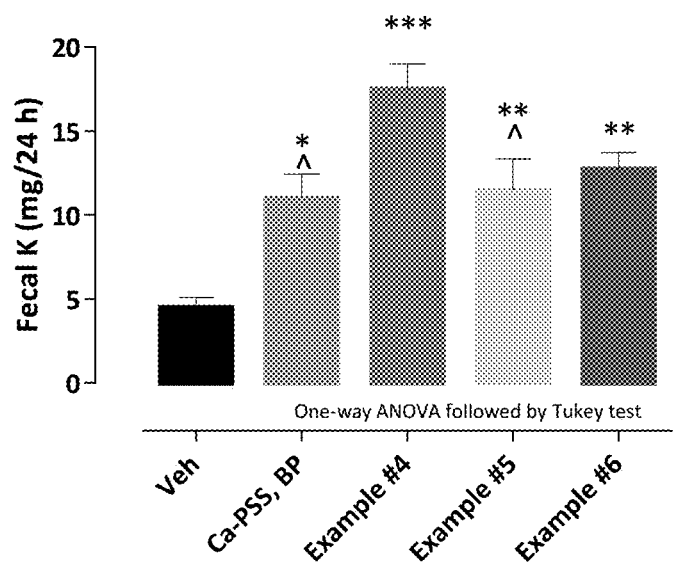
FIG. 3: shows the fecal $K^+$ excretion of mice dosed with Ca-PSS polymers with differing levels of crosslinking (2%, 4% and 8% DVB crosslinking) blended into chow at 8% wt/wt. The highest fecal $K^+$ was seen in the group that was fed a 2% DVB crosslinked polymer.

Biological Example 4: Effects on Potassium Excretion in Mice Upon Dosing with Examples 4, 5, 6, Ca-PSS and BP Using the methods described in Biological Example 1, mice were dose Ca-PSS (i.e., polymers of Formula (I) or a pharmaceutically acceptable salt thereof) blended into chow (Standard 2018 chow) at 8% wt/wt. The polymers had differing levels of crosslinking: 2% DVB, (Example 4); 4% DVB, (Example 5); 8% DVB (Example 6); and Ca-PSS, BP (Ca-PSS, BP with 8% DVB crosslinking) was used as a control. All mice dosed with Ca-PSS blended in the diet at 8% wt/wt had significant increases in K excretion. The highest level of K secretion was seen with the 2% DVB material (Example 4, FIG. 3).

Biological Example 5: Effects on Potassium Excretion in Mice Upon Dosing with Examples 4, 6, 9 and 10

Figure 4:
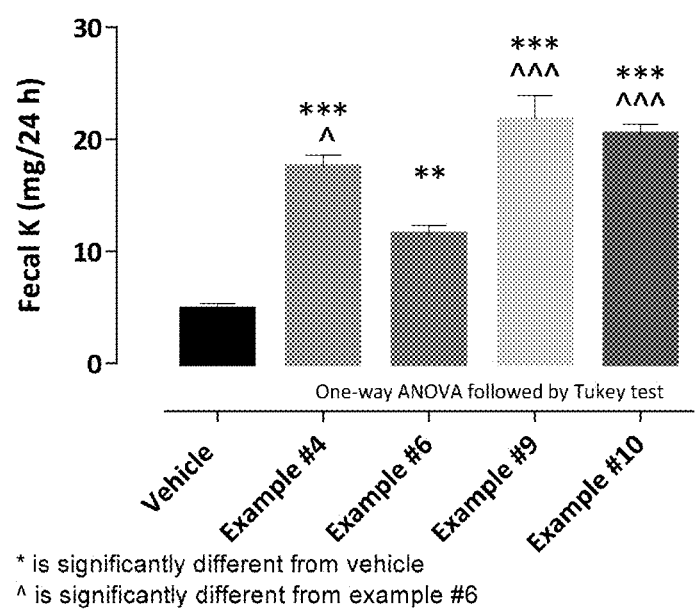
FIG. 4: shows the fecal $K^+$ excretion of mice dosed with Ca-PSS polymers with differing levels of crosslinking (1.6%, 1.8%, 2%, and 8% DVB crosslinking) blended into chow at 8% wt/wt. The level of $K^+$ in the feces was significantly higher with 1.6%, 1.8% and 2% DVB (Examples 9, 10, and 4) compared to the vehicle or 8% DVB (Example 6).

Using the methods in Biological Example 1, mice were dosed Ca-PSS (i.e., polymers of Formula (I) or a pharmaceutically acceptable salt thereof) blended into chow at 8% wt/wt. The test articles included the following: Vehicle (2018 chow); 200-400 mesh Ca-PSS with 2% DVB cross-linking (Example 4); 200-400 mesh Ca-PSS with 8% DVB crosslinking (Example 6), Ca-PSS polymer with 1.6% DVB cross-linking (Example 9), and Ca-PSS material with 1.8% DVB cross-linking (Example 10). All mice dosed with 8% wt/wt Ca-PSS in their diet had significant increases in K excretion. The highest levels of K secretion were seen with polymers possessing DVB levels of 2% or less (FIG. 4). The level of K in the feces was significantly higher with 1.6%, 1.8% and 2% DVB (Examples 9, 10, and 4) compared to vehicle or 8% DVB (Example 6).

Figure 5:
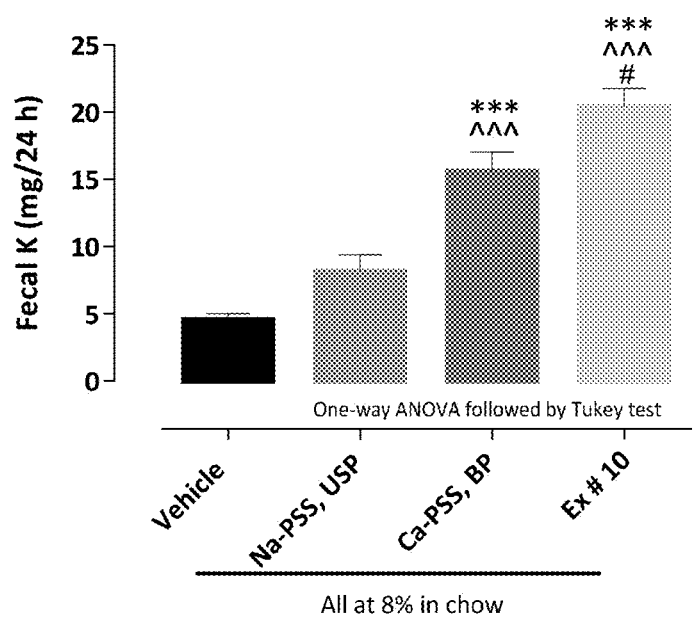
FIG. 5: shows the fecal $K^+$ excretion of mice dosed with Na-PSS, USP, Ca-PSS, BP and Example 10, all blended into chow at 8% wt/wt compared to a vehicle control. Only Ca-PSS, BP and Example 10 afforded significant levels of fecal $K^+$ excretion, and the highest fecal $K^+$ was seen in the group that was fed Example 10.

Biological Example 6: Effects on Fecal Potassium Levels in Mice Upon Dosing with Example 10, Na-PSS, USP, CA-PSS, and/or BP Using the methods in Biological Example 1, mice were dosed Na-PSS, USP, Ca-PSS, BP and Example 10 blended into chow at 8% wt/wt. There was a significant increase in fecal potassium in animals consuming either Ca-PSS, BP or Example 10, with the highest fecal potassium seen in Example 10 (FIG. 5).

Biological Example 7: Effects on Fecal and Urinary Phosphate Levels in Mice Upon Dosing with Example 10

Figure 6:
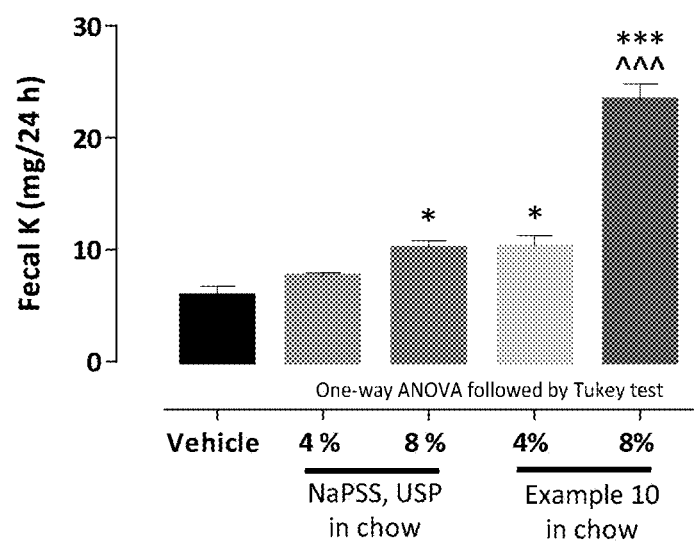
FIG. 6: shows the fecal $K^+$ excretion of mice dosed with Na-PSS, USP and Example 10, both blended into chow at 4% and 8% wt/wt, and compared to a vehicle control. The level of $K^+$ in the feces was significantly higher with Example 10, when present in chow at either 4% or 8% wt/wt, compared to vehicle. Na-PSS, USP afforded significant fecal $K^+$ excretion only when present in chow at 8% wt/wt. The highest fecal $K^+$ was seen in the group that was fed Example 10.
Figure 13:
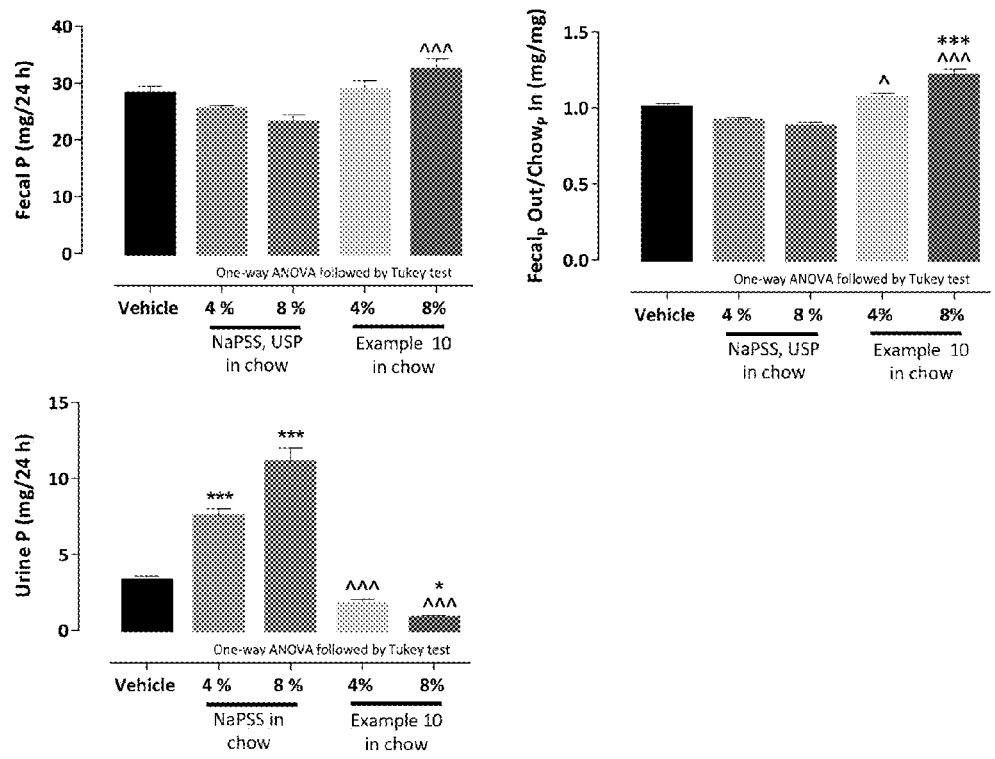
FIG. 13: shows the fecal and urinary excretion of phosphate in mice treated with Example 10 compared to Na-PSS, USP as a control.

Using the methods in Biological Example 1, mice were dosed with Na-PSS, USP and Example 10, blended into chow at 4% and 8% wt/wt. There was a significant increase in fecal potassium in animals consuming either Na-PSS, USP or Example 10 when present at 8% w/w in chow, but only Example 10 showed a significant increase in fecal potassium at 4% wt/wt in chow. In addition there was significantly more K in the feces of mice fed Example 10 versus Na-PSS, USP when these test articles were present at 8% wt/wt in chow (FIG. 6). In addition, the group treated with Example 10 blended into chow at 8% wt/wt had higher levels of fecal phosphate compared to those mice identically dosed with Na-PSS, and lower levels of urinary phosphate compared to groups treated with both Na-PSS or vehicle (FIG. 13).

Biological Example 8: Effects on Fecal Potassium Levels in Mice Upon Dosing with Example 10

Figure 7:
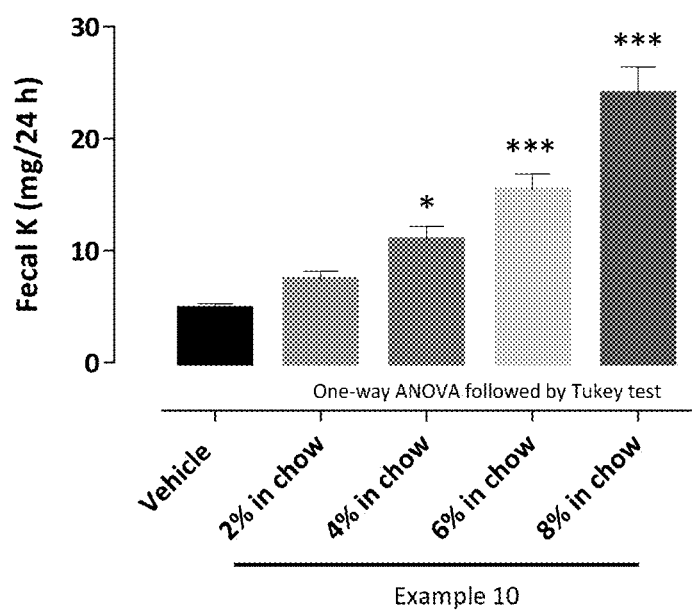
FIG. 7: shows dose-response data for mice fed Example 10 blended into chow at 2%, 4%, 6% and 8%, wt/wt, compared to a vehicle control. The level of $K^+$ in the feces was significantly higher for Example 10 when present in chow at 4%, 6% and 8%, wt/wt, while 2% in chow afforded a trend but was not significant. Increasing amounts of Example 10 blended in chow afford increasing amounts of $K^+$ in the feces.

Using the methods in Biological Example 1, mice were fed increasing amounts of Example 10 blended in chow a 2, 4, 6 and 8% wt/wt. The control group was fed standard rodent chow (Harlan Teklad 2018). There was a dose dependent increase in fecal potassium content with the addition of Example 10 to the chow, with the highest fecal potassium seen in the 8% wt/wt group (FIG. 7).

Biological Example 9: Effects on Fecal Potassium Levels in Mice Upon Dosing with Examples 10, 13, and 18

Figure 8:
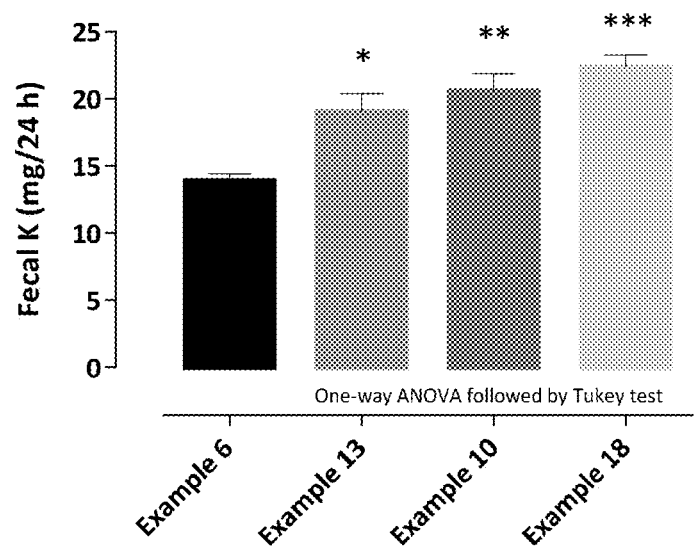
FIG. 8: shows fecal $K^+$ excretion of mice dosed with several Examples from the invention, blended in chow at 8%, wt/wt, and compared to Example 6 as a control. Examples 10, 13 and 18 afforded significant amounts of $K^+$ in the feces.

Using the methods in Biological Example 1, mice were dosed Ca-PSS blended into chow at 8% wt/wt. The test articles included Example 10, Example 13 and Example 18; Example 6 served as a control. The level of $K^+$ in the feces was significantly higher for Examples 32, 35, and 41 compared to Example 6. (FIG. 8).

Biological Example 10: Effects on Fecal Potassium Levels in Mice Upon Dosing with Examples 20 and 21

Figure 9:
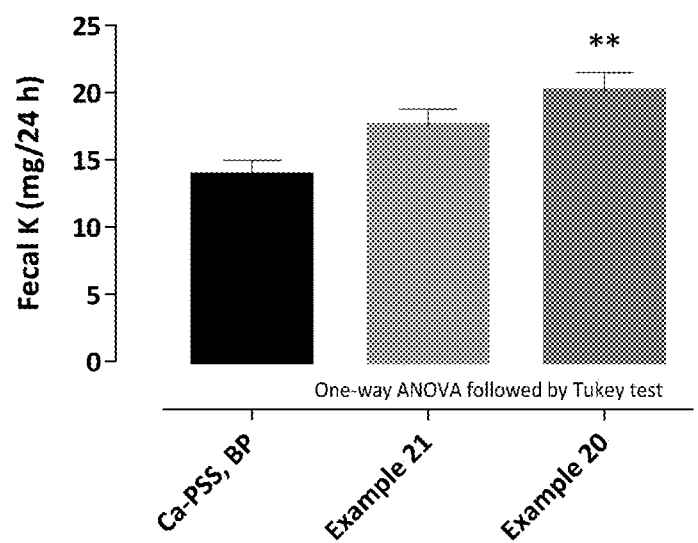
FIG. 9: shows fecal $K^+$ secretion of mice dosed with two Examples from the invention, blended in chow at 8%, wt/wt, and compared to Ca-PSS, BP as a control. Example 20 afforded the highest level of fecal potassium in this experiment.
Figure 10:
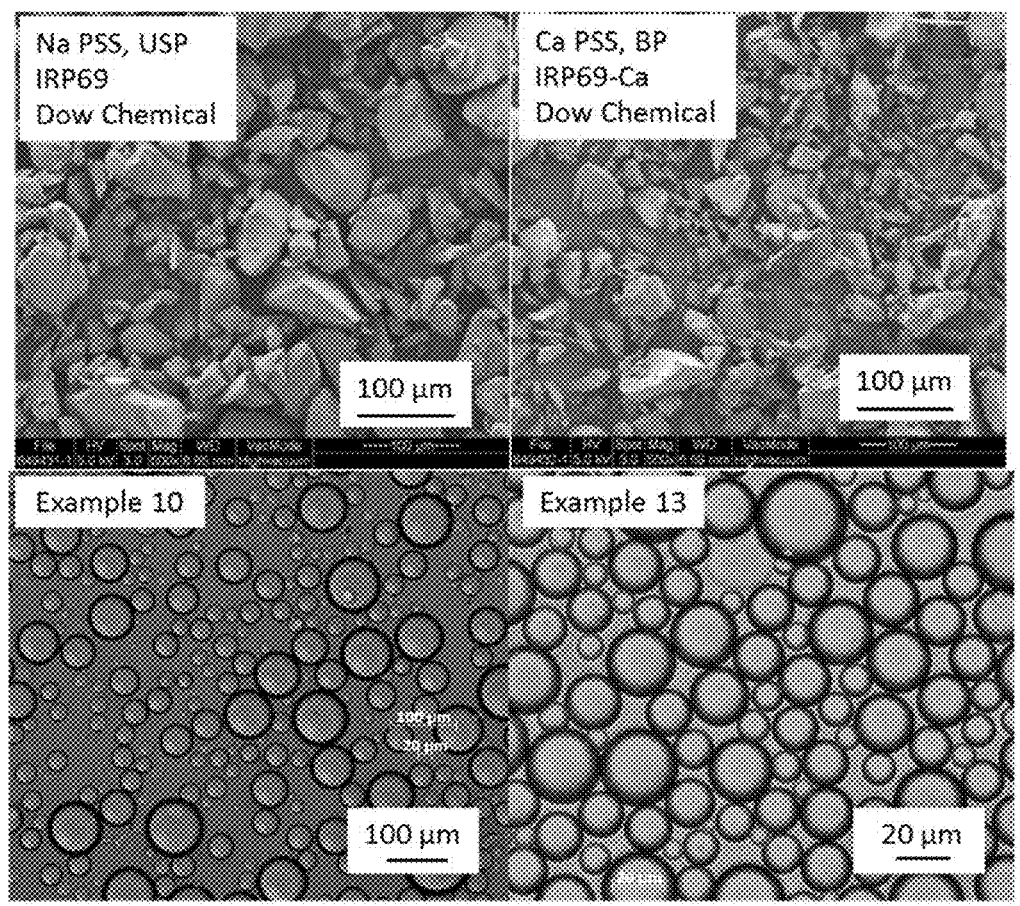
FIG. 10: shows scanning electron micrograph (SEM) images for Na-PSS, USP, Ca-PSS, USP, Example 13 and Example 10.

Using the methods in Biological Example 1, mice were dosed Ca-PSS blended into chow at 8% wt/wt. The test articles included Ca-PSS, BP as a control as well as Example 20 and Example 21, all of which were blended into chow at 8% wt/wt (FIG. 9). The highest level of fecal potassium was seen with Example 21.

Biological Example 11: Effects on Potassium Output in Mice Upon Dosing with Examples 30 and 31

Figure 14:
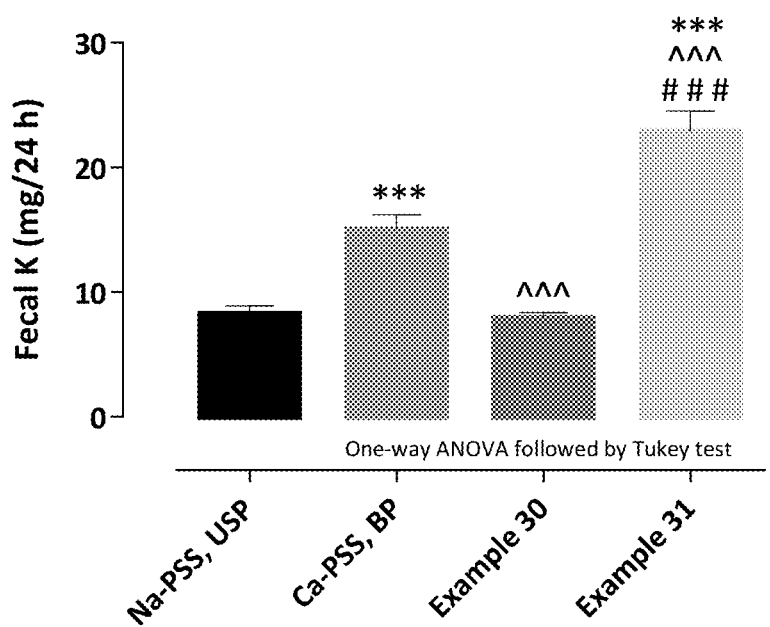
FIG. 14: shows the fecal $K^+$ excretion in mice treated with Examples 30 and 31 compared to Na-PSS, USP and Ca-PSS, BP as controls.

Using the methods in Biological Example 1, mice were dosed with resins blended into chow at 8% wt/wt. The test article groups included Na-PSS, USP (US Pharmacopeia grade; Purolite, Inc.), Ca-PSS, BP (British Pharmacopeia grade; Purolite, Inc.), Example 30, and Example 31. Groups dosed with Na-PSS, USP and Example 30 had significantly lower fecal ion output, and had a mean K+ output of ~8 mg/24 h. Ca-PSS, BP showed a mean K+ output of 15 mg/24 h. Example 31 had the highest K+ output in this example at 23 mg/24 h. Examples 30 and 31 were prepared from the same batch of sulfonated resin, and differ only in salt form. (FIG. 14

Biological Example 12: Effects on Fecal Potassium and Phosphorus Levels and Urinary Sodium and Potassium Levels in Mice Upon Dosing with Examples 32 and 33

Figure 15:
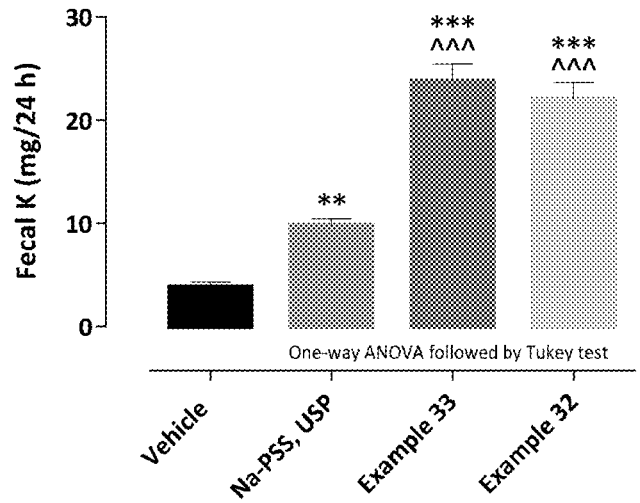
FIG. 15: shows the fecal and urinary $K^+$ excretion in mice treated with Examples 32 and 33 compared to Na-PSS, USP as a control and vehicle.
Figure 15:
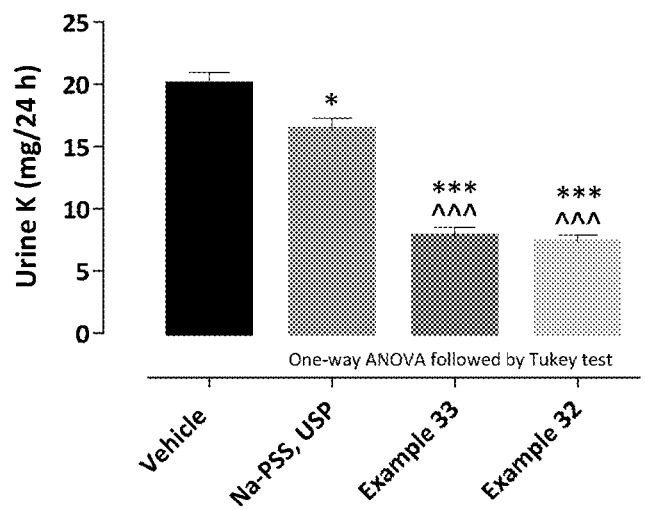
Figure 16:
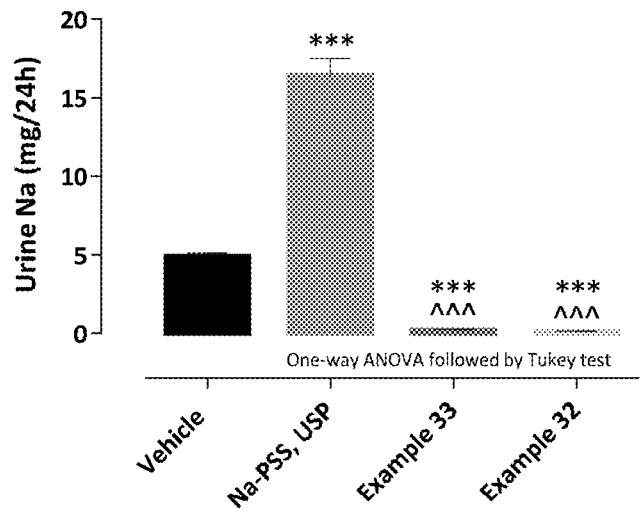
FIG. 16: shows the fecal excretion of phosphate and urinary excretion of sodium in mice treated with Examples 32 and 33 compared to Na-PSS, USP as a control and vehicle.
Figure 16:
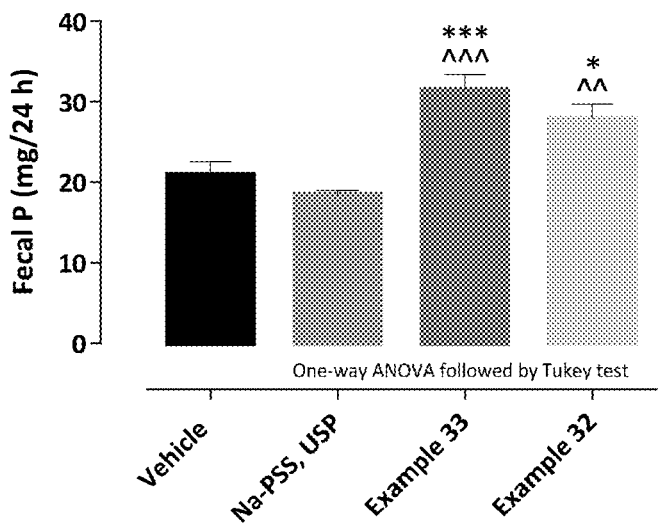
Figure 17:
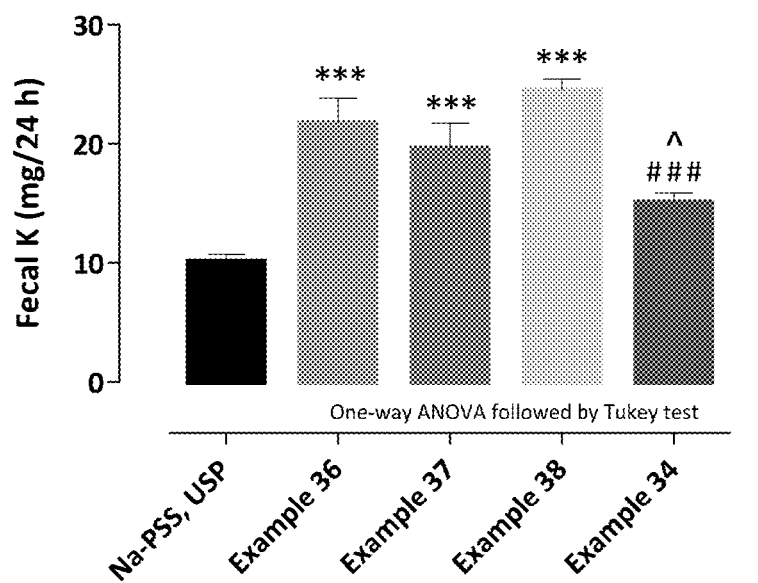
FIG. 17: shows the fecal $K^+$ excretion of mice dosed with Examples 36, 37, 38 and 34 compared to Na-PSS, USP as a control.

Using the methods in Biological Example 1, mice were dosed with resins blended into chow at 8% wt/wt. The test article groups included vehicle (normal chow without any drug), Na-PSS, USP, Example 32 and Example 33. Compared to Na-PSS, USP, both Example 32 and Example 33 resulted in 1) significantly higher amounts of fecal potassium, 2) significantly higher amounts of fecal phosphorus, and 3) significantly lower amounts of urine sodium and potassium. (FIG. 15 and FIG. 16)

Biological Example 13: Effects on Fecal Output in Mice Upon Dosing with Examples 34, 36, 37 and 37

Using the methods in Biological Example 1, mice were dosed with resins blended into chow at 8% wt/wt. The test article groups included Na-PSS, USP, Example 34, Example 36, Example 37 and Example 38. Fecal outputs of potassium are significantly elevated for all Examples relative to Na-PSS, USP, while Examples 36, 37, and 38 cause higher fecal potassium than Example 34. (FIG. 13)

Biological Example 14: A Phase I Randomized Study to Evaluate the Overall Consumer Acceptability of Taste and Mouth Feel of Example 29 and Formulations Thereof in Healthy Subjects The primary objective of the study was to evaluate the overall acceptability, as well as the acceptability of specific attributes, of taste and mouth feel of different oral formulations of Example 29 in comparison to a reference formulation (Resonium A; sodium polystyrene sulfonate [Na PSS], Sanofi-Aventis). This was a single center, randomized, crossover study to evaluate the taste of different oral formulations of Example 29 in healthy subjects. Visit 1 was open-label and Visit 2 was single-blind for Regimens E to I and open-label for Regimen J which was tested last. Formulation regimens are shown in Table 15, and include a systematic exploration of viscosity (by varying the amount of xanthan gum) and flavor (vanilla, citrus and mint).

Subjects were screened for inclusion in the study up to 28 days before dosing. Eligible subjects were admitted to the unit at approximately 21:00 on the evening before administration of the first regimen (Day −1) and were either discharged following the last taste test or remained on site until approximately 24 hours post-initial tasting, depending on whichever was most convenient for the subject.

and J. All formulations were administered orally. Taste was assessed using a questionnaire designed by Sensory Research Ltd (Cork, Ireland). The questionnaire asked subjects to rate the acceptability of several parameters (including smell, sweetness, flavor, mouth feel/texture and grittiness), as well as overall acceptability, on a 9 point scale (from 1—dislike everything to 9—like extremely).

No formal statistical testing was performed on screening or baseline data. The data from the results of the taste test were summarized (mean, median, SD, CV (%), minimum, maximum and N) by regimen for Visit 1 and Visit 2 separately. The number and percentage of subjects assigned to each grade of the acceptability categories on the taste questionnaire were also summarized by regimen for Visit 1 and Visit 2 separately. The formulation with the highest median score on overall acceptability was considered the formulation with the most acceptable taste profile and mouth feel.

Visit 1.

Regimen A (Resonium A) was consistently the poorest performing formulation throughout the taste assessment illustrating that Example 29, and formulations of Example 29, provide superior acceptability to Resonium A (Table 16).

TABLE 15

Formulations for Biological Example 14

| Regimen | Description | Formulation |
|---------|-------------|-------------|
| A | Resonium A reconstituted in water per patient instructions (3 mL-4 mL of water/g) | Resonium A contains saccharine (sweetener) and vanillin (flavouring agent) |
| B | Example 29 reconstituted (in water) with saccharine and vanillin | Identical excipients and equivalent formulation as Regimen A |
| C | Example 29 suspension formulation in vanilla flavour | Water-based suspension containing Example 29 (16.5%), vanillin (0.17%), methylparaben (0.18%) propylparaben (0.02%), sucralose powder (0.02%) and xanthan gum (0.67%) |
| D | Example 29 jelly formulations in vanilla flavour | Same as Regimen C except xanthan gum was present at 1.00% |
| E | Example 29 jelly formulation in vanilla flavour | Identical to Regimen D |
| F | Example 29 jelly formulation in citrus flavour | Same as Regiment D except vanillin was replaced with N&A Orange Flavor Powder, Flavor Producers item No. M680957M |
| G | Example 29 jelly formulation in wintergreen garden mint flavour | Equivalent to Regimen D except vanillin was replaced with Wintergreen Garden Mint (FL Emul. N&A WS), Sensient item No. SN2000016303 |
| H | Example 29 suspension low viscosity formulation in citrus yoghurt flavour | Same as Regimen F except xanthan gum was present at 0.37% |
| I | Example 29 intermediate viscosity formulation in citrus flavour | Same as Regimen F except xanthan gum was present at 0.67% |
| J | Example 29 reconstituted formulation in citrus flavour | Same as Regimen B except vanillin was replaced with N&A Orange Flavor Powder, Flavor Producers item No. M680957M |

Taste testing occurred over two visits. During Visit 1, each subject received 1 g each of regimen A, B, C and D in a randomized order using a Latin square design. Each regimen was administered as 4 to 6 mL of formulation, and each subject tasted all 4 regimens. During Visit 2, each subject received approximately 5 mL each of regimen E, F, G, H, I For Visit 1, although Regimen D ("jelly formulation" flavored by vanillin) had the highest overall median score, Regimen C (suspension formulation flavored by vanillin) produced similar results (Table 16). It was concluded that Regimen D would be reassessed at Visit 2, including favor variants.

TABLE 16

| | Taste Testing Results from Visit 1 | | | | | |
|---|---|---|---|---|---|---|
| | Median score (mean) | | | | | |
| Regimen | Smell | Sweetness | Flavor | Mouthfeel/ texture | Grittiness | Overall |
| Regimen A | 5.0 (5.5) | 5.0 (5.9) | 5.0 (5.4) | 3.0 (3.4) | 3.0 (2.8) | 4.0 (4.3) |
| Regimen B | 5.5 (6.1) | 6.0 (6.1) | 5.5 (5.6) | 4.5 (4.9) | 3.5 (4.3) | 5.0 (5.1) |
| Regimen C | 7.0 (7.0) | 7.0 (7.0) | 7.0 (6.6) | 6.0 (5.4) | 5.5 (5.9) | 6.0 (6.2) |
| Regimen D | 7.5 (7.2) | 7.0 (6.5) | 7.0 (6.1) | 6.0 (5.3) | 6.0 (6.3) | 7.0 (6.2) |

Highest scores per assessment are shown in bold

Visit 2.

Regimen E (jelly formulation in vanilla flavor, identical to Regimen D) had the joint highest median and highest mean scores for overall taste assessment, as well as scoring highest in most of the other taste assessments (Table 17). Regimen F afforded responses similar to Regimen E but scored higher for grittiness. Regimens E, F and G were all jelly formulations investigating different flavor options: vanilla, citrus and wintergreen garden mint, respectively. The vanilla and citrus scored the same median score for flavor, with vanilla scoring more consistently across subjects, suggesting this is the preferred flavor. Wintergreen mint had the lowest median scores for flavor. Regimens F, H, I and J were formulations of differing viscosity with the same citrus flavor. Regimen F (jelly formulation; 1% xanthan gum) had the highest median score compared to the other citrus formulations, confirming the results from the Visit 1 assessments (i.e. a "jelly" formulation is the preferred viscosity) (Table 17).

Example 29 consistently outperformed Resonium A in all aspects of the taste assessments. The jelly formulation was the preferred viscosity and vanilla (flavored by vanillin) and citrus were comparable for flavor; however, vanilla (flavored by vanillin) scored more consistently than citrus, suggesting it was the preferred flavor.

TABLE 17

| | Taste Testing Results from Visit 2 | | | | | |
|---|---|---|---|---|---|---|
| | Median score (mean) | | | | | |
| Regimen | Smell | Sweetness | Flavor | Mouthfeel/ texture | Grittiness | Overall |
| Regimen E | 7.0 (6.9) | 7.0 (7.0) | 7.0 (6.9) | 7.0 (6.5) | 6.0 (6.2) | 7.0 (6.8) |
| Regimen F | 6.5 (6.4) | 7.0 (6.8) | 7.0 (6.5) | 6.5 (6.4) | 6.5 (6.3) | 7.0 (6.4) |
| Regimen G | 5.0 (5.5) | 6.0 (5.5) | 6.0 (5.4) | 5.0 (5.3) | 5.5 (5.7) | 5.0 (5.3) |
| Regimen H | 6.0 (5.7) | 6.5 (6.1) | 6.0 (5.9) | 6.0 (5.8) | 5.5 (5.7) | 6.0 (5.7) |
| Regimen I | 6.0 (5.9 | 6.0 (6.2) | 6.0 (6.1) | 6.0 (5.8) | 5.0 (5.7) | 6.0 (6.0) |
| Regimen J | *5.0 (4.9)* | *5.5 (5.2)* | *4.5 (4.6)* | *4.0 (4.1)* | *4.0 (4.0)* | *4.0 (4.1)* |

Highest scores per assessment are shown in bold and lowest scores in italics

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A method for removing potassium from the gastrointestinal tract of a patient showing clinical signs of hyperkalemia or suspected of having hyperkalemia, comprising administering of a calcium salt of a potassium binding polymer to the patient, wherein the potassium binding polymer has the following structure:

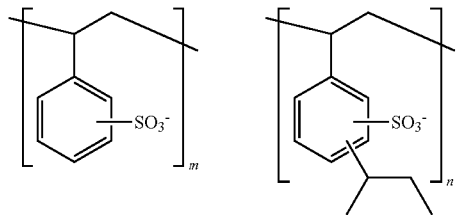

wherein the ratio of "m" and "n" provides a polymer having 1.0% to 1.9% cross-linking.

2. The method of claim 1, wherein the ratio of m to n is 68:1.

3. The method of claim 1, wherein the potassium binding polymer is characterized by a swelling ratio in water of between about 3 grams of water per gram of polymer to about 8 grams of water per gram of polymer.

4. The method of claim 1, wherein the potassium binding polymer is characterized by a swelling ratio in water of between about 3 grams of water per gram of polymer to about 4.5 grams of water per gram of polymer.

5. The method of claim 1, wherein the potassium binding polymer further comprises substantially spherical particles having a median diameter from about 5 μm to about 130 μm.

6. The method of claim 5, wherein the ratio of Dv(0.9):Dv(0.5) is about two or less and the ratio of Dv(0.5):Dv(0.1) is about five or less.

7. The method of claim 5, wherein the ratio of Dv(0.9):Dv(0.5) and the ratio of Dv(0.5):Dv(0.1) are each independently about two or less.

8. The method of claim 1, wherein the potassium binding polymer has a potassium exchange capacity from about 1 mEq to about 4 mEq per gram of potassium binding polymer.

9. The method of claim 1, wherein the patient is experiencing hyperkalemia.

10. The method of claim 1, wherein the patient is a human.

11. The method of claim 1, wherein the potassium binding polymer is characterized by a swelling ratio in water of about 3.3 grams of water per gram of polymer.

12. The method of claim 1, wherein the potassium binding polymer is characterized by a swelling ratio in water of about 4.3 grams of water per gram of polymer.

13. The method of claim 5, wherein the particles have an average particle size Dv(0.9) between about 80 μm to about 130 μm.

14. The method of claim 5, wherein the particles have an average particle size Dv(0.9) between about 90 μm to about 120 μm.

15. The method of claim 5, wherein the particles have an average particle size Dv(0.9) between about 40 μm to about 70 μm.

16. The method of claim 5, wherein the particles have an average particle size Dv(0.9) between about 50 μm to about 60 μm.

17. The method of claim 5, wherein the particles have an average particle size Dv(0.5) between about 60 μm to about 90 μm.

18. The method of claim 5, wherein the particles have an average particle size Dv(0.5) between about 70 μm to about 80 μm.

19. The method of claim 5, wherein the particles have an average particle size Dv(0.5) between about 20 μm to about 50 μm.

20. The method of claim 5, wherein the particles have an average particle size Dv(0.5) between about 30 μm to about 40 μm.

21. The method of claim 5, wherein the particles have an average particle size Dv(0.1) between about 20 μm to about 70 μm.

22. The method of claim 5, wherein the particles have an average particle size Dv(0.1) between about 30 μm to about 60 μm.

23. The method of claim 5, wherein the particles have an average particle size Dv(0.1) between about 5 μm to about 30 μm.

24. The method of claim 5, wherein the particles have an average particle size Dv(0.1) between about 6 μm to about 23 μm.

25. The method of claim 1, wherein the potassium binding polymer has a Mouth Feel score greater than 3.5.

26. The method of claim 1, wherein the potassium binding polymer has a Mouth Feel score greater than 4.5.

27. The method of claim 1, wherein the potassium binding polymer has a Mouth Feel score greater than 5.0.

28. A method for removing potassium from the gastrointestinal tract of a patient showing clinical signs of hyperkalemia or suspected of having hyperkalemia, comprising administering of a calcium salt of a crosslinked potassium binding polystyrene sulfonate divinylbenzene polymer, to the patient, wherein the crosslinked potassium binding polymer is characterized by a crosslinking of 1.0% to 1.9%.

* * * * *